United States Patent
Li et al.

(10) Patent No.: US 11,649,228 B2
(45) Date of Patent: May 16, 2023

(54) ZINC INDICATORS FOR CELLULAR IMAGING

(71) Applicant: The Board of Regents of the University of Texas System, Austin, TX (US)

(72) Inventors: Wen-Hong Li, Dallas, TX (US); Ebrahim Ghazvini Zadeh, Dallas, TX (US)

(73) Assignee: The Board of Regents of The University of Texas System, Austin, TX (US)

(*) Notice: Subject to any disclaimer, the term of this patent is extended or adjusted under 35 U.S.C. 154(b) by 598 days.

(21) Appl. No.: 16/665,647

(22) Filed: Oct. 28, 2019

(65) Prior Publication Data

US 2020/0131160 A1 Apr. 30, 2020

Related U.S. Application Data

(60) Provisional application No. 62/752,024, filed on Oct. 29, 2018.

(51) Int. Cl.
| | |
|---|---|
| C07D 405/14 | (2006.01) |
| G01N 1/28 | (2006.01) |
| G01N 21/76 | (2006.01) |
| C07F 3/06 | (2006.01) |
| C09K 11/54 | (2006.01) |

(52) U.S. Cl.
CPC ............. *C07D 405/14* (2013.01); *C07F 3/06* (2013.01); *C09K 11/54* (2013.01); *G01N 1/28* (2013.01); *G01N 21/76* (2013.01)

(58) Field of Classification Search
CPC ......... C07D 405/14; C07F 3/06; C09K 11/54; G01N 21/76; G01N 1/28
USPC ........................................................ 544/32
See application file for complete search history.

(56) References Cited

U.S. PATENT DOCUMENTS 8,530,183 B2   9/2013   Li et al.

OTHER PUBLICATIONS

Burdette et al., "Fluorescent sensors for Zn(2+) based on a fluorescein platform: synthesis, properties and intracellular distribution," *J Am Chem Soc*, 2001, 123 (32), 7831-7841.
Burdette et al., "ZP4, an improved neuronal Zn2+ sensor of the Zinpyr family," *J Am Chem Soc* 2003, 125 (7), 1778-1787.
Gee et al., "Detection and imaging of zinc secretion from pancreatic β-cells using a new fluorescent zinc indicator," *J Am Chem Soc* 2002, 124 (5), 776-778.
Jayaraman, "A novel method for the detection of viable human pancreatic β cells by flow cytometry using fluorophores that selectively detect labile zinc, mitochondrial membrane potential and protein thiols," *Cytometry A*, 2008, 73 (7), 615-625.
Komatsu et al., "Selective zinc sensor molecules with various affinities for Zn2+, revealing dynamics and regional distribution of synaptically released Zn2+ in hippocampal slices," *J Am Chem Soc*, 2005, 127 (29), 10197-10204.
Lukowiak et al., "Identification and purification of functional human β-cells by a new specific zinc-fluorescent probe," *J. Histochem. Cytochem.* 2001, 49 (4), 519-528.
McCormick et al., "X-ray fluorescence microscopy reveals accumulation and secretion of discrete intracellular zinc pools in the lactating mouse mammary gland," *PLoS ONE*, 2010, 5(6), e11078.
Meeusen et al., "TSQ (6-methoxy-8-p-toluenesulfonamidoquinoline), a common fluorescent sensor for cellular zinc, images zinc proteins," *Inorg Chem*, 2011, 50 (16), 7563-7573.
Que et al., "Quantitative mapping of zinc fluxes in the mammalian egg reveals the origin of fertilization-induced zinc sparks," *Nature Chemistry*, 2015, 7 (2), 130-139.
Rivera-Fuentes et al., "A Far-Red Emitting Probe for Unambiguous Detection of Mobile Zinc in Acidic Vesicles and Deep Tissue," *Chem Sci*, 2015, 6 (3), 1944-1948.
Solomou et al., "The Zinc Transporter S1c30a8/ZnT8 Is Required in a Subpopulation of Pancreatic alpha-cells for Hypoglycemia-induced Glucagon Secretion," *J Biol Chem*, 2015, 290 (35), 21432-21442.

(Continued)

*Primary Examiner* — Kahsay Habte
(74) *Attorney, Agent, or Firm* — Parker Highlander PLLC

(57) ABSTRACT

The present disclosure provides compounds of the formula:

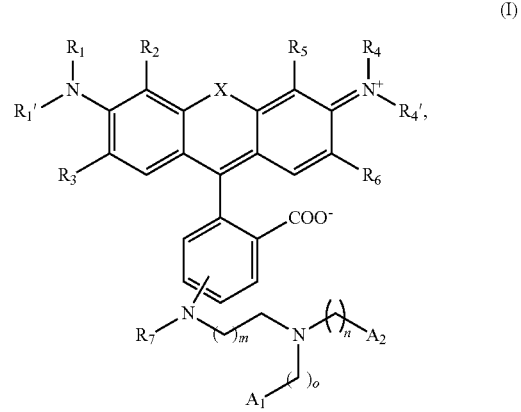

(I)

wherein the variables are defined herein. The present disclosure also provides methods of imaging $Zn^{2+}$ within granules in cells, such as pancreatic α-, β-, and δ-cells. The present disclosure also provides methods of sorting cells comprising the use of the compounds of the present disclosure.

23 Claims, 13 Drawing Sheets
(13 of 13 Drawing Sheet(s) Filed in Color)

(56) References Cited

OTHER PUBLICATIONS

Taki et al., "Emission ratiometric imaging of intracellular zinc: design of a benzoxazole fluorescent sensor and its application in two-photon microscopy," *J Am Chem Soc*, 2004, 126 (3), 712-713.

Wu et al., "Boron dipyrromethene fluorophore based fluorescence sensor for the selective imaging of Zn(II) in living cells," *Org Biomol Chem*, 2005, 3 (8), 1387-1392.

Zadeh et al., "ZIGIRs for the fluorescence imaging of $Zn^{2+}$ in secretory granules," *American Chemical Society*, Abstract BIOT 234, 2019.

Zalewski et al., "Video image analysis of labile zinc in viable pancreatic islet cells using a specific fluorescent probe for zinc," *J. Histochem. Cytochem*. 1994, 42 (7), 877-884.

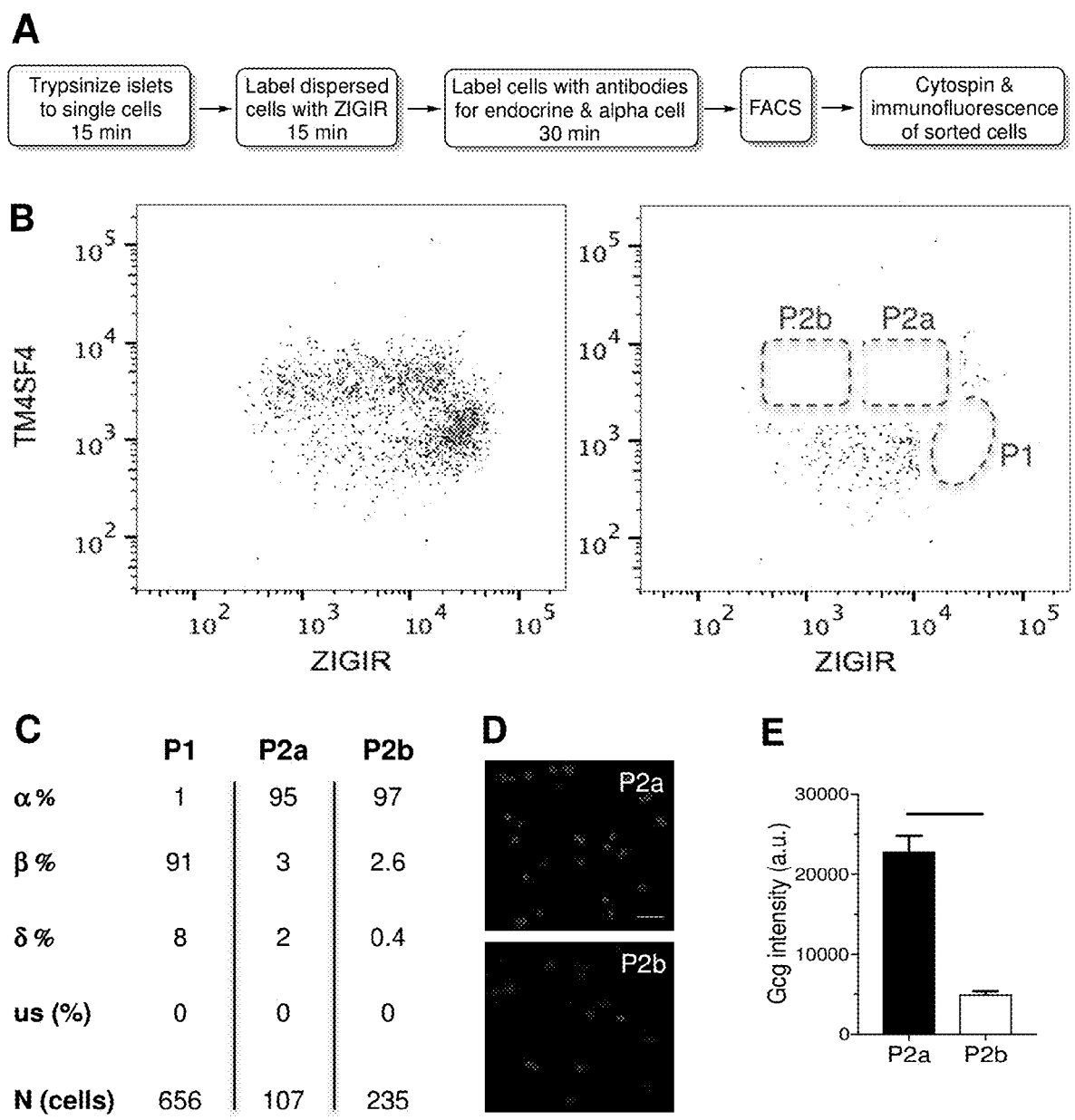
FIGS. 12A-E

FIGS. 14A-E

| Entry | Donor ID | Islet Source | Age (yr) | Gender | BMI | HbA1c | Cause of death |
|---|---|---|---|---|---|---|---|
| 1 | SAMN10737781 | IIDP | 66 | M | 27.2 | NA | Stroke |
| 2 | R299 | ADI | 44 | F | 25.4 | 4.7 | Neurological |
| 3 | SAMN11046361 | IIDP | 57 | M | 35.9 | NA | Stroke |
| 4 | SAMN11633049 | IIDP | 48 | M | 38.8 | NA | Cerebrovascular/stroke |
| 5 | R309 | ADI | 47 | F | 27.4 | 5.5 | Neurological |

ZINC INDICATORS FOR CELLULAR IMAGING

PRIORITY CLAIM

This application claims benefit of priority to U.S. Provisional Application Ser. No. 62/752,024, filed Oct. 29, 2018, the entire contents of which are hereby incorporated by reference.

GOVERNMENT SUPPORT CLAUSE

This invention was made with government support under Grant No. R01 GM07593 awarded by the National Institute of General Medical Sciences. The government has certain rights in the invention.

BACKGROUND

I. Field

The present disclosure relates to the fields of cell biology, imaging, diagnostics, and cytometry. pharmaceuticals, medicine and cell biology. More specifically, it relates to compounds which are useful in fluorescence microscopy. In addition, the compounds of the present disclosure are also compatible with flow cytometry and may be used to sort cells based on their insulin granule contents or other secretory granules enriched with zinc.

II. Description of Related Art

Numerous mammalian cells contain abundant $Zn^{2+}$ in their secretory granules. During stimulated secretion, $Zn^{2+}$ is co-released with other cargos into the extracellular medium, and the released $Zn^{2+}$ can function as an important signal to modulate the biochemistry of neighboring cells or distant cells via paracrine or endocrine mechanisms. Despite the biological importance of granular $Zn^{2+}$ activity, it remains challenging to monitor $Zn^{2+}$ levels in the lumen of secretory granules with high specificity and sensitivity. To fill this technological gap, a class of cell membrane permeable fluorescent zinc granule indicators, ZIGIRs, have been developed and are disclosed herein that display more than 30-fold fluorescence enhancement upon $Zn^{2+}$ binding.

SUMMARY

In some aspects, the present disclosure provides $Zn^{2+}$ sensors and methods of characterizing and sorting cells.

In one aspect, the present disclosure provides compounds of the formula:

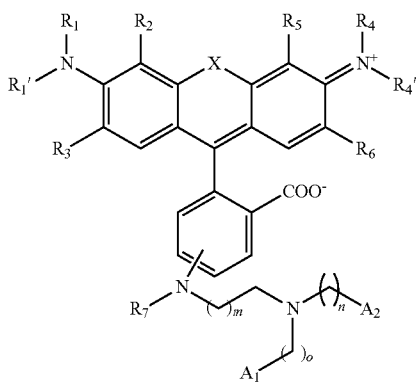

(I)

wherein:

X is —O—, —S—, —$SO_2$—, —$B(OR_a)$—, —$NR_b$—, or —$B(R_c)$—, wherein:

$R_a$ is hydrogen, alkyl$_{(C\leq12)}$, or substituted alkyl$_{(C\leq12)}$;

$R_b$ is hydrogen, alkyl$_{(C\leq12)}$, substituted alkyl$_{(C\leq12)}$, acyl$_{(C\leq12)}$, or substituted acyl$_{(C\leq12)}$;

$R_c$ is —Y-$A_3$, wherein:

Y is alkanediyl$_{(C\leq12)}$, alkenediyl$_{(C\leq12)}$, alkynediyl$_{(C\leq12)}$, or a substituted version of any of these groups;

$A_3$ is hydrogen, aryl$_{(C\leq12)}$, substituted aryl$_{(C\leq12)}$, heteroaryl$_{(C\leq12)}$, or substituted heteroaryl$_{(C\leq12)}$;

$R_1$ and $R_1'$ are each independently hydrogen; or alkyl$_{(C\leq12)}$, alkenyl$_{(C\leq12)}$, alkynyl$_{(C\leq12)}$, acyl$_{(C\leq12)}$, or a substituted version of any of these groups; or $R_1$ and $R_1'$ are taken together and is alkanediyl$_{(C2-7)}$, substituted alkanediyl$_{(C2-7)}$, -alkanediyl$_{(C1-3)}$-O-alkanediyl$_{(C1-3)}$-, or substituted -alkanediyl$_{(C1-3)}$-O-alkanediyl$_{(C1-3)}$-;

$R_4$ and $R_4'$ are each independently hydrogen; or alkyl$_{(C\leq12)}$, alkenyl$_{(C\leq12)}$, alkynyl$_{(C\leq12)}$, acyl$_{(C\leq12)}$, or a substituted version of any of these groups; or $R_4$ and $R_4'$ are taken together and is alkanediyl$_{(C2-7)}$, substituted alkanediyl$_{(C2-7)}$, -alkanediyl$_{(C1-3)}$-O-alkanediyl$_{(C1-3)}$-, or substituted -alkanediyl$_{(C1-3)}$-O-alkanediyl$_{(C1-3)}$-;

$R_2$, $R_3$, $R_5$, and $R_6$ are each independently hydrogen or halo;

$R_7$ is hydrogen, alkyl$_{(C\leq12)}$, substituted alkyl$_{(C\leq12)}$, acyl$_{(C\leq12)}$, or substituted acyl$_{(C\leq12)}$;

$A_1$ and $A_2$ are each independently heteroaryl$_{(C\leq12)}$ or substituted heteroaryl$_{(C\leq12)}$;

m is 1, 2, or 3;

n is 1, 2, 3, or 4; and o is 1, 2, 3, or 4; or compounds of the formula:

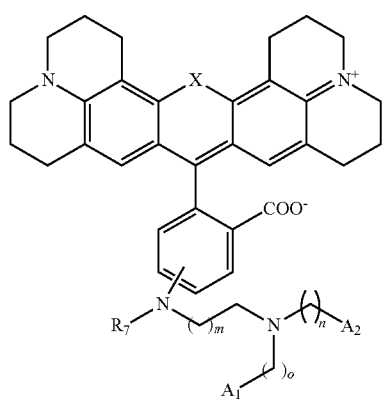

(II)

wherein:

X, $R_7$, $A_1$, $A_2$, m, n, and o are as defined above;

or a metal complex or a salt of either of these formulae.

In some embodiments, the compounds are compounds of formula (I) or a metal complex or a salt thereof. In some embodiments, the compounds are further defined as:

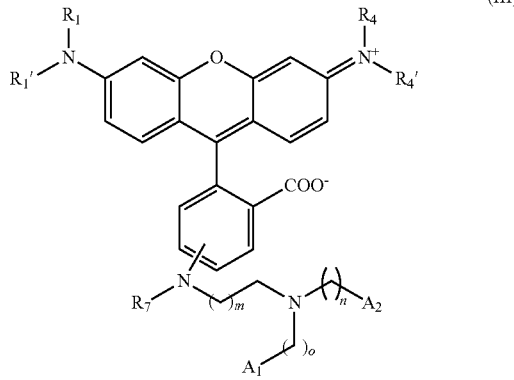

(III)

wherein:
R$_1$ and R$_1$' are each independently hydrogen; or
  alkyl$_{(C≤12)}$, alkenyl$_{(C≤12)}$, alkynyl$_{(C≤12)}$, acyl$_{(C≤12)}$, or a substituted version of any of these groups; or
R$_1$ and R$_1$' are taken together and is alkanediyl$_{(C2-7)}$, substituted alkanediyl$_{(C2-7)}$, -alkanediyl$_{(C1-3)}$-O-alkanediyl$_{(C1-3)}$-, or substituted -alkanediyl$_{(C1-3)}$-O-alkanediyl$_{(C1-3)}$-;
R$_4$ and R$_4$' are each independently hydrogen; or
  alkyl$_{(C≤12)}$, alkenyl$_{(C≤12)}$, alkynyl$_{(C≤12)}$, acyl$_{(C≤12)}$, or a substituted version of any of these groups; or
R$_4$ and R$_4$' are taken together and is alkanediyl$_{(C2-7)}$, substituted alkanediyl$_{(C2-7)}$, -alkanediyl$_{(C1-3)}$-O-alkanediyl$_{(C1-3)}$-, or substituted -alkanediyl$_{(C1-3)}$-O-alkanediyl$_{(C1-3)}$-;
R$_7$ is hydrogen, alkyl$_{(C≤12)}$, substituted alkyl$_{(C≤12)}$, acyl$_{(C≤12)}$, or substituted acyl$_{(C≤12)}$; A$_1$ and A$_2$ are each independently heteroaryl$_{(C≤12)}$ or substituted heteroaryl$_{(C≤12)}$;
m is 1, 2, or 3;
n is 1, 2, 3, or 4; and
o is 1, 2, 3, or 4;
or a metal complex or a salt thereof.

In further embodiments, the compounds are further defined as:

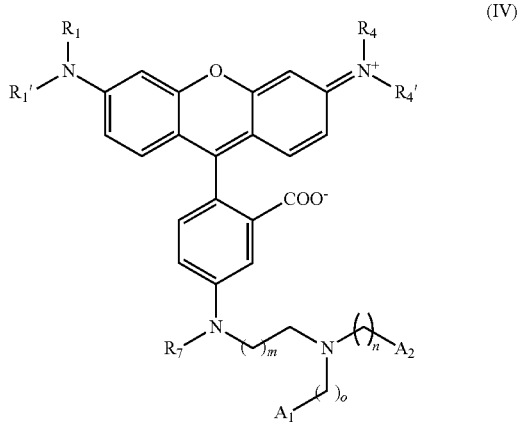

(IV)

wherein:
R$_1$ and R$_1$' are each independently hydrogen; or
  alkyl$_{(C≤12)}$, alkenyl$_{(C≤12)}$, alkynyl$_{(C≤12)}$, acyl$_{(C≤12)}$, or a substituted version of any of these groups; or
R$_1$ and R$_1$' are taken together and is alkanediyl$_{(C2-7)}$, substituted alkanediyl$_{(C2-7)}$, -alkanediyl$_{(C1-3)}$-O-alkanediyl$_{(C1-3)}$-, or substituted -alkanediyl$_{(C1-3)}$-O-alkanediyl$_{(C1-3)}$-;
R$_4$ and R$_4$' are each independently hydrogen; or
  alkyl$_{(C≤12)}$, alkenyl$_{(C≤12)}$, alkynyl$_{(C≤12)}$, acyl$_{(C≤12)}$, or a substituted version of any of these groups; or
R$_4$ and R$_4$' are taken together and is alkanediyl$_{(C2-7)}$, substituted alkanediyl$_{(C2-7)}$, -alkanediyl$_{(C1-3)}$-O-alkanediyl$_{(C1-3)}$-, or substituted -alkanediyl$_{(C1-3)}$-O-alkanediyl$_{(C1-3)}$-;
R$_7$ is hydrogen, alkyl$_{(C≤12)}$, substituted alkyl$_{(C≤12)}$, acyl$_{(C≤12)}$, or substituted acyl$_{(C≤12)}$;
A$_1$ and A$_2$ are each independently heteroaryl$_{(C≤12)}$ or substituted heteroaryl$_{(C≤12)}$;
m is 1, 2, or 3;
n is 1, 2, 3, or 4; and
o is 1, 2, 3, or 4;
or a metal complex or a salt thereof.

In some embodiments, R$_7$ is hydrogen. In some embodiments, m is 1. In some embodiments, n is 1. In some embodiments, o is 2. In some embodiments, A$_1$ is heteroaryl$_{(C≤12)}$, such as pyridin-2-yl. In some embodiments, A$_2$ is heteroaryl$_{(C≤12)}$, such as pyridin-2-yl. In some embodiments, R$_1$ is hydrogen. In other embodiments, R$_1$ is alkyl$_{(C≤12)}$ or substituted alkyl$_{(C≤12)}$. In some embodiments, R$_1$ is alkyl$_{(C≤12)}$. In further embodiments, R$_1$ is alkyl$_{(C≤6)}$, such as methyl or ethyl. In some embodiments, R$_1$' is hydrogen. In other embodiments, R$_1$' is alkyl$_{(C≤12)}$ or substituted alkyl$_{(C≤12)}$. In some embodiments, R$_1$' is alkyl$_{(C≤12)}$. In further embodiments, R$_1$' is alkyl$_{(C≤6)}$, such as methyl or ethyl. In some embodiments, R$_4$ is hydrogen. In other embodiments, R$_4$ is alkyl$_{(C≤12)}$ or substituted alkyl$_{(C≤12)}$. In some embodiments, R$_4$ is alkyl$_{(C≤12)}$. In further embodiments, R$_4$ is alkyl$_{(C≤6)}$, such as methyl or ethyl. In some embodiments, R$_4$' is hydrogen. In other embodiments, R$_4$' is alkyl$_{(C≤12)}$ or substituted alkyl$_{(C≤12)}$. In some embodiments, R$_4$' is alkyl$_{(C≤12)}$. In further embodiments, R$_4$' is alkyl$_{(C≤6)}$, such as methyl or ethyl.

In some embodiments, the compounds are further defined as:

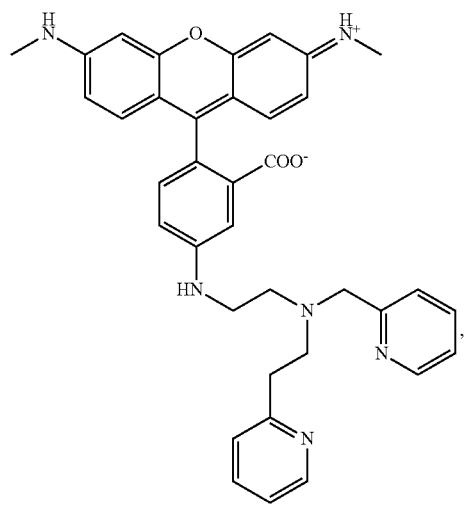

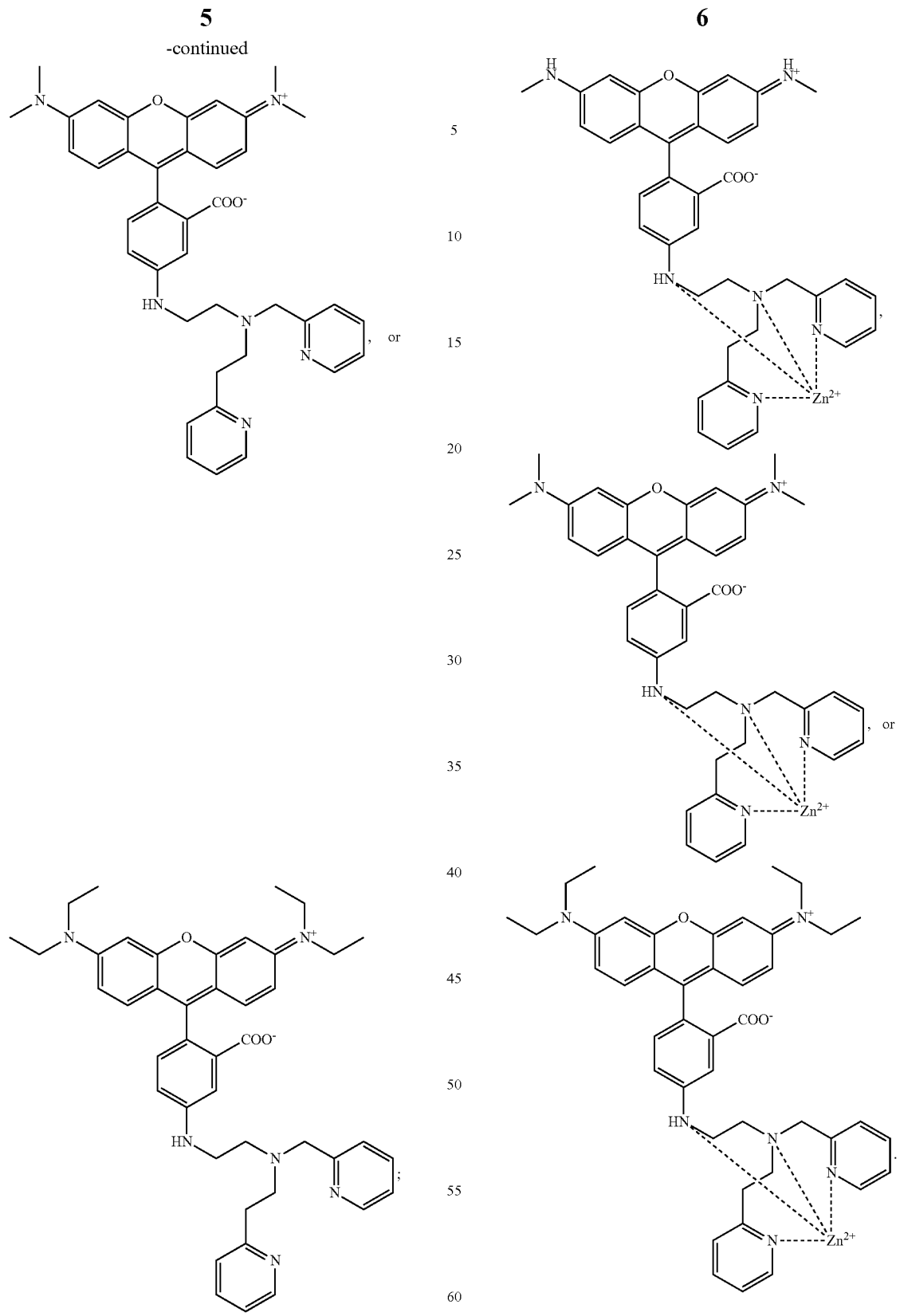

or a metal complex or a salt thereof.

In some embodiments, the metal complex comprises $Zn^{2+}$. In some embodiments, the metal complex is further defined as:

In another aspect, the present disclosure provides methods of detecting zinc ion ($Zn^{2+}$) in a cell comprising:
a) contacting the cell with a compound according to any one of claims 1-37; and
b) detecting fluorescence of the said compound following binding of zinc ion by said compound.

In some embodiments, the cell is a mammalian cell, such as a human cell or a murine cell. In some embodiments, the cell is a pancreatic cell, such as an α-cell, a β-cell, or a δ-cell. In some embodiments, detecting comprises confocal laser scanning microscopy. In some embodiments, the cell is an isolated cell, such as an isolated pancreatic islet. In other embodiments, the cell is in an intact tissue. In still other embodiments, the cell is in a living subject. In some embodiments, the methods further comprise detecting fluorescence at multiple time points.

In still another aspect, the present disclosure provides methods of characterizing a cell comprising:
a) contacting the cell with a compound according to any one of claims 1-40; and
b) detecting fluorescence using flow cytometry.

In some embodiments, the cell is a pancreatic cell, such as an α-cell, a β-cell, or a δ-cell. In some embodiments, the cell is an isolated cell. In other embodiments, the cell is in a living subject.

In yet another aspect, the present disclosure provides methods of sorting cells comprising:
a) contacting the cells with a compound according to any one of claims 1-40; and
b) sorting the cells by fluorescence-activated cell sorting (FACS).

In some embodiments, the cells are contacted with Ex4-Cy5 prior to FACS. In some embodiments, the cells are stem cells or pancreatic cells. In some embodiments, the cells are pancreatic cells, such as α-cells, β-cells, or δ-cells.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

FIG. 1A shows absorption spectrum of ZIGIR-1 in the presence or absence of $Zn^{2+}$. FIG. 1B shows fluorescence emission spectra of ZIGIR-1 (Ex=520 nm) at increasing $Zn^{2+}$ concentrations (nM): 0.63, 40, 160, 400, 630, 6300 (from bottom to top). FIG. 1C shows $Zn^{2+}$ titration of ZIGIR-1 as measured from its emission at 543 nm. The solid line represents the least square exponential fit. The insert shows the Hill plot with the solid line representing the linear regression fit ($r^2$=0.98). FIG. 1D shows ZIGIR-1 is refractory to physiological pH fluctuation and maintains its $Zn^{2+}$ responsivity between pH 5 to pH 8. ZIGIR-1 emission was measured in either nominally $Zn^{2+}$-free solutions or in 25 µM $Zn^{2+}$ solutions. The insert shows the effect of pH on ZIGIR-1 fluorescence intensity from pH 3 to pH 9.3 either in the presence (filled square) or the absence of $Zn^{2+}$ (open triangle).

FIGS. 2A & 2B show comparison of the absorption spectra (FIG. 2A) and emission spectra (FIG. 2B) of ZIGIRs. Each spectrum was normalized to its own peak value (100%). FIG. 2C shows summary of photophysical properties and $Zn^{2+}$ responses. $\phi_{fl}$ is the fluorescence quantum yield, a is the extinction coefficient, $n_H$ is the Hill coefficient, and FC is the fold change in fluorescence brightness ($\phi_{fl}\times\epsilon$) from the $Zn^{2+}$-free to the $Zn^{2+}$-bound state. FIGS. 2D & 2E show metal ion responses. The fluorescence intensity of ZIGIR-1 (FIG. 2D, 1 µM) or ZIGIR-2 (FIG. 2E, 1 µM) was measured in the presence of TPEN (10 µM) and excess ions (1 mM of $Na^+$, $K^+$, $Ca^{2+}$, or $Mg^{2+}$; 15 µM for the rest of ions including $Zn^{2+}$). The peak emission intensities were normalized to that of $Zn^{2+}$ solution ($F_{max}$).

FIG. 3A shows absorption spectrum of ZIGIR-2 in the presence or absence of $Zn^{2+}$. FIG. 3B shows fluorescence emission spectra of ZIGIR-2 (Ex=545 nm) at different $Zn^{2+}$ concentrations (nM): 0.63, 40, 160, 400, 630, 6300 (from bottom to top). FIG. 3C shows $Zn^{2+}$ titration of ZIGIR-2 as measured from its emission at 572 nm. The solid line represents the least square exponential fit. The insert shows the Hill plot with the solid line representing the linear regression fit ($r^2$=0.99). FIG. 3D shows ZIGIR-2 is refractory to physiological pH fluctuation and maintains its $Zn^{2+}$ responsivity between pH 5 to pH 9. ZIGIR-2 emission was measured in either nominally $Zn^{2+}$-free solutions or in 20 µM $Zn^{2+}$ solutions. The insert shows the effect of pH on ZIGIR-2 fluorescence intensity from pH 3 to pH 9.3 either in the presence (filled square) or the absence of $Zn^{2+}$ (open triangle).

FIG. 4A shows absorption spectrum of ZIGIR-3 in the presence or absence of $Zn^{2+}$. FIG. 4B shows fluorescence emission spectra of ZIGIR-3 (Ex=550 nm) at different $Zn^{2+}$ concentrations (nM): 0.63, 40, 160, 400, 630, 6300 (from bottom to top). FIG. 4C shows $Zn^{2+}$ titration of ZIGIR-3 as measured from its emission at 576 nm. The solid line represents the least square exponential fit. The insert shows the Hill plot with the solid line representing the linear regression fit ($r^2$=0.98). FIG. 4D shows ZIGIR-3 is refractory to physiological pH fluctuation and maintains its $Zn^{2+}$ responsivity between pH 5 to pH 9. ZIGIR-3 emission was measured in either nominally $Zn^{2+}$-free solutions or in 20 µM $Zn^{2+}$ solutions. The insert shows the effect of pH on ZIGIR-3 fluorescence intensity from pH 3 to pH 9.3 either in the presence (filled square) or the absence of $Zn^{2+}$ (open triangle).

FIG. 5E shows quantification of granular and bulk cytoplasm ZIGIR-1 signal (mean±SEM, average intensity of more than 250 ROIs from at least 40 cells under each condition).

μM), and in SAB containing TPEN (25 μM). Scale bar=10 m. FIG. 6E shows quantification of granular and bulk cytoplasm ZIGIR-2 signal (mean±SEM, average intensity of more than 250 ROIs from at least 40 cells under each condition).

FIGS. 7A-7C show wide field images of live MIN6 cells (FIG. 7A, DIC image) labeled with ZIGIR-2 (FIG. 7B) that subsequently immunostained for insulin (FIG. 7C, fixed cells). Scale bar=10 m. FIG. 7D shows scatterplot of the cellular ZIGIR-2 intensity and the corresponding insulin immunofluorescence of the same cells. Pearson's R value=mean±SEM, N=137 cells. FIG. 7E shows flow cytometry histogram of ZIGIR-2-labeled MIN6 cells. Cells were sorted into ZIGIR-2-High and ZIGIR-2-Low subsets. FIGS. 7F-7H show ZIGIR-2-High cells contain more insulin granules than ZIGIR-2-Low cells. Comparison of confocal immunofluorescence images (FIGS. 7F & 7G) between ZIGIR-2-High (top row) and ZIGIR-2-Low cells (bottom row). Cell nuclei were stained with DAPI. Images were acquired under the identical setting for the same protein. Average immunofluorescence intensities were quantified in FIG. 7H (mean±SEM, n=20 cells). ****P<0.0001.

FIG. 8A shows DIC and confocal ZIGIR-2 images of three mammalian cell lines in the SAB buffer. FIG. 8B shows confocal ZIGIR-2 and LysoTracker Green (LTG) images of the same cells after adding Zn/pyrithione (20 μM/10 μM) and LTG. Scale bar=10 m. ZIGIR-2 images were acquired under the same setting as in FIG. 6.

FIG. 9A shows an example confocal image of ZIGIR-2 labeled MIN6 cells. Cells were imaged every 5 sec over ~30 min. FIG. 9B shows quantification of the average ZIGIR-2 intensity over the course of time lapse imaging. N=120 random picked granules in 10 cells.

(FIG. 10A) Workflow of cell labeling, FACS and post-sorting analysis. (FIG. 10B) Flow cytometry histogram of ZIGIR-2 (top) and the corresponding 2D scatter plot (bottom) of mouse islet cells labeled with ZIGIR-2 and Ex4-Cy5. (FIG. 10C) Confocal immunofluorescence images (left column) of sorted islet cells using antibodies against three islet hormones. Cell type distributions in each subsets of sorted cells were shown to the right (Mean±SEM for 3 replicates; >200 cells were analyzed for P1 or P2 (>60 cells for P3 or P4) in each replicate). "Us" were cells unstained by any of the three hormone antibodies. (FIG. 10D) Confocal immunofluorescence images of a mouse pancreas section stained with antibodies against islet hormones and ZnT8. The enlarged images of the area highlighted by the dashed box are shown at the bottom row, with ZnT8 pseudo-colored in red and individual hormones in green to aid visualization of expression overlap. (FIG. 10E) Only ZIGIR-2, but not other $Zn^{2+}$ sensors, could resolve distinct islet endocrine cells according to their granular $Zn^{2+}$ levels. Flow cytometry histograms of mouse islet cells labeled with ZIGIR-2 and three other fluorescent $Zn^{2+}$ sensors.

FIGS. 12A-E. Flow cytometry analysis and sorting of human islet cells with ZIGIR-2. (FIG. 12A) Workflow of human islet labeling and analysis. (FIG. 12B) 2D scatter plot of human islet endocrine cells (donor SAMN10737781) by ZIGIR-2 and TM4SF4 labeling. Islet endocrine cells were sorted into three subsets. (FIG. 12C) Cell composition of the sorted P1, P2a and P2b subsets analyzed by immunofluorescence. Cells that were stained negatively for all three hormones (Ins, Gcg and Sst) were designated as unstained ("us"). N is the total number of cells that were imaged and analyzed. (FIG. 12D) Confocal images of Gcg immunofluorescence of sorted P2a and P2b subsets. (FIG. 12E) Quantification of Gcg immunofluorescence of sorted cells. (Mean±SEM, >50 cells for each subset. **** P<0.0001).

FIGS. 14A-F. Flow cytometry analysis and sorting of human islet cells with ZIGIR-2. (FIGS. 14A-B) An example of cell composition analysis of sorted human islet endocrine cells. Dispersed human islet cells labeled with HPi2, ZIGIR-2 and TM4SF4 were sorted into P1, P2a and P2b subsets (FIG. 14A) and analyzed by immuno-fluorescence (FIG. 14B). Cells that were stained negatively for all three hormones (Ins, Gcg and Sst) were designated as unstained ("us"). N is the total number of cells that the inventors measured. (FIGS. 14C-E) Additional examples of flow cytometry analysis of human islets endocrine cells. Broad distribution of ZIGIR-2 labeling among α-cells was repeatedly observed. The donor ID is shown above the plot. (FIG. 14F) Human donor islets information (IIDP: Integrated Islet Distribution Program; ADI: Alberta Diabetes Institute; NA: Not available)

DESCRIPTION OF ILLUSTRATIVE EMBODIMENTS

Figures 1A, 1B, 1C, 1D:
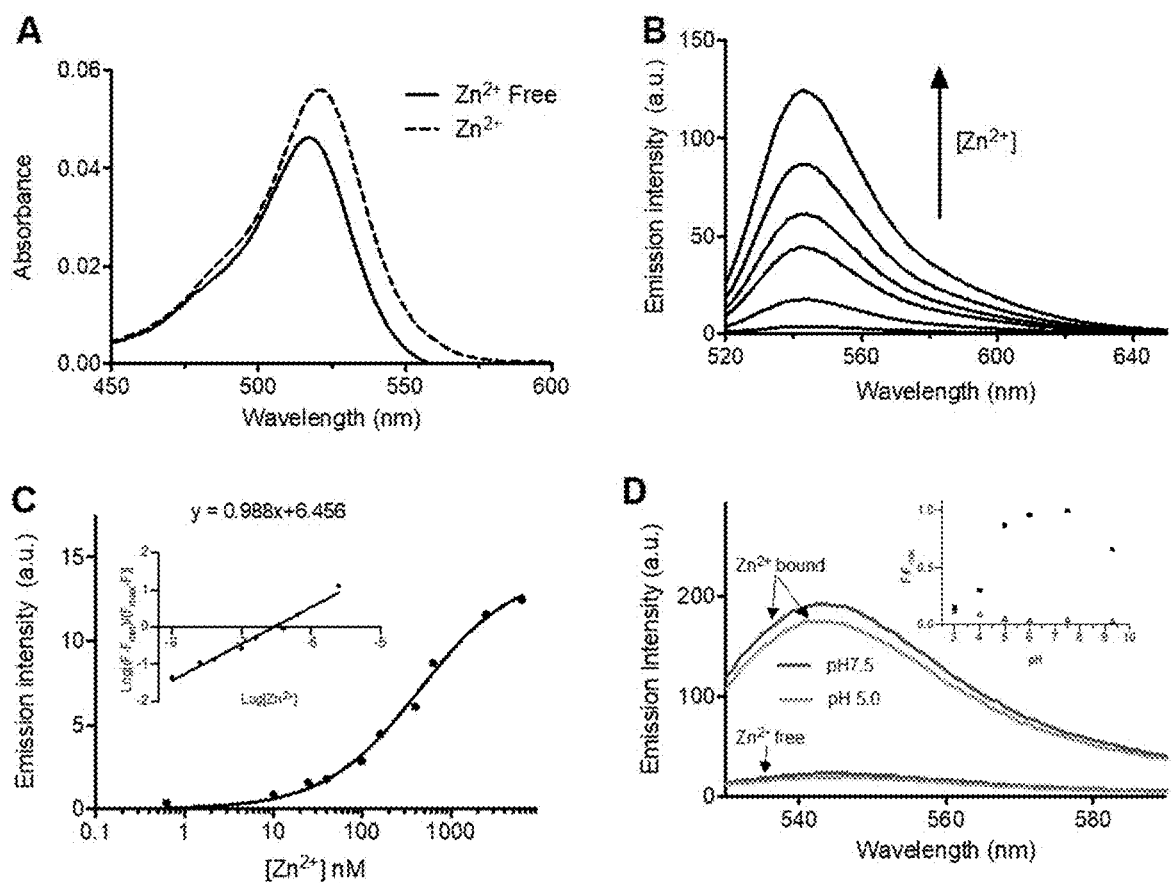
FIGS. 1A-1D show in vitro characterization of ZIGIR-1.

Provided herein are $Zn^{2+}$ sensors as well as methods of sorting cells. The present disclosure concerns compounds called ZIGIRs, which are acidotropic dyes, yet their fluorescence signal is refractory to pH fluctuation down to pH 5. This make them ideally suited for tracking $Zn^{2+}$ in acidic compartments, including secretory granules. In pancreatic islet β cells, ZIGIRs mark $Zn^{2+}$-rich insulin granules with high specificity and reveal dynamic movements of individual insulin granules in living cells by time-lapse imaging. In addition to fluorescence microscopy, ZIGIRs are also compatible with flow cytometry to enable sorting of heterogenous 3 cells based on their insulin granule contents. When combined with a fluorescent conjugate of exendin-4 peptide, ZIGIR-2 enables sorting of primary mouse islet cells into highly enriched β-cell, β-cell and δ-cell. Flow cytometry analysis of these cells revealed the hitherto unknown higher $Zn^{2+}$ activity in the glucagon granule than in the somatostatin granule. ZIGIRs may have wide applications for studying the regulation, biogenesis and trafficking of $Zn^{2+}$-rich granules in living cells and for engineering β cells with high insulin contents for treating diabetes. These and other embodiments will be described in more detail herein.

I. ROLE OF $Zn^{2+}$ $Zn^{2+}$ is an important metal ion that plays numerous roles in biochemistry, cell biology, and animal physiology. Among ~30,000 proteins identified in the human proteome, approximately 10% of these proteins have been identified as potential zinc-binding proteins (Andreini et al., 2006). Through coordination with specific amino acids of a polypeptide chain, $Zn^{2+}$ supports the folding, structure, and enzymatic activity of a large array of proteins. Hence, proper regulation and handling of $Zn^{2+}$ activity is vital for maintaining cell function and fitness, while malfunction of $Zn^{2+}$ homeostasis or aberrant $Zn^{2+}$ signaling has been associated with a variety of human diseases (Rink, 2011). To track cellular $Zn^{2+}$ levels and to investigate $Zn^{2+}$ regulation at high spatial and temporal resolution, fluorescent $Zn^{2+}$ indicators are invaluable tools as they enable imaging $Zn^{2+}$ dynamics owing to their high sensitivity and compatibility with live cell imaging (Li, 2015).

In addition to its ubiquitous roles in the regulation of $Zn^{2+}$-binding proteins and in cell signaling, $Zn^{2+}$ may also play more specialized roles in subcellular compartments including secretory granules of mammalian cells. Notably, a number of mammalian cells including islet β-cell, prostate epithelial cell, excitatory neuron in the hippocampus, mast cell and others contain a high level of $Zn^{2+}$ in their secretory granules (Frederickson et al., 2005). During stimulated secretion, $Zn^{2+}$ is co-released with other granular contents into the extracellular medium. Once released, $Zn^{2+}$ can affect the secretory cells from which $Zn^{2+}$ is released or nearby cells through autocrine or paracrine mechanism, respectively. Further, the released $Zn^{2+}$ may travel to distant cells through circulation to modulate the biochemistry of other tissues or organs by acting as an endocrine signal (Tamaki et al., 2013).

Despite the biological importance of granular $Zn^{2+}$ in secretory cells, it remains challenging to track the free granular $Zn^{2+}$ level in cells with high specificity and sensitivity. Fluorescent $Zn^{2+}$ indicators that can selectively mark secretory granules to report their luminal $Zn^{2+}$ levels would be invaluable tools for such studies. A few fluorescent $Zn^{2+}$ sensors, including Zinquin and Newport Green PDX, have been previously reported for imaging granular $Zn^{2+}$ (Zalewski et al., 1994 and Lukowski et al., 2001). However, these sensors are limited by their non-specific cellular distribution, pH sensitivity, and, in the case of Zinquin, requirement for UV excitation. Further, quinoline-based $Zn^{2+}$ sensors including Zinquin and TSQ (6-methoxy-8-p-toluenesulfonamido-quinoline) are known to bind to zinc proteins by forming the ternary complex comprising of sensor-$Zn^{2+}$-protein (Meeusen et al., 2011). This further complicates the interpretation of the source of the observed fluorescence signal.

More recent fluorescent $Zn^{2+}$ sensors that have been applied to image granular or vesicular $Zn^{2+}$ include FluoZin-3/AM (Gee et al., 2002), ZP4 (Burdette et al., 2003), ZincBY-1 (Que et al., 2015), and SpiroZin2 (Rivera-Fuentes et al., 2015). Since these $Zn^{2+}$ sensors bind $Zn^{2+}$ with nanomolar affinity (nM), they are not optimal for imaging $Zn^{2+}$ activity in $Zn^{2+}$-rich secretory granules that contain up to millimolar (mM) total $Zn^{2+}$.

For instance, in the insulin granule of pancreatic islet β-cells, six insulin molecules coordinate with two zinc ions to form the insulin-Zn complex (Dodoson and Steiner, 1998 and Emdin et al., 1980).

Since the granular insulin content is over 70 mM (Huang et al., 1995 and Matthews et al., 1982), total $Zn^{2+}$ in the insulin granule may reach or even exceed 20 mM. The free $Zn^{2+}$ activity in the insulin granule is not known but was thought to be in the micromolar range (Vinkenborg et al., 2009). Besides the undesirable high $Zn^{2+}$ affinity (nM), other limitations of previously reported granular $Zn^{2+}$ sensors include modest $Zn^{2+}$ responsivity (~5-fold enhancement) and promiscuous cellular distribution. FluoZin-3, for example, has been commonly used for imaging cytosolic $Zn^{2+}$, yet a number of studies have documented the localization of FluoZin-3 to other cellular compartments including vesicles (McCormick et al., 2010 and Wellenreuther et al., 2009), lysosome (Hwang et al., 2008, Roh et al., 2012, Kaltenberg et al., 2010, and Aydemir et al., 2009), and Golgi (Qin et al., 2013).

II. Compounds of the Present Disclosure

| Compound Identifier | Structure |
|---|---|
| ZIGIR-1 | [chemical structure] |
| ZIGIR-2 | [chemical structure] |

| Compound Identifier | Structure |
| --- | --- |
| ZIGIR-3 | (structure) |

The present disclosure provides a class of fluorescent $Zn^2$ sensors, ZIGIRs, for imaging $Zn^{2+}$-rich secretory granules. ZIGIRs possess a combination of properties desirable for cellular imaging including water solubility, membrane permeability, pH resistance, cellular labeling stability, and robust $Zn^2$ responsivity. Moreover, their unique combination of acidophilicity and relatively low $Zn^2$ affinity (~μM) endows this class of probes the unprecedented specificity, sensitivity and dynamic range for tracking $Zn^2$ activity in $Zn^{2+}$-rich secretory granules. Given the large variety of mammalian cells containing $Zn^{2+}$-rich secretory granules (Frederickson et al., 2005), ZIGIRs may find broad application in diverse biological imaging studies. These may include, among others, labeling secretory granules to investigate their movements and regulations (Tabei et al., 2013), tracking granule docking or priming during exocytosis (Yasuda et al., 2010 and Gandasi et al., 2018), and determining granular $Zn^{2+}$ changes following pharmacological or genetic perturbation of $Zn^{2+}$ transporting processes (Nicolson et al., 2009), etc. In recent years, an increasing number of genetically encoded $Zn^{2+}$ sensors have been developed (Hessels and Merkx, 2015). While these protein-based $Zn^{2+}$ indicators can be conveniently targeted to subcellular organelles once being fused with the appropriate localization sequences (Hessels et al., 2015), their $Zn^{2+}$ responsivity and dynamic range are generally below those of small synthetic probes such as ZIGIRs described herein. Further, cautions should be taken when expressing foreign protein cargos in the secretory granules as protein expression has been reported to perturb the dynamics and localization of native secretory granules (Michael et al., 2009 and Michael et al., 2004). Compared to the genetically encoded $Zn^{2+}$ sensors, a distinct advantage of small synthetics probes including ZIGIRs is that they can be easily applied to freshly isolated primary cells without the requirement of cell infection or protein expression, a property that can be especially valuable for studying $Zn^{2+}$ in primary cells of primates including human. Combining with the advanced imaging or flow cytometric analysis, the inventors expect that ZIGIRs may offer fresh opportunities for investigating the fluctuation and regulation of granule $Zn^{2+}$ level, tracking dynamics of $Zn^{2+}$-rich secretory granules, and isolating live cell clones with high granular $Zn^{2+}$/hormone contents to facilitate cell engineering for the cell replacement therapy of human diseases.

The $Zn^{2+}$ sensors of the present disclosure (also referred to as "$Zn^{2+}$ imaging agents" or "compounds of the present disclosure") are shown, for example, above, in the summary section, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, March's Advanced Organic Chemistry: Reactions, Mechanisms, and Structure, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

Unless explicitly stated to the contrary, all the compounds of the present disclosure are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the compounds of the present disclosure have the advantage that they may be more efficacious than, be less toxic than, be longer acting than, be more potent than, produce fewer side effects than, be more easily absorbed than, more metabolically stable than, more lipophilic than, more hydrophilic than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds of the present disclosure may contain one or more asymmetrically-substituted carbon or nitrogen atom and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration. In some embodiments, the present compounds may contain two or more atoms which have a defined stereochemical orientation.

Chemical formulas used to represent compounds of the present disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In some embodiments, compounds of the present disclosure function as prodrugs or can be derivatized to function as prodrugs. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively.

In some embodiments, compounds of the present disclosure exist in salt or non-salt form. With regard to the salt form(s), in some embodiments the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

III. CELLULAR IMAGING

As discussed above, the present disclosure provides for new and improved methods of imaging granular zinc. Four particular types of microscopy are well-suited for exploiting the use of ZIGIRs in cellular imaging—wide field fluorescence microscopy, total internal reflection fluorescence microscopy, confocal laser scanning microscopy of and two-photon laser scanning microscopy.

A. Wide Field Fluorescence Microscopy

Wide field fluorescence microscopy involves the use of any microscope where the image formation takes place by the optic without scanning. The lens directly forms an image, which can be projected on a camera or observed through the oculars. The light source usually is a mercury or xenon lamp but can also be an LED or laser. Thin specimens that do not require confocal imaging may be advantageously imaged using conventional wide field method as they offer unsurpassed signal to noise.

B. Total Internal Reflection Fluorescence Microscopy

A total internal reflection fluorescence microscope (TIRFM) is a type of microscope with which a thin region of a specimen, usually less than 200 nm, can be observed. TIRFM was developed at the University of Michigan in the early 1980s. A TIRFM uses evanescent wave to selectively illuminate and excite fluorophores in a restricted region of the specimen immediately adjacent to the glass-water interface. The evanescent wave is generated only when the incident light is totally reflected at the glass-water interface. The evanescent electromagnetic field decays exponentially from the interface, and thus penetrates to a depth of only approximately 100 nm into the sample medium. Thus, the TIRFM enables a selective visualization of surface regions such as the basal plasma membrane (which are about 7.5 nm thick) of cells as shown in the figure above. Note, however, that the region visualized is at least a few hundred nanometers wide, so the cytoplasmic zone immediately beneath the plasma membrane is necessarily visualized in addition to the plasma membrane during TIRF microscopy. The selective visualization of the plasma membrane renders the features and events on the plasma membrane in living cells with high axial resolution. TIRF can also be used to observe the fluorescence of a single molecule, making it an important tool of biophysics and quantitative biology.

C. Confocal Laser Scanning Microscopy

Confocal laser scanning microscopy (CLSM or LSCM) is a technique for obtaining high-resolution optical images with depth selectivity. The key feature of confocal microscopy is its ability to acquire in-focus images from selected depths, a process known as optical sectioning. Images are acquired point-by-point and reconstructed with a computer, allowing three-dimensional reconstructions of topologically-complex objects. For opaque specimens, this is useful for surface profiling, while for non-opaque specimens, interior structures can be imaged. For interior imaging, the quality of the image is greatly enhanced over simple microscopy because image information from multiple depths in the specimen is not superimposed. A conventional microscope "sees" as far into the specimen as the light can penetrate, while a confocal microscope only images one depth level at a time. In effect, the CLSM achieves a controlled and highly limited depth of focus.

In 1978, Thomas and Christoph Cremer designed a laser scanning process, which scans the three-dimensional surface of an object point-by-point by means of a focused laser beam, and creates the over-all picture by electronic means similar to those used in scanning electron microscopes. This CSLM design combined the laser scanning method with the 3D detection of biological objects labeled with fluorescent markers for the first time. During the next decade, confocal fluorescence microscopy was developed into a fully mature technology, in particular by groups working at the University of Amsterdam and the European Molecular Biology Laboratory (EMBL) in Heidelberg and their industry partners.

In a confocal laser scanning microscope, a laser beam passes through a light source aperture and then is focused by an objective lens into a small (ideally diffraction limited) focal volume within or on the surface of a specimen. In biological applications especially, the specimen may be fluorescent. Scattered and reflected laser light as well as any fluorescent light from the illuminated spot is then re-collected by the objective lens. A beam splitter separates off some portion of the light into the detection apparatus, which in fluorescence confocal microscopy will also have a filter that selectively passes the fluorescent wavelengths while blocking the original excitation wavelength. After passing a pinhole, the light intensity is detected by a photodetection device (usually a photomultiplier tube (PMT) or avalanche photodiode), transforming the light signal into an electrical one that is recorded by a computer.

The detector aperture obstructs the light that is not coming from the focal point, as shown by the dotted gray line in the image. The out-of-focus light is suppressed: most of the returning light is blocked by the pinhole, which results in sharper images than those from conventional fluorescence microscopy techniques and permits one to obtain images of planes at various depths within the sample (sets of such images are also known as "z stacks").

The detected light originating from an illuminated volume element within the specimen represents one pixel in the resulting image. As the laser scans over the plane of interest, a whole image is obtained pixel-by-pixel and line-by-line, whereas the brightness of a resulting image pixel corresponds to the relative intensity of detected light. The beam is scanned across the sample in the horizontal plane by using one or more (servo controlled) oscillating mirrors. This scanning method usually has a low reaction latency and the scan speed can be varied. Slower scans provide a better signal-to-noise ratio, resulting in better contrast and higher resolution. Information can be collected from different focal planes by raising or lowering the microscope stage or objective lens. The computer can generate a three-dimensional picture of a specimen by assembling a stack of these two-dimensional images from successive focal planes.

Confocal microscopy provides the capacity for direct, noninvasive, serial optical sectioning of intact, thick, living specimens with a minimum of sample preparation as well as a marginal improvement in lateral resolution. Biological samples are often treated with fluorescent dyes to make selected objects visible. However, the actual dye concentration can be low to minimize the disturbance of biological systems: some instruments can track single fluorescent molecules. Also, transgenic techniques can create organisms that produce their own fluorescent chimeric molecules (such as a fusion of GFP, green fluorescent protein with the protein of interest).

CLSM is a scanning imaging technique in which the resolution obtained is best explained by comparing it with another scanning technique like that of the scanning electron microscope (SEM). CLSM has the advantage of not requiring a probe to be suspended nanometers from the surface, as in an AFM or STM, for example, where the image is obtained by scanning with a fine tip over a surface. The distance from the objective lens to the surface (called the "working distance") is typically comparable to that of a conventional optical microscope. It varies with the system optical design, but working distances from hundreds of microns to several millimeters are typical.

In CLSM a specimen is illuminated by a point laser source, and each volume element is associated with a discrete scattering or fluorescence intensity. Here, the size of the scanning volume is determined by the spot size (close to diffraction limit) of the optical system because the image of the scanning laser is not an infinitely small point but a three-dimensional diffraction pattern. The size of this diffraction pattern and the focal volume it defines is controlled by the numerical aperture of the system's objective lens and the wavelength of the laser used. This can be seen as the classical resolution limit of conventional optical microscopes using wide-field illumination. However, with confocal microscopy it is even possible to improve on the resolution limit of wide-field illumination techniques because the confocal aperture can be closed down to eliminate higher orders of the diffraction pattern. For example, if the pinhole diameter is set to 1 Airy unit then only the first order of the diffraction pattern makes it through the aperture to the detector while the higher orders are blocked, thus improving resolution at the cost of a slight decrease in brightness. In fluorescence observations, the resolution limit of confocal microscopy is often limited by the signal to noise ratio caused by the small number of photons typically available in fluorescence microscopy. One can compensate for this effect by using more sensitive photodetectors or by increasing the intensity of the illuminating laser point source. Increasing the intensity of illumination later risks excessive bleaching or other damage to the specimen of interest, especially for experiments in which comparison of fluorescence brightness is required. When imaging tissues which are differentially refractive, such as the spongy mesophyll of plant leaves or other air-space containing tissues, spherical aberrations that impair confocal image quality are often pronounced. Such aberrations however, can be significantly reduced by mounting samples in optically transparent, non-toxic perfluorocarbons such as perfluorodecalin, which readily infiltrates tissues and has a refractive index almost identical to that of water.

D. Two Photon Laser Scanning Microscopy

Two-photon excitation microscopy is a fluorescence imaging technique that allows imaging of living tissue up to a very high depth, that is up to about one millimeter. Being a special variant of the multiphoton fluorescence microscope, it uses red-shifted excitation light which can also excite fluorescent dyes however for each excitation two photons of the infrared light are absorbed. Using infrared light minimizes scattering in the tissue. Due to the multiphoton absorption background signal is strongly suppressed. Both effects lead to the increased penetration depth for these microscopes. However, the resolution remains diffraction-limited. Two-photon excitation can be a superior alternative to confocal microscopy due to its deeper tissue penetration, efficient light detection and reduced phototoxicity.

The concept of two-photon excitation is based on the idea that two photons of comparably lower energy than needed for one photon excitation can also excite a fluorophore in one quantum event. Each photon carries approximately half the energy necessary to excite the molecule. An excitation results in the subsequent emission of a fluorescence photon, typically at a higher energy than either of the two excitatory photons. The probability of the near-simultaneous absorption of two photons is extremely low. Therefore, a high flux of excitation photons is typically required, usually a femtosecond laser.

The most commonly used fluorophores have excitation spectra in the 400-500 nm range, whereas the laser used to excite the two-photon fluorescence lies in the ~700-1000 nm (infrared) range. If the fluorophore absorbs two infrared photons simultaneously, it will absorb enough energy to be raised into the excited state. The fluorophore will then emit a single photon with a wavelength that depends on the type of fluorophore used (typically in the visible spectrum). Because two photons are absorbed during the excitation of the fluorophore, the probability for fluorescent emission from the fluorophores increases quadratically with the excitation intensity.

Therefore, much more two-photon fluorescence is generated where the laser beam is tightly focused than where it is more diffuse. Effectively, excitation is restricted to the tiny focal volume (~1 femtoliter), resulting in a high degree of rejection of out-of-focus objects. This localization of excitation is the key advantage compared to single-photon excitation microscopes, which need to employ additional elements such as pinholes to reject out-of-focus fluorescence. The fluorescence from the sample is then collected by a high-sensitivity detector, such as a photomultiplier tube. This observed light intensity becomes one pixel in the eventual image; the focal point is scanned throughout a desired region of the sample to form all the pixels of the image.

In two-photon excitation microscopy, an infrared laser beam is focused through an objective lens. The Ti-sapphire laser normally used has a pulse width of approximately 100 femtoseconds and a repetition rate of about 80 MHz, allowing the high photon density and flux required for two photons absorption and is tunable across a wide range of wavelengths.

The use of infrared light to excite fluorophores in light-scattering tissue has added benefits. Longer wavelengths are scattered to a lesser degree than shorter ones, which is a benefit to high-resolution imaging. In addition, these lower-energy photons are less likely to cause damage outside the focal volume. Compared to a confocal microscope, photon detection is much more effective since even scattered photons contribute to the usable signal. There are several caveats to using two-photon microscopy: The pulsed lasers needed for two-photon excitation are much more expensive then the constant wave (CW) lasers used in confocal microscopy. The two-photon absorption spectrum of a molecule may vary significantly from its one-photon counterpart. For very thin objects such as isolated cells, single-photon (confocal) microscopes can produce images with higher optical resolution due to their shorter excitation wavelengths. In scattering tissue, on the other hand, the superior optical sectioning and light detection capabilities of the two-photon microscope result in better performance.

IV. CELL STAINING

In certain embodiments, it may prove useful to counterstain cells with other agents, such as those that identify cell surface markers, or internal structures such as DNA, RNA, mitochondria, etc. Stains, marker agents or antibodies directed to these surface molecules can not only permit cell boundary identification, but can facilitate characterization of a cell being of a certain type, such as diseased (e.g., cancerous), or of a certain type, e.g., vasculature versus muscle.

A non-limiting list of dyes include nucleic acid dyes such as acridine orange, 7-aminoactinomycin D, ethidium bromide, ethidium homodimer, LDS 751, propidium iodide, Syto 11, 12, 20, 22, 16, Syto 14, 15, 25, Syto 17, 59, 61, Sytox green, thiazole blue, thiazole orange, ToPro1, ToPro3; antibody labeling dyes for cell surface, cytoplasmic and nuclear antigens such as Alexa 488, APC, BODIPY FL, BODIPY 630/650, CY5, CY5.5, ECD, FITC, cytokeratin, hematoxylin-eosin, fluorescein-conjugated lectin, *Ulex europaeus* I (F-UEAI) counterstained with Harris hematoxylin, periodic acid-Schiff (PAS), bromodeoxyuridine, cathepsin B, Texas Red, rhodamine, cyanine, phycoerythrin, phycocyanin, allophycocyanin, o-phthaldehyde, fluorescamine, oregon green 488, PE, PE-APC, PE-Cy5, PerCP, PE-TR, rhodamine green and rhodol green; cell metabolism dyes such as BCECF, calcium green, carboxy-DCF, carboxy SNARF-1 AM, DilCn5, DiOCn3, Fluo-3, Fura Red, Green Fluorescent Protein, JC-1 and NBD-C6-Ceramide; UV dyes such as Hoechst and Dapi. Other stains are known in the art may be used, and are summarized in references such as Bedrossian (1998), herein incorporated by reference. The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

A fluorescent label with an excitation wavelength capable of being excited by the fluorescent emission of another fluorescent dye is contemplated.

The cell nucleus may be stained by specific stains, such as propidium iodide or sytox green. In a specific embodiment propidium iodide is used. The propidium iodide, in a specific embodiment, is excited by a 488 nm wavelength argon-ion laser, and the red fluorescence emission is measured by appropriate detector.

Differences between apical and basal surfaces may be determined. Topography (morphology) of a specific cell may be smooth, asymmetrical, symmetrical, uneven, or marked with small or large pocks. Extensions on cells such as filopodia may be visualized.

V. CELL SAMPLES

As discussed above, while the disclosed compounds may be advantageously practiced on isolated cells, such as those in culture, it may also be used on tissue samples. Such samples can be achieved by any one of a variety of different means, largely depending on the nature of the sample to examined. For example, for examination of solid tissues, samples can be taken by biopsy which can be obtained through needle biopsy, endocscopy, laproscopy, or systoscopy. Alternatively, scrapings of cells can be taken from the tissue of interest.

Once obtained, it may be necessary to further process the samples before they are examined. Further processing may include various forms of physical arrangement of the samples. For example, with solid tissues, it may be necessary to prepare thin sections. It also may be desired to dissociate the cells from each other and disperse them as a thin film monolayer. Dissociation may be accomplished by physical or enzymatic means. Similarly, dissociated cells in fluid samples or in scrapings may be concentrated and dispersed in a monolayer. In other instances, it may be desirable to concentrate disperse cells as a pellet. This can be accomplished by centrifugation of the liquid samples. Further processing includes chemical treatments such as fixation steps. Exemplary treatments include alcohol fixation. Suitable alcohols include methanol, ethanol, propanol, isopropanol, n-butanol and t-butanol. Microscopic slides, typically glass or quartz, may be prepared using the concentrated or processed specimen to optimize cellular content.

VI. KITS

Any of the compounds or compositions described herein may be comprised in a kit. The kits will thus comprise, in suitable container means, compounds of the present disclosure, alternatively also include fluorescent dyes, antibodies, secondary antibodies, buffers and washes.

The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the fluorophore and antibodies, additional agent, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the fluorophore and antibodies are placed, preferably, suitably allocated. The kits may also comprise a second container means for containing a sterile, pharmaceutically acceptable buffer and/or other diluent.

The kits of the present disclosure will also typically include a means for containing the vials in close confinement for commercial sale, such as, e.g., injection and/or blow-molded plastic containers into which the desired vials are retained.

An example of a kit of the present disclosure is an islet cell labeling and sorting kit. The kit is intended for labeling pancreatic islet cells for analysis by fluorescent microscopy or flow cytometry, and for sorting islet cells by fluorescence activated cell sorting (FACS). The kit contains the following components:

Component 1: A fluorescent $Zn^{2+}$ sensor of the present disclosure, such as ZIGIR-1, ZIGIR-2, ZIGIR-3;

Component 2: A fluorescently labeled peptide or antibody that bind to a cell surface receptor expressed on islet cells. An example peptide is an exendin-4 peptide containing a Cy5 label (Scheme 3). An example antibody is an antibody that binds to the GLP-1 receptor expressed on islet beta cells. The antibody can be either directly conjugated with a fluorescent dye or be detected by a secondary antibody labeled with a fluorophore; and Component 3: A physiological saline solution (for example, a secretion assay buffer containing 114 mM NaCl, 4.7 mM KCl, 1.2 mM KH2PO4, 2.5 mM CaCl2, 1.16 mM MgSO4, 3 mM glucose, and 20 mM Hepes, pH 7.4) for dissolving or diluting Component 1 and Component 2. The mixed solution containing all three components is applied to live islet cells. After labeling, the cells can be analyzed by flow cytometry or separated into distinct cell subsets (alpha cell, beta cell, and delta cell) by FACS (FIG. 10).

VII. DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO₂H); "halo" means independently —F, —Cl, —Br or —I; "amino" means —NH₂; "hydroxyamino" means —NHOH; "nitro" means —NO₂; imino means =NH; "cyano" means —CN; "isocyanyl" means —N=C=O; "azido" means —N₃; in a monovalent context "phosphate" means —OP(O)(OH)₂ or a deprotonated form thereof; in a divalent context "phosphate" means —OP(O)(OH)O— or a deprotonated form thereof; "mercapto" means —SH; and "thio" means =S; "sulfonyl" means —S(O)₂—; and "sulfinyl" means —S(O)—.

In the context of chemical formulas, the symbol "—" means a single bond, "=" means a double bond, and "≡"
means triple bond. The symbol "- - - -" represents an optional bond, which if present is either single or double. The symbol "⸺" represents a single bond or a double bond. Thus, the formula

covers, for example,

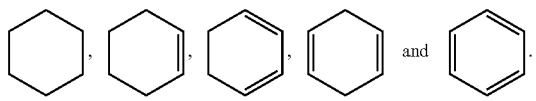

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀■" means a single bond where the group attached to the thick end of the wedge is "out of the page." The symbol "⋅⋅⋅ɪɪɪ" means a single bond where the group attached to the thick end of the wedge is "into the page". The symbol "∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

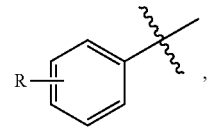

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

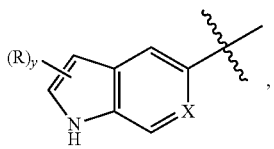

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" or "C=n" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. Except as noted below, every carbon atom is counted to determine whether the group or compound falls with the specified number of carbon atoms. For example, the group dihexylamino is an example of a dialkylamino$_{(C=12)}$ group; however, it is not an example of a dialkylamino$_{(C=6)}$ group. Likewise, phenylethyl is an example of an aralkyl$_{(C=8)}$ group. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system. An aromatic compound or chemical group may be depicted as a single resonance structure; however, depiction of one resonance structure is taken to also refer to any other resonance structure. For example:

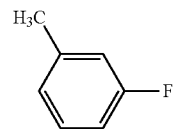

is also taken to refer to

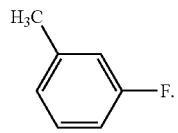

Aromatic compounds may also be depicted using a circle to represent the delocalized nature of the electrons in the fully conjugated cyclic π system, two non-limiting examples of which are shown below:

The term "alkyl" refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, iPr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above.

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" refers to a divalent unsaturated aliphatic group, with two carbon atoms as points of attachment, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule.

The term "alkynyl" refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. The term "alkynediyl" refers to a divalent unsaturated aliphatic group, with two carbon atoms as points of attachment, a linear or branched acyclic structure, at least one nonaromatic carbon-carbon triple bond, no carbon-carbon double bonds, and no atoms other than carbon and hydrogen. The groups —C≡C—, —C≡CCH$_2$—, and —CH$_2$C≡CCH$_2$— are non-limiting examples of alkynediyl groups. It is noted that while the alkynediyl group is aliphatic, once connected at both ends, this group is not precluded from forming part of an aromatic structure. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

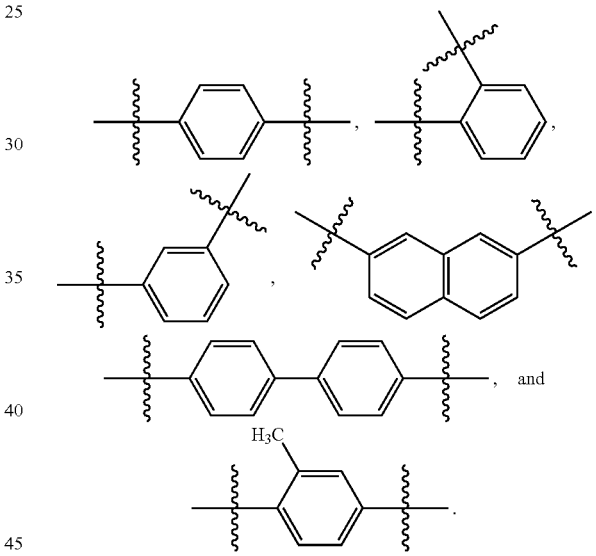

The term "heteroaryl" refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include benzoxazolyl, benzimidazolyl, furanyl, imidazolyl (Im), indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes.

The term "acyl" refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group.

When a chemical group is used with the "substituted" modifier, one or more hydrogen atom has been replaced, independently at each instance, by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. For example, the following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups. Non-limiting examples of substituted aralkyls are: (3-chlorophenyl)-methyl, and 2-chloro-2-phenyl-eth-1-yl. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients.

An "active ingredient" (AI) or active pharmaceutical ingredient (API) (also referred to as an active compound, active substance, active agent, pharmaceutical agent, agent, biologically active molecule, or a therapeutic compound) is the ingredient in a pharmaceutical drug that is biologically active.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug, agent, or preparation) is a composition used to diagnose, cure, treat, or prevent disease, which comprises an active pharmaceutical ingredient (API) (defined above) and optionally contains one or more inactive ingredients, which are also referred to as excipients (defined above).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present disclosure. The prodrug itself may or may not also have activity with respect to a given target protein. For example, a compound comprising a hydroxy group may be administered as an ester that is converted by hydrolysis in vivo to the hydroxy compound. Non-limiting examples of suitable esters that may be converted in vivo into hydroxy compounds include acetates, citrates, lactates, phosphates, tartrates, malonates, oxalates, salicylates, propionates, succinates, fumarates, maleates, methylene-bis-(3-hydroxynaphthoate, gentisates, isethionates, di-p-toluoyltartrates, methanesulfonates, ethanesulfonates, benzenesulfonates, p-toluenesulfonates, cyclohexylsulfamates, quinates, and esters of amino acids. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringeable liquid or other injectable formulations.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

VIII. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Results and Discussion

A. Design, Synthesis, and Physicochemical Characterization

The design, synthesis, in vitro and in vivo characterization of a class of fluorescent zinc granule indicators, ZIGIRs (Scheme 1) is disclosed herein. ZIGIRs bind $Zn^{2+}$ with micromolar affinity and display more than 30-fold fluorescence enhancement upon $Zn^{2+}$ complexation. In cells, ZIGIRs are found to accumulate in acidic granules including secretory granules. Importantly, ZIGIRs are refractory to cellular pH fluctuations and maintain robust $Zn^{2+}$ responsivity at both neutral and acidic pH. The pH resistance makes ZIGIRs ideally suitable for imaging $Zn^{2+}$ activity in acidic compartments such as secretory granules. Because of their $Zn^{2+}$ affinity in the micromolar range, ZIGIRs fluorescence is only observed in $Zn^{2+}$-rich secretory granules but not in other cellular compartments. Besides fluorescence microscopy, ZIGIRs are also compatible with flow cytometry and fluorescence-activated cell sorting (FACS) to enable separation of islet α-cell, β-cell and δ-cell when used in combination with a fluorescent exendin-4 peptide. Moreover, flow cytometry analysis of ZIGIR-2 labeled MIN-6 β cells revealed a wide variation in the granular $Zn^{2+}$ content from cell to cell. This facilitated the isolation of subsets of MIN6 cells containing distinct amounts of insulin granules by FACS after ZIGIR labeling. The success of developing ZIGIRs as a new class of specific, bright and sensitive sensors of granular $Zn^{2+}$ provides a powerful approach to analyze granular $Zn^{2+}$ and to study its regulation in living cells.

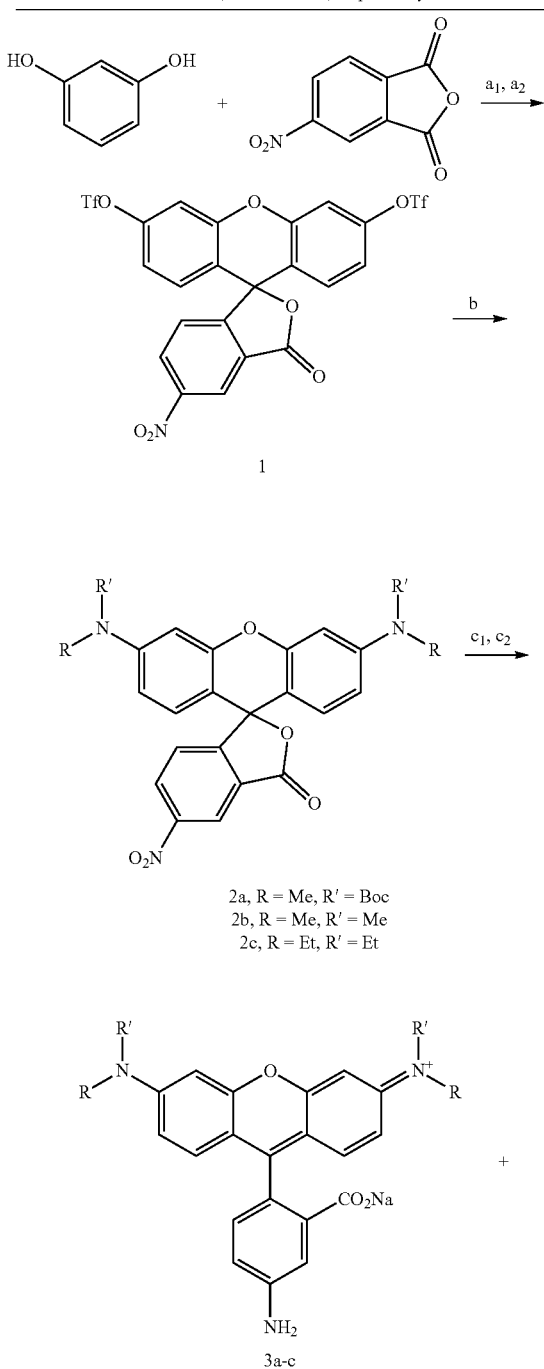

Scheme 1. Design and synthesis of ZIGIRs. (a1) $CH_3SO_3H$, 80° C., 10 h; (a2) $Tf_2O$, Pyridine, overnight, ~ 50% and 6-isomer. (b) $CH_3NHBoc$, or $Me_2NH\cdot HCl$, or $Et_2NH$ for 2a, 2b, and 2c, respectively, $Pd_2dba_3$ (0.1 equiv.), XPhos (0.3 equiv.), $Cs_2CO_3$ (2.8 equiv.), DME, 70° C.; 92%, 67%, and 52% yields for 2a, 2b, and 2c, respectively; (c1) $TFA/CH_2Cl_2$ (1:1), RT, overnight, quantitative (For 3a only); (c2) NaSH, $MeOH/H_2O$ (1:1), reflux, 1 h; 60%, 92% and 40% for 3a, 3b and 3c, respectively; (d) $NaBH_3CN$, $Na_2SO$, RT, overnight; 30%, 15%, and 17% for ZIGIR-1, ZIGIR-2, and ZIGIR-3, respectively.

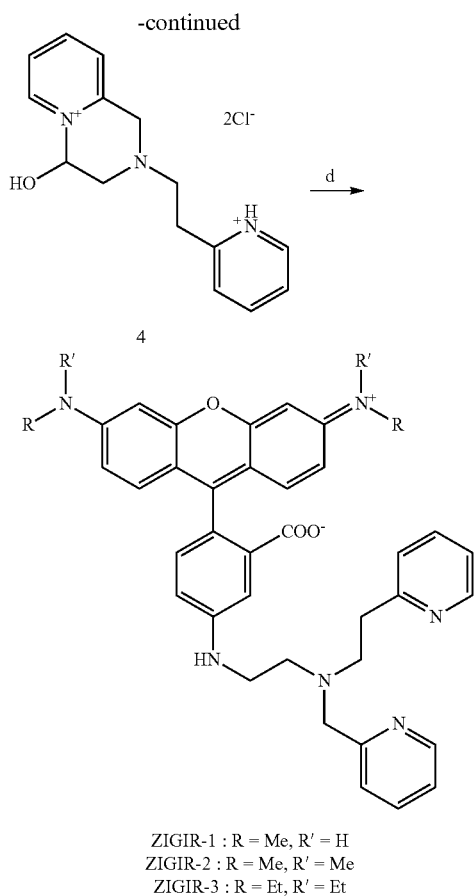

ZIGIR-1 : R = Me, R' = H
ZIGIR-2 : R = Me, R' = Me
ZIGIR-3 : R = Et, R' = Et

The lumen of secretory granules is normally acidic with an intraluminal pH of 5-6 (Stiernet et al., 2006 and De Young et al., 1987). To impart pH resistance to the granular $Zn^{2+}$ sensor, carboxyrhodamine was selected as the fluorophore. Fluorescence of carboxyrhodamine is insensitive to pH changes between 4 to 9. Moreover, compared to other commonly used fluorophores including fluorescein, rhodamine dyes are more photostable (Beija et al., 2009). In ZIGIRs, a $Zn^{2+}$ binding motif consisting of a 2-pyridylmethyl-[2-(2-pyridyl)ethyl]amine is linked to carboxyrhodamine through its 5-amino substituent (Scheme 1). Since $Zn^{2+}$-containing granules are known to have high $Zn^{2+}$ contents, and because $Zn^{2+}$ levels among other cellular compartments including the cytosol, nucleus, endoplasmic reticulum and mitochondrion are orders of magnitude lower, (Li, 2015, Chabosseau et al., 2018, and Hara et al., 2017) it was reasoned that $Zn^{2+}$ sensors with micromolar affinity would be appropriate for sensing $Zn^{2+}$ activity in $Zn^{2+}$-rich granules.

ZIGIR-1, ZIGIR-2, and ZIGIR-3 were synthesized from common starting materials in six steps (Scheme 1). ZIGIR-1 absorbed maximally near 520 nm, with a minimal bathochromic shift (4 nm) in its absorption maximum going from the $Zn^{2+}$-free to the $Zn^{2+}$-bound state (FIG. 1A). In contrast, ZIGIR-1 fluorescence intensity increased drastically when $[Zn^{2+}]$ was elevated (FIG. 1B). Overall the emission intensity increased 50-fold upon binding to $Zn^{2+}$, reaching a fluorescence quantum yield of 30%. Analysis of its $Zn^{2+}$ titration response by Hill plot yielded a $K_d(Zn^{2+})$ of 0.29 μM and a Hill coefficient of 0.99, confirming a 1:1 stoichiometry of $Zn^{2+}$ binding (FIG. 1C). To assess the sensitivity of ZIGIR-1 to physiological pH changes, $Zn^{2+}$ responsivity was compared at two pH values: pH 7.5 and pH 5.0. These pH values were chosen to mimic the neutral environment in the cytosol and the acidic milieu of the secretory granule, respectively. At both pH values, ZIGIR-1 displayed essentially the same fluorescence signal as long as the $Zn^{2+}$ level was kept the same (FIG. 1D).

Figures 2A, 2B, 2C, 2D, 2E:
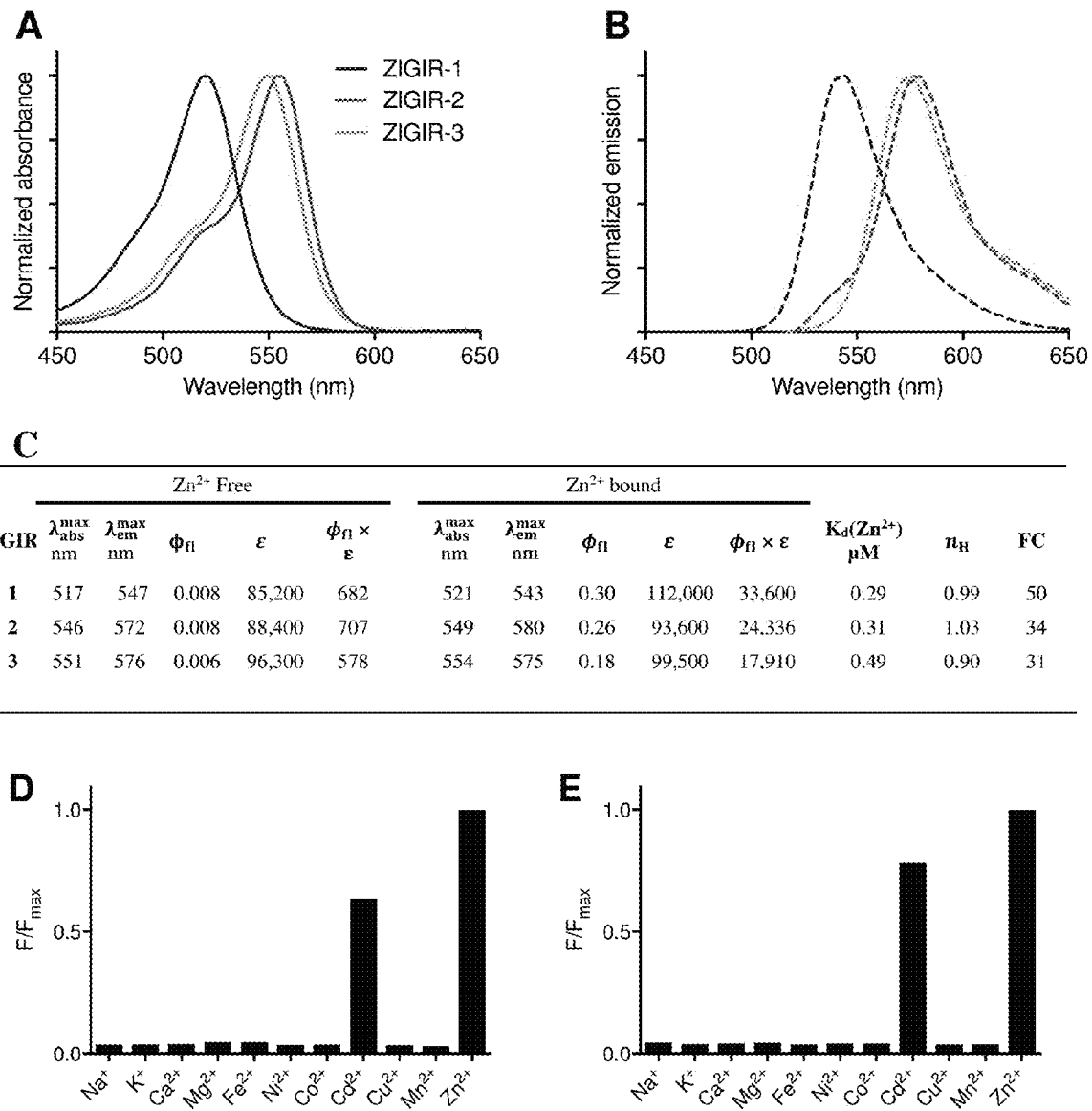
FIGS. 2A-2E show comparison of ZIGIRs.
Figures 3A, 3B, 3C, 3D:
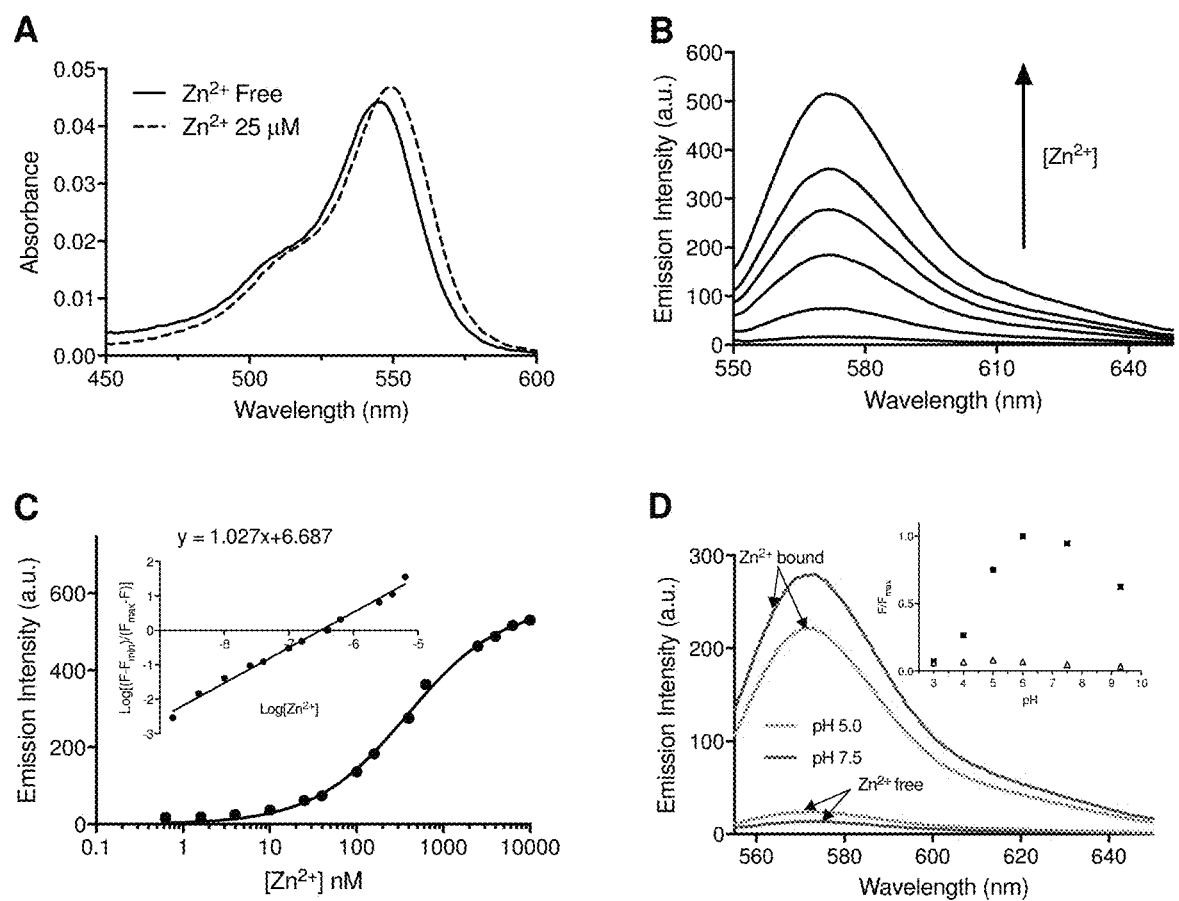
FIGS. 3A-3D show in vitro characterization of ZIGIR-2.
Figures 4A, 4B, 4C, 4D:
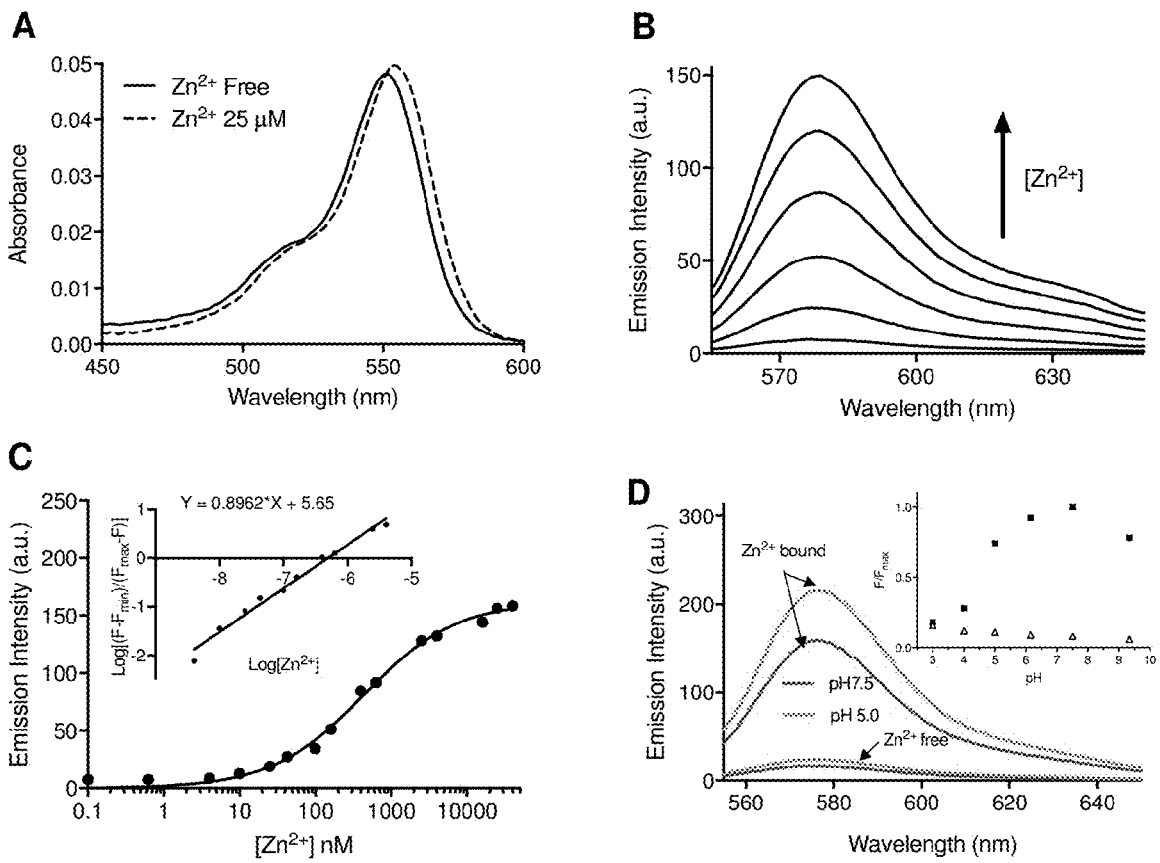
FIGS. 4A-4D show in vitro characterization of ZIGIR-3.
Figures 5A, 5B, 5C, 5D, 5E:
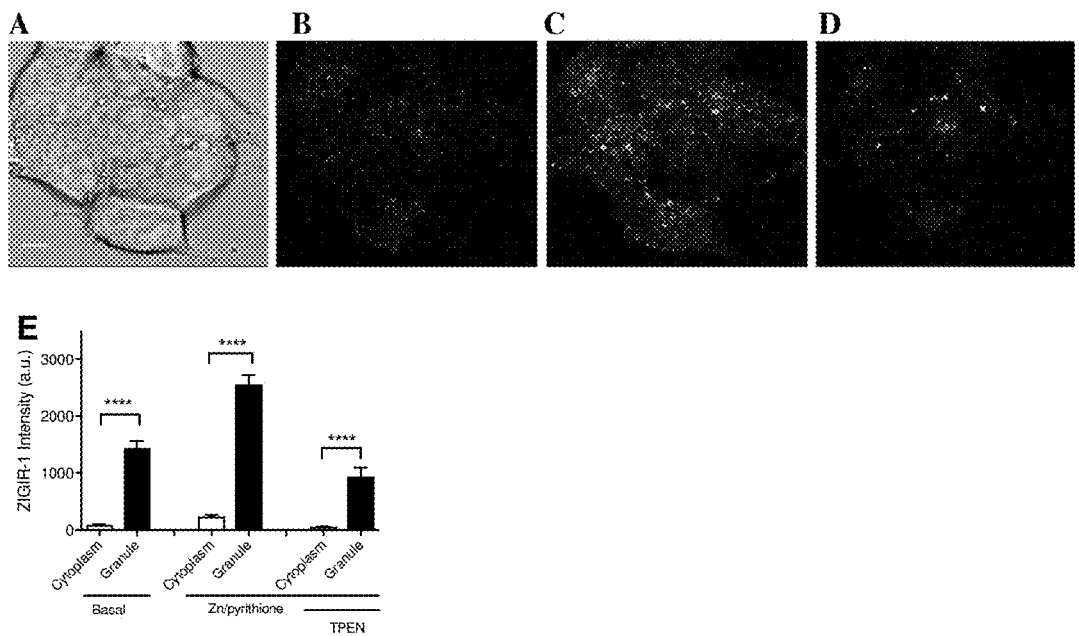
FIGS. 5A-5E show ZIGIR-1 imaging in live β cells. Differential interference contrast (DIC) image (FIG. 5A) and confocal fluorescence images (FIGS. 5B-5D) of INS-1 β cells labeled with ZIGIR-1. Cells were sequentially bathed in the basal SAB buffer, in SAB containing Zn/pyrithione (20 µM/10 µM), and in SAB containing Zn/pyrithione (20 µM/10 µM) and TPEN (25 µM). Scale bar=5 µm.

Expanding the pH titration from pH 3.0 to pH 9.3 revealed that fluorescence of ZIGIR-1 was largely refractor to pH changes from 5 to 8.5 (FIG. 1D, insert). When compared to ZIGIR-1, ZIGIR-2 and ZIGIR-3 exhibited red-shifted absorption and emission spectra, with maximum absorption and emission wavelengths centered around 555 nm and 580 nm, respectively (FIG. 2, FIG. 3, and FIG. 4). All three ZIGIRs showed similar $Zn^{2+}$ binding affinities and more than 30-fold fluorescence enhancement upon $Zn^{2+}$ complexation. Similar to ZIGIR-1, ZIGIR-2 and ZIGIR-3 photophysical properties are, to a large extent, independent of pH changes in the range of 5-7.5 (FIG. 3D and FIG. 4D), confirming that this family of probes is refractory to physiological pH fluctuation and maintains its $Zn^{2+}$ responsivity from neutral pH down to pH 5. In the $Zn^{2+}$-bound state, the fluorescence quantum yield of ZIGIR-3 was 18%, about 50% less than those of ZIGIR-1 and ZIGIR-2 (FIG. 2C). Thus, subsequent cell imaging studies focused primarily on ZIGIR-1 and ZIGIR-2. The fluorescence responses of ZIGIR-1 and ZIGIR-2 were selective for $Zn^{2+}$ against other ions including $Na^+$, $K^+$, $Ca^{2+}$, $Mg^{2+}$, $Fe^{2+}$, $Ni^{2+}$, $Co^{2+}$, $Cu^{2+}$ and $Mn^{2+}$ (FIGS. 2D & 2E). Among the metals tested, $Cd^{2+}$ was the only other ion besides $Zn^{2+}$ that was able to enhance ZIGIR intensity appreciably. Since the cellular $Cd^{2+}$ content is several orders of magnitude lower than the cellular $Zn^{2+}$ content (Wong et al., 2017), $Cd^{2+}$ is not expected to interfere with $Zn^{2+}$ sensing by ZIGIRs in cells.

While ZnAF-3 (Komatsu et al., 2005) contains a similar $Zn^{2+}$ binding motif as ZIGIRs and binds $Zn^{2+}$ with micromolar affinity (see Scheme 2 and Table 1 below), several important differences exist between these two classes of $Zn^{2+}$ sensors, and these differences endow ZIGIRs crucial advantages for imaging $Zn^{2+}$ activity in acidic secretory granules. First, ZnAF-3 is built on the fluorescein dye whose fluorescence intensity is quite sensitive to physiological pH fluctuations. At pH 6, fluorescence intensity of ZnAF-3 is only ~20% of that at neutral pH; while at pH 5, ZnAF-3 is practically non-fluorescent (Komatsu et al., 2005). In contrast, ZIGIRs maintain fairly constant fluorescence intensities form pH 5 to pH 8 (FIG. 1D). This puts ZIGIRs in a much better position for imaging $Zn^{2+}$ of acidic granules. Second, ZIGIRs enjoy more robust fluorescence enhancement upon $Zn^{2+}$ binding compared to ZnAF-3 (>30-fold vs 11-fold enhancement; see Table 1). This translates to larger dynamic range and lower background signal for live cell imaging. Third, ZIGIRs are cell membrane permeable and can enter cells and subcellular compartments by passive diffusion. ZnAF sensors, on the other hand, are membrane impermeable so they need to be converted into acetyl esters for cell loading and live cell imaging (Komatsu et al., 2005). Once inside cells, the acetyl ester is rapidly hydrolyzed by cellular esterases to regenerate ZnAF dyes which are trapped in the cytosol. This ester hydrolysis in the cytosol deters diffusion of ZnAF dyes across intracellular membranes and limits ZnAFs from entering membrane bound organelles including the secretory granule. Finally, ZIGIRs are acidotropic and accumulate in the acidic granules once inside cells (vide infra). This further enhances their selectivity and sensitivity for imaging $Zn^{2+}$ activity in the secretory granules.

Scheme 2.
Structural comparison of ZIGIR-1 and ZIGIR-2 to ZnAF-3 (Komatsu et al., 2005).

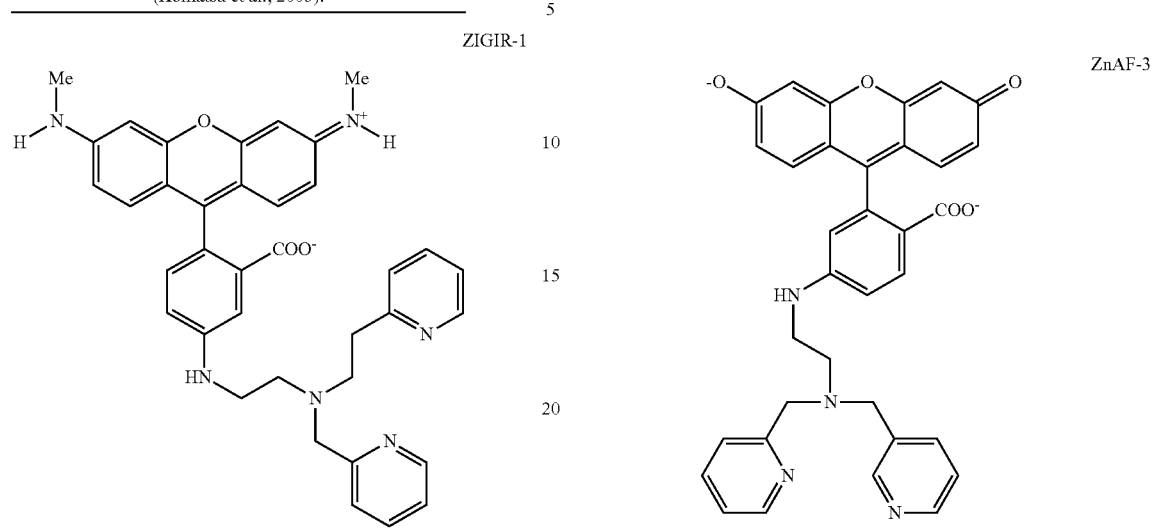

ZIGIR-1

ZnAF-3

TABLE 1

Photochemical properties of ZIGIRs and ZnAF-3. Data of ZnAF-3 is from (Komatsu et al., 2005)

| | Zn$^{2+}$ Free | | | | | Zn$^{2+}$ bound | | | | | | | |
|---|---|---|---|---|---|---|---|---|---|---|---|---|---|
| | $\lambda_{abd}^{max}$ nm | $\lambda_{em}^{max}$ nm | $\phi_{fl}$ | $\varepsilon$ | $\phi_{fl} \times \varepsilon$ | $\lambda_{abd}^{max}$ nm | $\lambda_{em}^{max}$ nm | $\phi_{fl}$ | $\varepsilon$ | $\phi_{fl} \times \varepsilon$ | $K_d(Zn^{2+})$ μM | $n_H$ | FC |
| ZIGIR-1 | 517 | 547 | 0.008 | 85,200 | 682 | 521 | 543 | 0.30 | 112,000 | 33,600 | 0.29 | 0.99 | 50 |
| ZIGIR-2 | 546 | 572 | 0.008 | 88,400 | 707 | 549 | 580 | 0.26 | 93,600 | 24,336 | 0.31 | 1.03 | 34 |
| ZnAF-3 | 490 | 514 | 0.029 | 71,000 | 2059 | 492 | 514 | 0.38 | 62,000 | 23,560 | 0.79 | 1 | 11 |

-continued

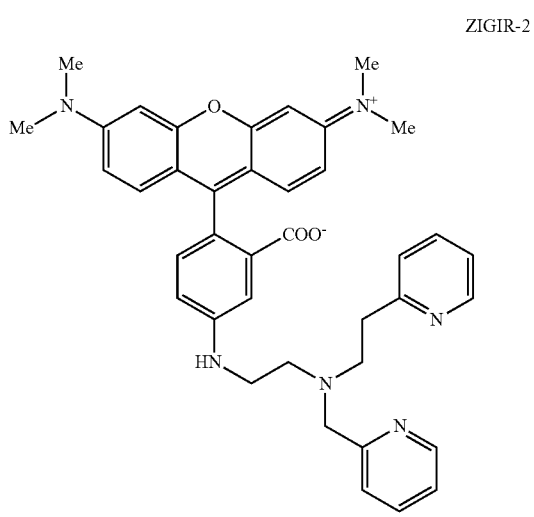

ZIGIR-2

B. ZIGIR Fluorescence Imaging in Living Cells

Figures 6A, 6B, 6C, 6D, 6E:
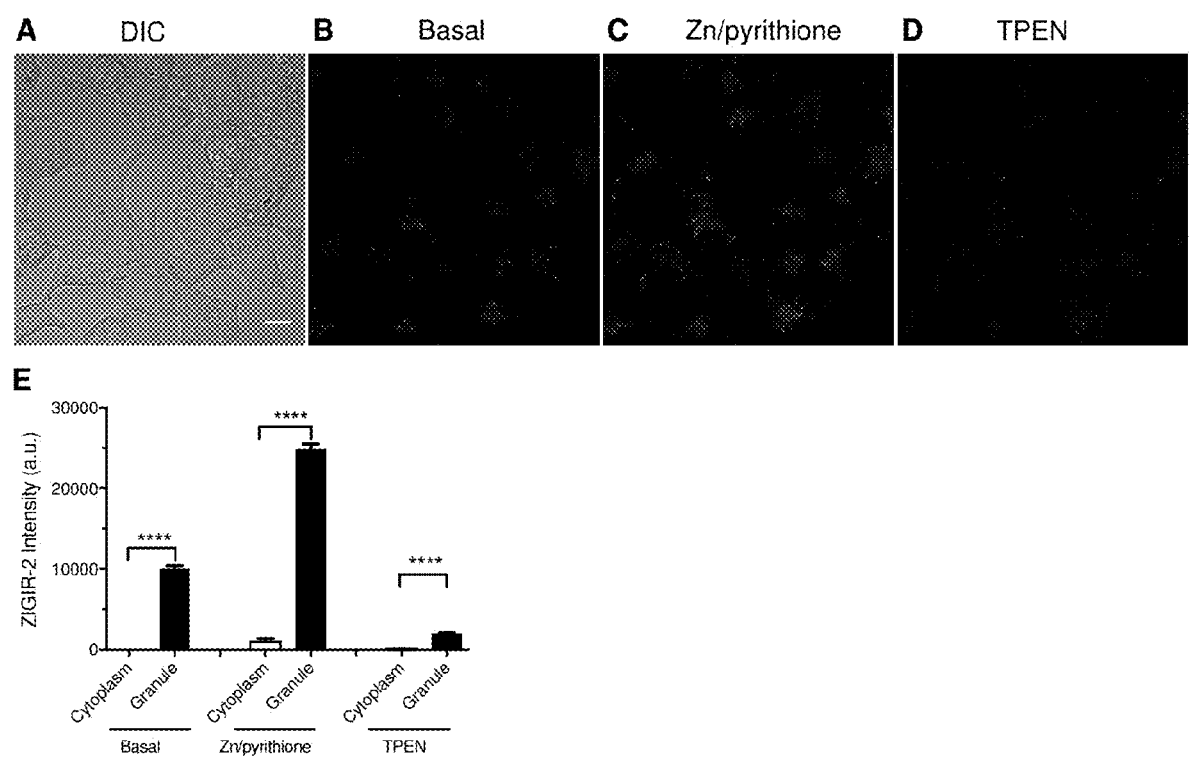
FIGS. 6A-6E show ZIGIR-2 imaging in live β cells. DIC image (FIG. 6A) and confocal fluorescence images (FIGS. 6B-6D) of MIN6 labeled with ZIGIR-2 (Ex 561 nm, Em 570-632 nm). Cells were sequentially bathed in the basal SAB buffer, in SAB containing Zn/pyrithione (20 µM/10

To assess ZIGIRs' ability for imaging granular Zn$^{2+}$ in living cells, an insulin secreting β cell (MIN-6 cell) was labeled with ZIGIRs. After dye loading (0.5 μM for 15 min) and washing, cells were imaged by confocal laser scanning microscopy (CLSM). In MIN-6 β cells, ZIGIR-2 labeling revealed numerous fluorescent puncta throughout the cytoplasm (FIG. 6A), consistent with the known abundance of Zn$^{2+}$-rich insulin granules in this cell line (Miyazaki et al., 1990). After raising cellular Zn$^{2+}$ level by adding a Zn$^{2+}$ ionophore (pyrithione, 10 μM) and Zn$^{2+}$ (20 μM), a drastic enhancement of ZIGIR-2 signal was observed. Zinc/pyrithione was expected to raise Zn$^{2+}$ levels throughout cells (Li, 2015 and Zalewski et al., 1991), yet it was found that the granular ZIGIR-2 signal still dominated the cellular fluorescence after global Zn$^{2+}$ elevation with zinc/pyrithione (FIGS. 6C & 6E), suggesting a selective enrichment of ZIGIR-2 in the granular compartments (vide infra). Subsequent washout of zinc/pyrithione and addition of a Zn$^{2+}$ chelator TPEN depleted cellular Zn$^{2+}$ activity and dampened ZIGIR-2 intensity to nearly the background level (FIGS. 6D & 6E). Overall ZIGIR-2 intensity increased about 12-fold going from the low Zn$^{2+}$ (TPEN) to the high Zn$^{2+}$ state (Zn$^{2+}$/pyrithione), with a cell-to-cell variation of 12.04±4.8 fold (mean±SD, N=20 cells). ZIGIR-1 imaging in β cells showed similar responses to zinc/pyrithione and TPEN (FIGS. 5A-E).

Figures 7A, 7B, 7C, 7D, 7E, 7F, 7G, 7H:
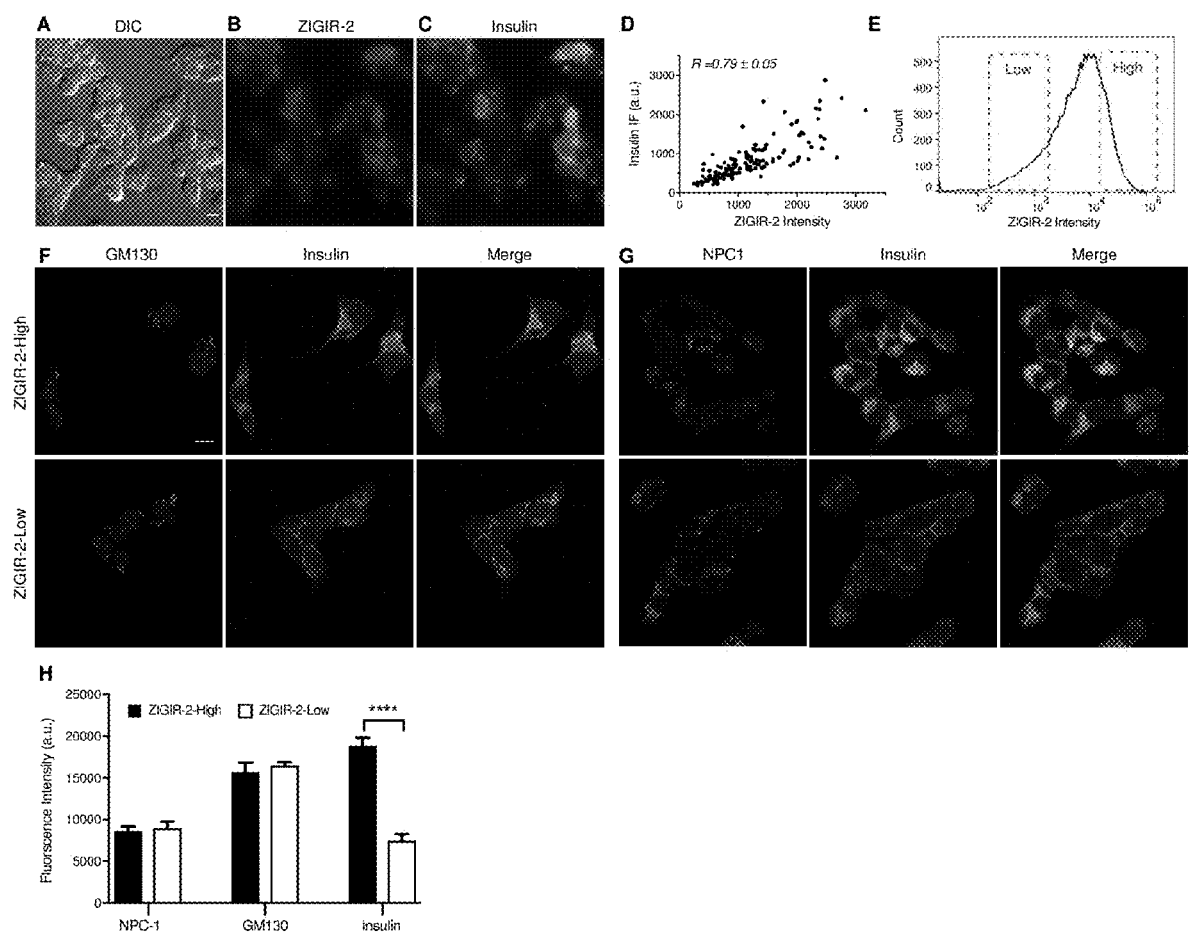
FIGS. 7A-7H show ZIGIR-2 labeling in β cells correlated with the insulin granule abundance.

Confocal imaging of ZIGIR-2 labeled MIN-6 cells appeared to be heterogenous, with numerous ZIGIR-2 positive puncta in some cells while few in others (FIG. 6B). The MIN-6 cell is a transformed β-cell line derived from a mouse insulinoma. This cell line has previously been suggested to consist of heterogenous β cells differing in their insulin level and glucose response (Minami et al., 2000 and Yamato et al., 2013). To investigate how ZIGIR-2 staining correlates with the distribution of insulin granules, insulin immunofluorescence was performed on the same MIN-6 cells after ZIGIR-2 imaging. Wide-field microscopy indicated that both ZIGIR-2 signal and insulin immunofluorescence varied over a wide range from cell to cell, yet ZIGIR-2 staining of individual MIN-6 cells showed a good correlation with the corresponding insulin signal (Pearson's R value=0.79±0.05, FIGS. 7A-7D), supporting that ZIGIR-2 labeled $Zn^{2+}$ rich insulin granules. To further analyze MIN-6 cells that were differentially labeled with ZIGIR-2, and to address whether ZIGIR-2 staining correlated with other cellular organelles, MIN6 cells were separated into ZIGIR-2-High and ZIGIR-2-Low subsets based on ZIGIR-2 fluorescence intensity using fluorescence-activated cell sorting (FACS; FIG. 7E). The sorted cells were then compared by immunofluorescence using antibodies against insulin, NPC-1 (a marker protein of late endosome/lysosome; Patel et al., 1999 and Higgins et al., 1999), or GM130 (a Golgi marker protein; Nakamura et al., 1995). Insulin immunofluorescence of ZIGIR-2-High cells was significantly higher than that of ZIGIR-2-Low cells. In contrast, immunofluorescence signals of NPC-1 and GM130 were comparable between the two cell subsets (FIGS. 7F-7H). The result confirmed that only insulin granule, but not Golgi or lysosome, correlated with ZIGIR-2 staining, further supporting the labelling specificity of ZIGIR-2 for the $Zn^{2+}$-rich secretory granule.

Figures 8A, 8B:
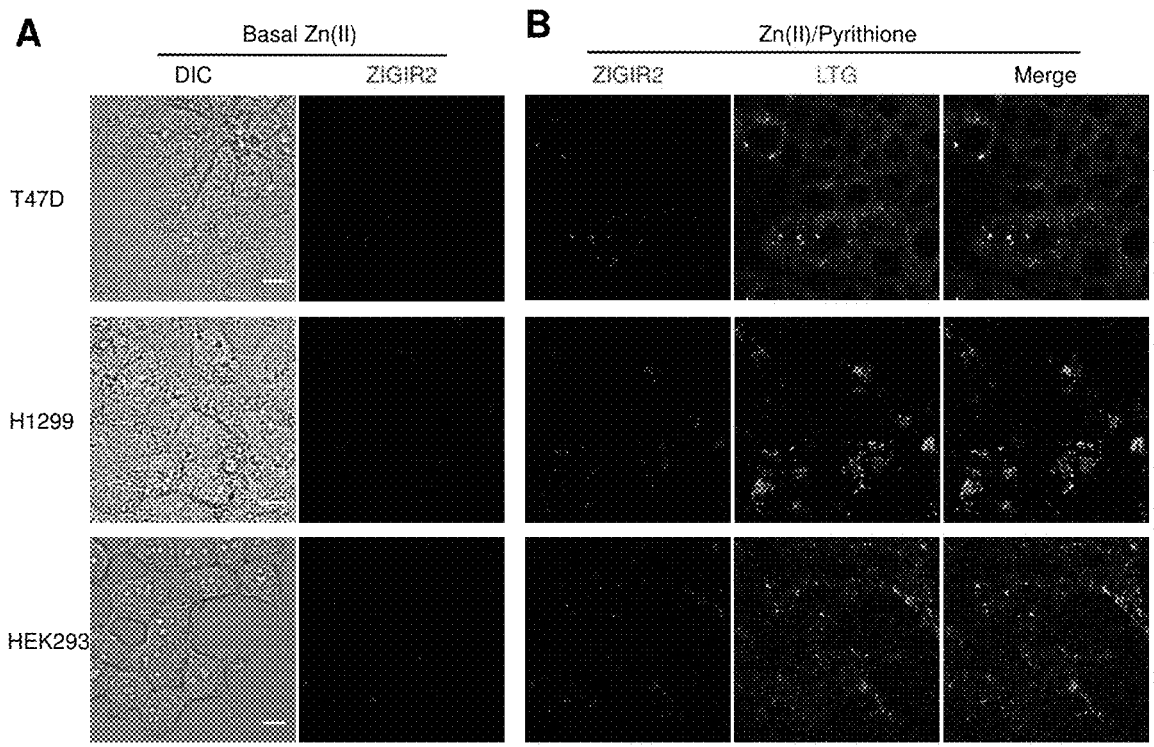
FIGS. 8A & 8B show ZIGIR-2 is enriched in acidic granules.

To better understand the granular labeling specificity of ZIGIR-2, a number of mammalian cells were imaged that are not known to contain $Zn^{2+}$ rich secretory granules. These included T47D human breast cancer cells, H1299 lung carcinoma and HEK293 human embryonic kidney cells. After loading ZIGIR-2 into these cells, barely any ZIGIR-2 fluorescence signal was detected under the same dye loading and imaging conditions as what were used for MIN6 cells (FIG. 8A, cf. FIG. 6B). However, after adding Zn/pyrithione, distinct ZIGIR-2 positive spots emerged in these cells (FIG. 8B). Subsequently, LysoTracker Green (LTG), an acidotropic fluorescent tracer based on BODIPY dye, was added to label acidic granules. Imaging of LTG revealed numerous intensely fluorescent dots in all three cell lines. Strikingly, the LTG-marked granules overlapped remarkably well with ZIGIR-2 positive puncta (FIG. 8B), confirming that ZIGIR-2 was also enriched in the acidic granules.

Similar to LTG, ZIGIRs are overall neutral and contain a weakly basic tertiary amine (Scheme 1). Small neutral molecules containing a weakly basic amine easily diffuse across the cell membrane and tend to accumulate in cellular compartments with low internal pH. Because of their micromolar $Zn^{2+}$ affinity, ZIGIRs that are enriched in the acidic compartments remain weakly or non-fluorescent unless $Zn^{2+}$ activity far exceeds nM. The combination of these properties endows ZIGIRs the selectivity and specificity required for imaging $Zn^{2+}$ activity of $Zn^{2+}$-rich secretory granules of living cells.

Figures 9A, 9B:
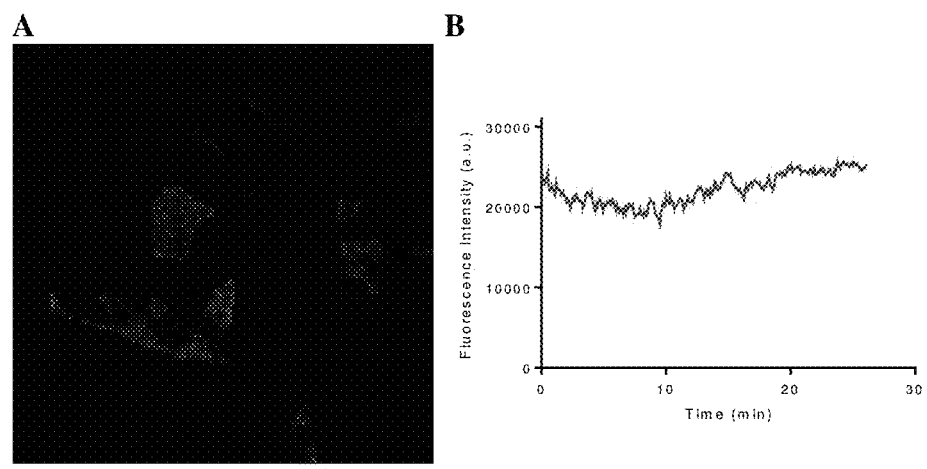
FIGS. 9A & 9B show intensity of ZIGIR-2 labeled granules remains stable after repetitive imaging.

Because individual ZIGIR-positive spots displayed distinct fluorescence well above the background signal of the bulk cytoplasm, individual granules were easily tracked inside cells. The stability of ZIGIR labeling facilitated following the dynamic behavior of marked granules by time-lapse imaging. Confocal images of ZIGIR-2 or ZIGIR-1 were acquired every 5 seconds over tens of minutes in MIN6 cells. The imaging revealed highly dynamic movements of numerous ZIGIR-labeled granules in the cytosol and along the subplasmalemmal area. Over the course of fluorescence imaging, the intensity of ZIGIR labeled granules remained stable and bright (FIG. 9), demonstrating satisfactory photo-stability of ZIGIRs for cellular imaging.

Figures 10A, 10B, 10C, 10D, 10E:
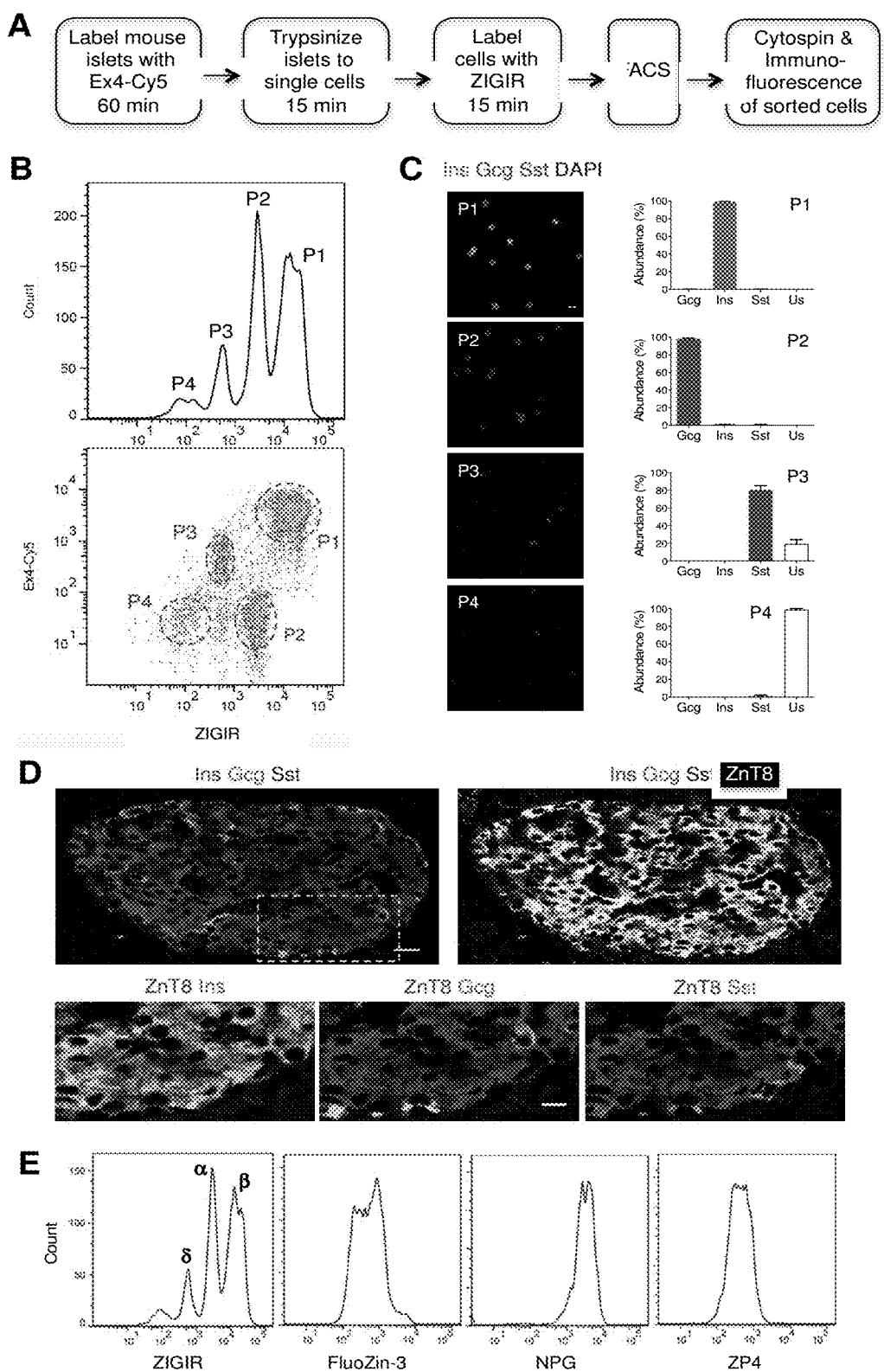
FIGS. 10A-10E show flow cytometry analysis of granular $Zn^{2+}$ activity and sorting mouse islet cells with ZIGIR-2.

C. Analyzing Granular $Zn^{2+}$ Activity and Sorting Mouse Islet Endocrine Cells Among islet endocrine cells, β-cells have long been known to contain a high level of total $Zn^{2+}$ in their secretory granules. However, it remains unclear how $Zn^{2+}$ activities differ among different types of secretory granules including the glucagon granule and the somatostatin granule. To address the question, the inventors combined ZIGIR-2 and flow cytometry to analyze the granular $Zn^{2+}$ activity in primary mouse islet cells. To facilitate distinguishing different endocrine cells, they labeled mouse islets with a β-cell marker, a Cy5 dye conjugate of Exendin-4 peptide (Ex4) (Scheme 3). Ex4 is a high affinity ligand of the glucagon like peptide 1 receptor (GLP-1R). Since GLP-1R is highly expressed in mouse islet β-cells,[46] fluorescently labeled conjugates of Ex4 are rapidly internalized into β-cells through receptor-mediated endocytosis to mark β-cells.[36, 47] After labeling mouse islets with Ex4-Cy5, the inventors dispersed the islets into single cells and labeled them with ZIGIR-2 (FIG. 10A). Flow cytometry analysis of the labeled islet cells revealed four distinct subsets of cells, P1-P4, on the two-dimension scatter plot (FIG. 10B). To identify each subset of cells, the inventors isolated them by FACS and analyzed the sorted cells by immunofluorescence using antibodies against insulin, glucagon, and somatostatin. The immunofluorescence result confirmed that P1 and P2 subsets were essentially pure β-cells (99±0.3%, N=3) and α-cells (98±0.5%, N=3), respectively (FIG. 10C). The P1 subset showed the highest level of Ex4-Cy5 and ZIGIR-2 signal, consistent with the abundant GLP-1R expression on the β-cell and high $Zn^{2+}$ content in the insulin granule. The P3 subset was highly enriched with δ-cells (81±4.8%, N=3) and exhibited ZIGIR-2 signal lower than both P1 and P2. The remaining ~20% of cells in P3 and most cells in P4 were not stained by any of the three hormone antibodies. These cells likely represented rare β cell, islet endothelial cells or lymphoid cells, and residual exocrine cells.

Scheme 3.
Synthesis of Ex4-Cy5. A cysteine residue was introduced to the C-terminus of Ex4 for conjugation with Cy5-maleimide.
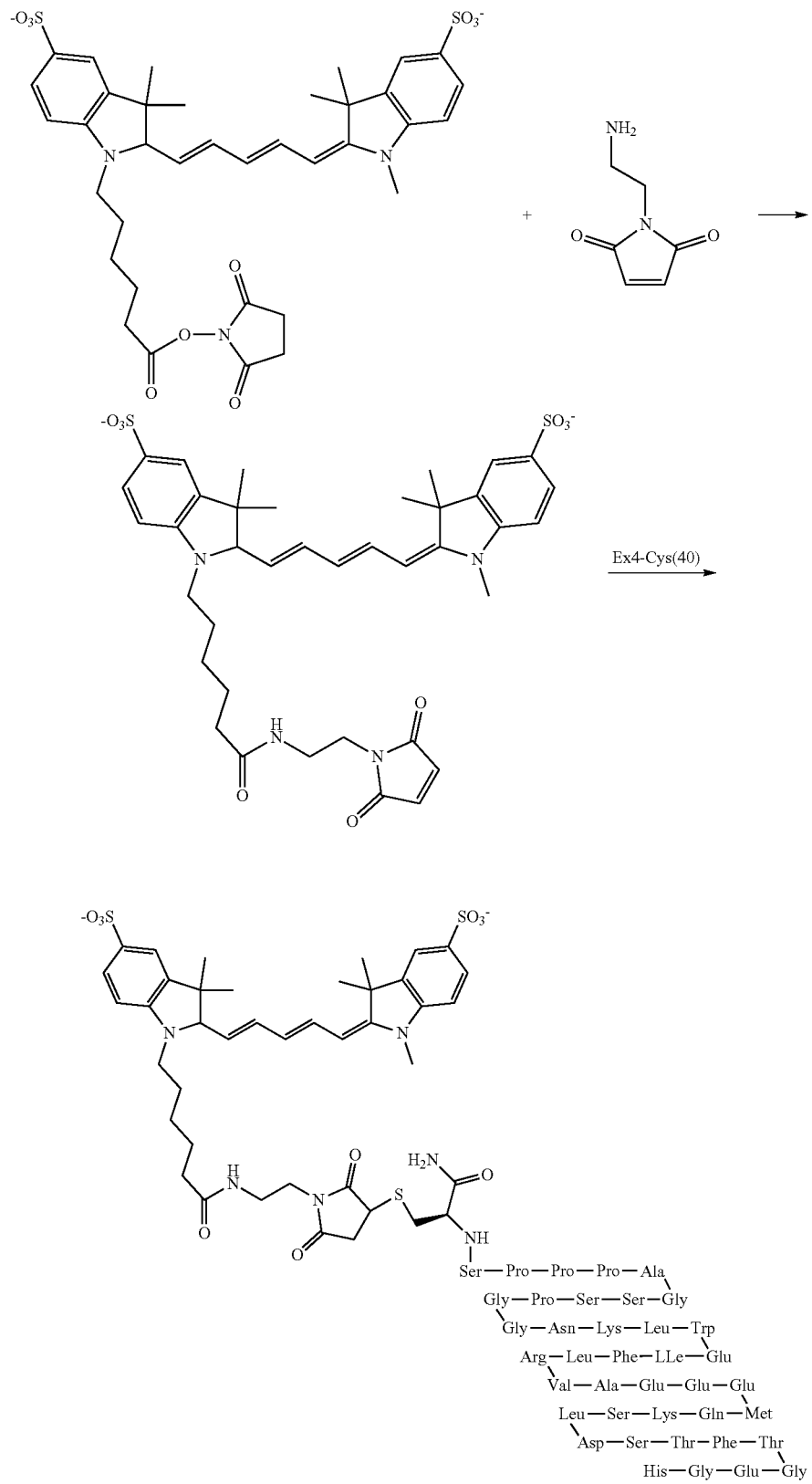

To the inventors' knowledge, this flow cytometry analysis of cellular ZIGIR-2 signal represented the first systematic effort to compare $Zn^{2+}$ activity among three types of secretory granules of islet cells. The result showed that the median fluorescence intensity (MFI) of ZIGIR-2 in α-cells was nearly an order of magnitude stronger than that of δ-cells but was about 5 times weaker than that of β-cells (FIG. 10B). This confirmed the very high $Zn^{2+}$ activity in the insulin granule and suggested an appreciable amount of free $Zn^{2+}$ in the glucagon granule that was substantially higher than that of the somatostatin granule. These results are in line with the pattern of ZnT8 expression in mouse islet cells. ZnT8 is selectively expressed in pancreatic islets and is the major transporter responsible for importing $Zn^{2+}$ into the dense core granules (Davidson et al., 2014). Consistent with the earlier reports (Murgia et al., 2009; Artner et al., 2010; Solomou et al., 2015), immunofluorescence of ZnT8 in mouse pancreatic sections confirmed ZnT8 expression in both α-cells and β-cells but not δ-cells (FIG. 10D). This provided a molecular basis to account for the low $Zn^{2+}$ level in the somatostatin granule as measured by ZIGIR-2. Besides ZnT8 expression, another factor that could contribute to the very high $Zn^{2+}$ activity of the insulin granule is the $Zn^{2+}$ chelating property of insulin[3]. The high abundance of insulin in the secretory granule of the β-cell effectively turns the lumen of the insulin granule into a high capacity $Zn^{2+}$ sponge.

Fluorescent $Zn^{2+}$ indicators that have been previously reported for imaging granular $Zn^{2+}$ activity include FluoZin-3/AM (Gee et al., 2002, McCormick et al., 2010, and Jayaraman, 2008), Newport Green (Lukowiak et al., 2001), ZP dyes (Burdette et al., 2003, Solomou et al., 2015, and Burdette et al., 2001), ZincBY-1 (Que et al., 2015), and SpiroZin2 (Rivera-Fuentes et al., 2015). ZIGIR-2 was compared with several commercially available $Zn^{2+}$ sensors by flow cytometry in mouse islet cells. Only ZIGIR-2, but not other $Zn^{2+}$ sensors, was able to resolve islet cells into distinct subsets according to their granular $Zn^{2+}$ activity (FIG. 10D), demonstrating the superior sensitivity, specificity and dynamic range of ZIGIR-2 as a granular $Zn^{2+}$ probe. The enhanced performance of ZIGIRs in tracking granular $Zn^{2+}$ activity and resolving different types of secretory granules may be attributed to their unique combination of properties including large dynamic range of $Zn^{2+}$ response (>30-fold), low $Zn^{2+}$ affinity in the micromolar range, acidiophilicity in cells, and pH resistance. More detailed comparisons of a ZIGIR probe with previously reported $Zn^{2+}$ sensors (Gee et al., 2002, Burdette et al., 2003, and Rivera-Fuentes et al., 2015), including several pH insensitive ones (Que et al., 2015, Wu et al., 2005, and Taki et al., 2004), are shown in Table 2.

TABLE 2

Comparison of $Zn^{2+}$ sensors.

| Sensor | BDA | FluoZin-3 | ZP-4 | ZincBY-1 |
|---|---|---|---|---|
| Structure | (structure) | (structure) | (structure) | (structure) |
| $K_d(Zn^{2+})$ | 1 nM | 15 nM | 0.65 nM | 2.5 nM |
| $Zn^{2+}$ response (fold change) | 6× | >100× | 44× | 4.6× |

TABLE 2-continued

Comparison of Zn²⁺ sensors.

| Sensor | ZINbo-5 | SpiroZin2 | ZIGIR-2 |
|---|---|---|---|
| Structure | 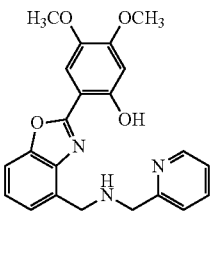 [SMILES: COc1cc(O)c(-c2nc3c(CNCc4ccccn4)cccc3o2)cc1OC] | 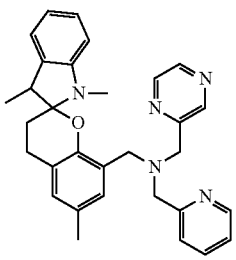 [SMILES: Cc1cc2c(c(CN(Cc3ccccn3)Cc3cnccn3)c1)OC1(CC2)C(C)c2ccccc2N1C] | 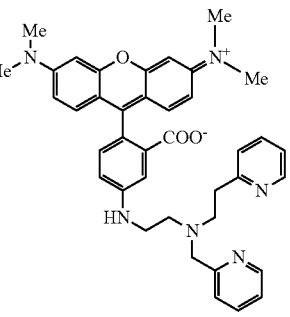 |
| $K_d(Zn^{2+})$ | 2.2 nM | 3.6 nM | 810 nM |
| $Zn^{2+}$ response (fold change) | NA (ratiometric) | 8× | 34× |

Combining ZIGIR-2 and Ex4-Cy5, a simple one-step procedure of sorting mouse islet α-cell, β-cell and δ-cell simultaneously was developed (FIG. 10A). This new technique may greatly facilitate isolating primary islet endocrine cells for in depth functional and molecular analyses. Previous methods for separating islet endocrine cells largely relied on genetic approaches by expressing fluorescent proteins under the control of cell specific promoters such as the insulin promoter, preproglucagon promoter, or somatostatin promoter (Hara et al., 2003, Quoix et al., 2007, Egerod et al., 2015).

Such methods, however, only allow labeling one cell type at a time and are further limited by the incomplete cell labeling due to the partial penetrance of the artificial transgene expression. To label and sort more than one types of islet endocrine cells at once, the previous genetic approach would require generating double or triple transgenic mice by expressing different fluorescent proteins in separate classes of endocrine cells. Breeding such mice is cumbersome especially when the studies need to be carried out in a background of genetic mutations. In contrast, the present disclosure provides methods of islet cell labeling and sorting by ZIGIR-2 and Ex4-Cy5 yielded highly enriched α-cell, β-cell and δ-cell in one step. The procedure is rapid, non-invasive, and should be applicable to both wild type and mutant mice.

D. Analyzing and Sorting Human Islet Endocrine Cells with ZIGIR-2

Figure 13:
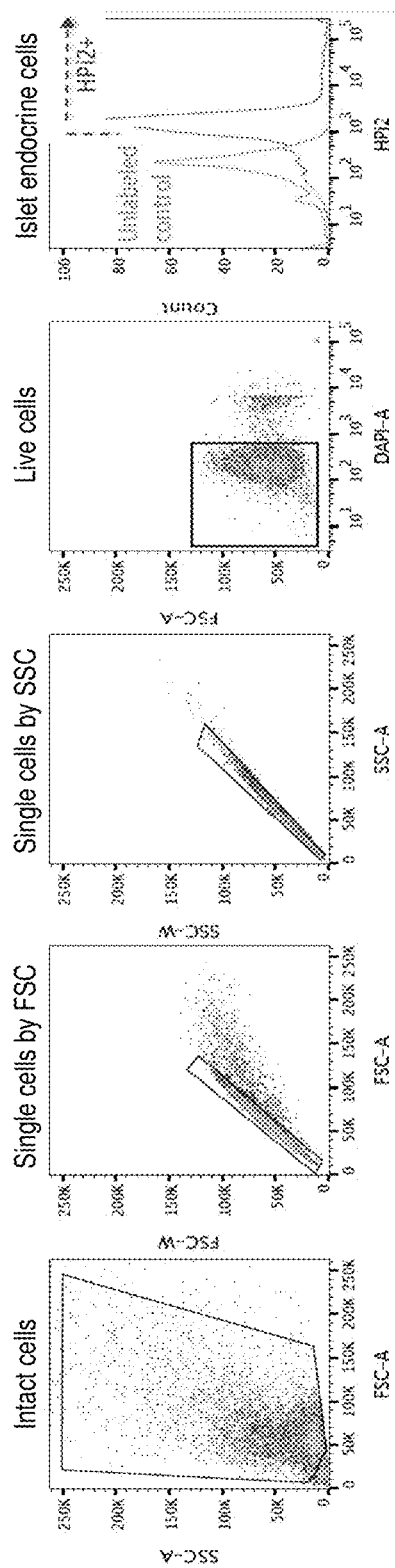
FIG. 13. Flow cytometry analysis and gating strategy of human islet cells labeled with DAPI, FAB7998G (anti-TM4SF4-AF488), ZIGIR-2, and HPi2-APC. The gated population was labeled above each flow plot: Intact cells were separated from cell debris by forward scatter (FSC) and side scatter (SSC); single cells were gated by the shape of electronic pulse (FSC-A vs. FSC-W; and SSC-A vs. SSC-W); live cells were separated from dead cells by DAPI staining; and endocrine cells were identified by their positive staining for HPi2. The unlabeled control cell of the same donor was used to define the threshold for HPi2 positivity.
Figure 14F:
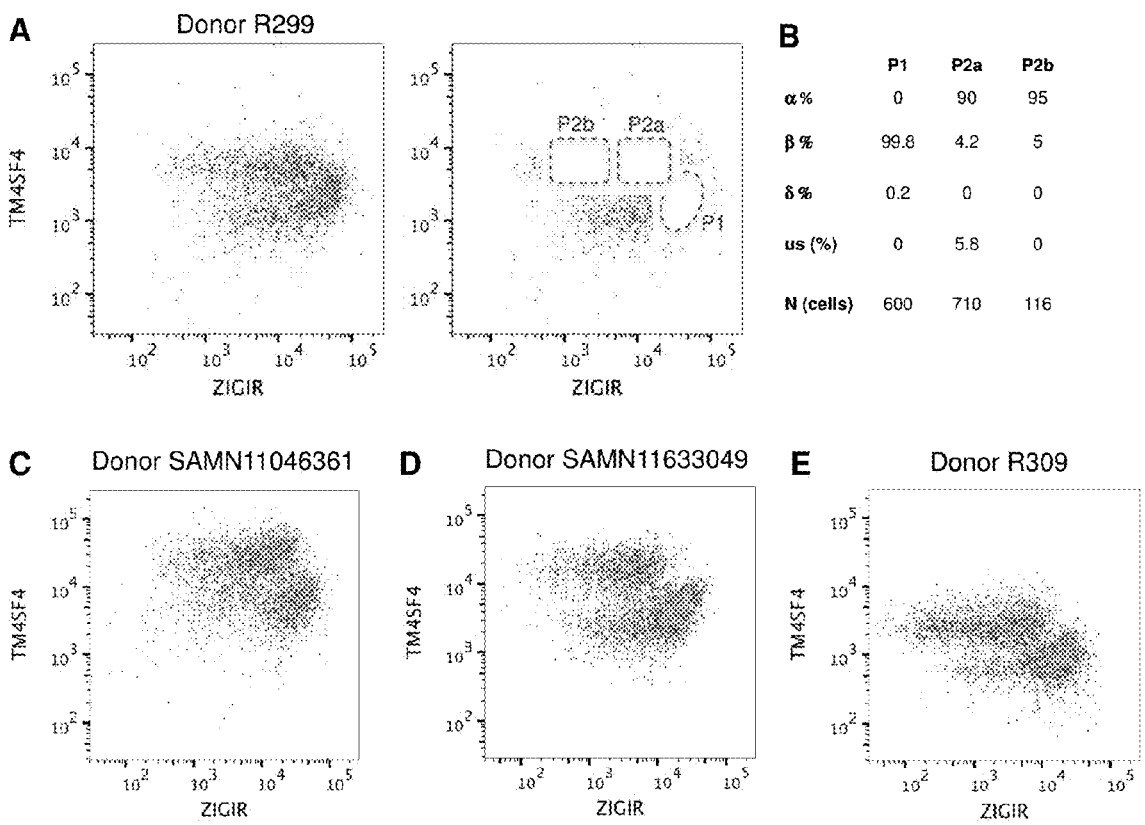

Thus far the majority of studies on ZnT8 and $Zn^{2+}$ signaling have been carried out in mouse islet cells, and less is known about the expression of ZnT8 and $Zn^{2+}$ distribution in human islet endocrine cells. To analyze granular $Zn^{2+}$ activity in human islets by flow cytometry, the inventors dispersed human islets into single cells and sequentially labeled them with ZIGIR-2 and antibodies reactive towards human pancreatic endocrine cells and α-cells (FIG. 12A), including the HPi2 antibody (Dorrell et al., 2008) and an antibody of a tetraspanin family member protein TM4SF4 (Muraro et al., 2016), respectively. The islet endocrine cells (HPi2+, FIG. 13) contained a subset of cells showing high ZIGIR-2 signal and low TM4SF4 expression (P1 subset, FIG. 12B). Immunofluorescence analysis of the sorted cells confirmed that the P1 subset was highly enriched with human β-cells (91%), together with a small percent of δ-cells (FIG. 12C). The majority of remaining cells displayed a high TM4SF4 expression and a wide spread of ZIGIR-2 signal. The inventors divided them into two subsets, P2a and P2b, that showed high or low ZIGIR-2 signal, respectively (FIG. 12B). Interestingly, both P2a and P2b subsets consisted α-cells of high purity (>95%), consistent with the reported abundant expression of TM4SF4 in human α-cells (Muraro et al., 2016). They obtained similar flow cytometry results from different human donors and confirmed high enrichments of β-cell or α-cell in P1 or P2 subset (including P2a and P2b), respectively (FIG. 14). The distinct ZIGIR-2 signals of P2a and P2b α-cells suggested varied glucagon granule abundances, or different $Zn^{2+}$ activities in the glucagon granule, or both. To examine these possibilities, the inventors quantified glucagon immunofluorescence intensities of these two subsets of α-cells and found that the glucagon signal of P2a was about four times as high as that of P2b α-cells (FIGS. 12D-E), confirming a substantially higher glucagon content in P2a cells that corroborated with their stronger ZIGIR-2 staining. In addition to containing more glucagon granules, P2a cells might also express more ZnT8 protein than P2b. Future studies using more quantitative techniques such as western blot should help address the issue. Regardless the exact mechanism underlying the broad distribution of ZIGIR-2 labeling of human α-cells, the inventors observed this phenomenon repeatedly in isolated islets from various human donors (FIGS. 12A-E and FIG. 14), suggesting a general phenomenon of human α-cell heterogeneity defined by their distinct glucagon contents.

Figure 15:
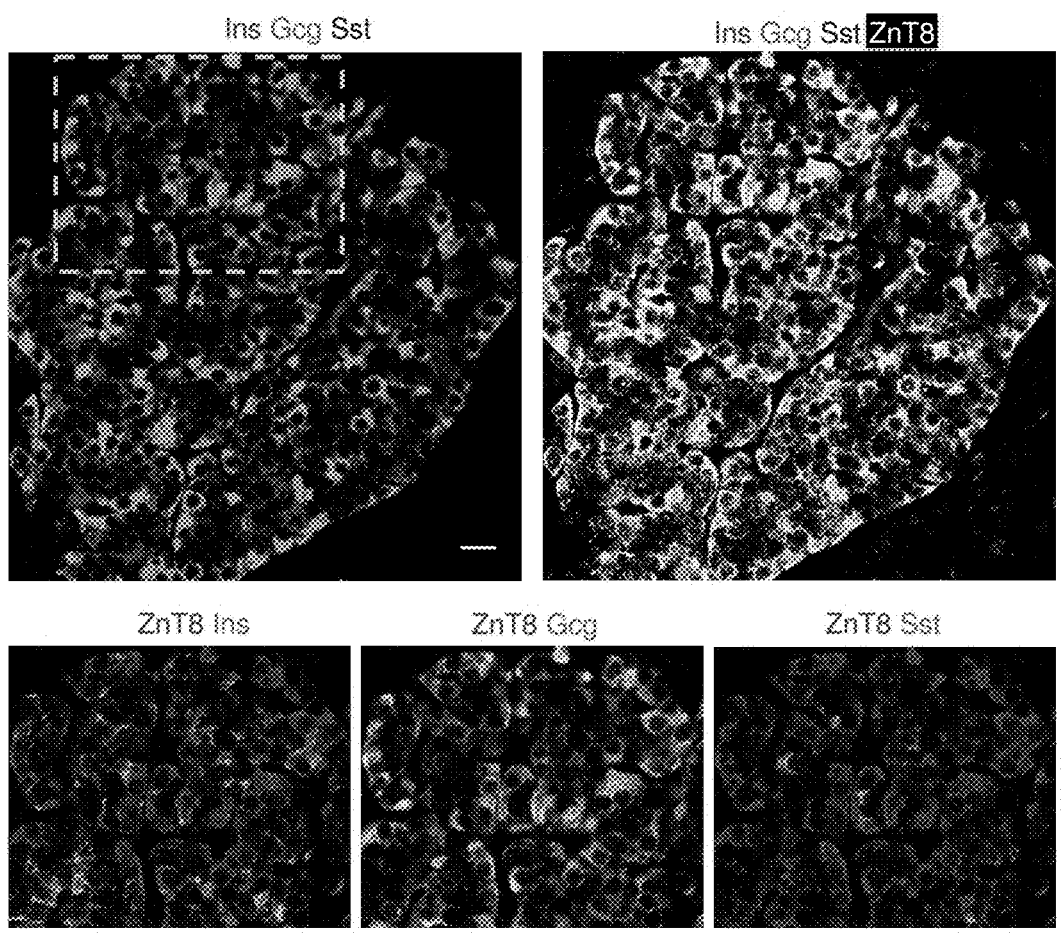
FIG. 15. ZnT8 is expressed in three major endocrine cells of human pancreatic islets. Confocal immunofluorescence images of a human pancreas section stained with antibodies against three islet hormones and ZnT8. The enlarged images of the area highlighted by the dashed box are shown at the bottom row, with ZnT8 pseudo-colored in red and individual hormones in green to aid visualization of the expression overlap.

Besides α-cell heterogeneity, flow cytometry analysis of ZIGIR-2 labeling revealed another major difference between human and mouse islet cells. In contrast to the mouse islet δ-cell that showed very low ZIGIR-2 signal (FIG. 10B, 10C), the human δ-cell displayed strong ZIGIR-2 staining that was comparable to the human β-cell (FIGS. 12B-C and FIGS. 14A-B), suggesting a high $Zn^{2+}$ activity in the human somatostatin granule. To investigate the molecular basis for this phenomenon, the inventors examined ZnT8 expression in human islets by multi-color immunofluorescence and found that ZnT8 was expressed in all three major islet endocrine cells including the δ-cell (FIG. 15). The expression pattern of ZnT8 protein in human islet cells was consistent with the published RNA-Seq data documenting abundant expression of SLC30A8 gene in human α-cell, β-cell, δ-cell and β cell (Segerstolpe et al., 2016), and accounted for the strong ZIGIR-2 signal and high granular $Zn^{2+}$ activity in the human δ-cell.

In recent years, there have been increasing interests in engineering β-cells from embryonic stem cells or induced pluripotent stem cells (Ellis et al., 2017). If successful, such engineered β-cells may offer a solution to overcome the bottleneck of cell replacement therapy of type 1 diabetes, namely the very limited supply of human islets from organ donors. The process of such β-cell engineering generally involves expansion and induced differentiation of stem cells in vitro. The differentiated cells are considered to adopt a β-cell-like fate once a stable insulin expression is confirmed. Since studies of this sort were carried out in cell populations, the differentiated cells represented a heterogenous mixture of cells expressing insulin spanning a wide range, and the average insulin content of such engineered β-like cells or immortalized β-cells was typically well below that of the primary islet β-cells (Ravassard et al., 2011). To facilitate β-cell engineering using stem cells and to isolate cell clones containing abundant insulin granules, it would be desirable to screen the insulin content in single living cells.

Currently, the only methods for assaying the cellular insulin content are to perform insulin immunofluorescence or traditional ELISA assay. Both methods, however, compromise cell viability. ZIGIRs, in contrast, are developed for live cell imaging and serve as a good surrogate marker of insulin granules (FIG. 7). Heterogenous MIN-6 β cells may be sorted according to ZIGIR-2 labeling to yield cell populations containing either high or low insulin. Analysis and comparison of these sorted cells may offer mechanistic insights on the regulation of insulin gene expression and biogenesis of dense core secretory granules in β-cells.

Example 2: Materials and Methods

A. Chemical Synthesis of ZIGIRs

All reagents were purchased from Aldrich or VWR. Anhydrous solvents were stored over activated molecular sieves (3 Å or 4 Å). TLC was performed on precoated silica gel 60F-254 glass plates (EM Science). Reaction products were purified by low-pressure flash chromatography (FC) using silica gel 60 (63-200 μm; EM Science). $^1$H-NMR spectra were acquired on a Varian 400-MHz or 500-MHz spectrometer. Chemical shifts (δ, ppm) were reported against tetramethylsilane (0 ppm). MALDI-TOF MS was performed on a Voyager-DE PRO biospectrometry workstation (Applied Biosystems) using 2,5-dihydroxy benzoic acid as the matrix.

5-Nitro-3-oxo-3H-spiro[isobenzofuran-1,9'-xanthene]-3',6'-diyl bis(trifluoromethanesulfonate) (1)

4-Nitrophthalic acid anhydride (0.97 g, 5.0 mmol) and resorcinol (1.30 g, 11.8 mmol) were dissolved in 100 mL of methanesulfonic acid. The mixture was stirred at 80° C. for 12 h. After cooling, the reaction was quenched in 100 mL of ice water and the mixture was filtered through a sintered glass filter. The retentate was dried under vacuum at 50° C. for 8 h. The resulting dark red solid was then suspended in anhydrous pyridine (20 mL). $Tf_2O$ (2.2 equiv.) was added dropwise at 0° C. The reaction mixture was stirred at room temperature (r.t.) until the complete consumption of the starting material. Pyridine was evaporated under a reduced pressure and the crude residue was suspended in $CHCl_3$ (50 mL) and washed with saturated NaCl. The organic layer was dried over $Na_2SO_4$, and the concentrated crude product was purified by FC (hexane/EtOAc, 9:1→2:1) to provide the product (0.676 g, 21.1%), the 6-nitro isomer (0.632 g, 19.7%), and the mixture of both 5- and 6-isomers (0.295 g, 9.2%) as white solids. $^1$H NMR (400 MHz, DMSO-$d_6$) δ 8.75 (d, J=2.1 Hz, 1H), 8.63 (dd, J=8.6, 2.1 Hz, 1H), 7.86 (d, J=8.4 Hz, 1H), 7.81 (d, J=2.4 Hz, 2H), 7.34 (dd, J=8.8, 2.5 Hz, 3H), 7.26 (d, J=8.9 Hz, 3H). MS: $[M+H]^+$ calcd for $C_{22}H_{10}F_6NO_{11}S_2^+$ 641.96; found: 642.27.

Di-tert-butyl (5-nitro-3-oxo-3H-spiro[isobenzofuran-1,9'-xanthene]-3',6'-diyl)bismethylcarbamate (2a Under argon atmosphere, compound 1 (64.2 mg, 0.1 mmol), tert-butyl methylcarbamate (31.5 mg, 0.24 mmol), $Pd_2dba_3$ (9 mg, 0.1 equiv.), XPhos (14.3 mg, 0.3 equiv.) and $Cs_2CO_3$ (91.3 mg, 0.28 mmol) were dissolved in anhydrous dimethoxyethane. The resulting mixture was heated at 70° C. overnight and concentrated to a dark oil. The mixture was purified by FC (hexane/EtOAc, 6:1→2:1) to afford the target compound as white crystals (55.5 mg, 92%). $^1$H NMR ($CDCl_3$, 400 MHz): δ 8.83 (d, J=2.0 Hz, 1H), 8.48 (dd, J=2.4, 8.8 Hz, 1H), 7.33 (d, J=8.4 Hz, 1H), 7.25 (d, J=2.0 Hz, 2H), 7.00 (dd, J=2.4, 8.4 Hz, 2H), 6.70 (d, J=9.2 Hz, 2H), 3.27 (s, 6H), 1.46 (s, 18H). MS: $[M+H]^+$ calcd for $C_{32}H_{34}N_3O_9^+$ 604.2290; found: 604.0330.

2-(6-(Dimethylamino)-3-(dimethyliminio)-3H-xanthen-9-yl)-5-nitrobenzoate (2b

DME (1.5 mL) was added to a mixture of compound 1 (100 mg, 0.16 mmol), $Me_2NH$—HCl (40 mg, 0.47 mmol), $Pd_2dpa_3$ (30 mg, 0.03 mmol), XPhos (38 mg, 0.08 mmol) and $Cs_2CO_3$ (300 mg, 0.96 mmol) in a pressure tube. The tube was degassed and purged with Argon three times. The tube was then sealed and heated at 70° C. for 18 h. After cooling, the mixture was diluted with MeOH and silica (~1 g) was added to the mixture. The dried mixture was then purified by FC using a gradient of 5→15% MeOH in DCM to afford the product as a purple solid (45 mg, 67%). $^1$H NMR ($CD_3OD$, 400 MHz) δ 8.97 (d, J=1.9 Hz, 1H), 8.48 (dd, J=8.3, 2.0 Hz, 1H), 7.56 (d, J=8.3 Hz, 1H), 7.19 (d, J=9.5 Hz, 2H), 7.07-7.00 (m, 2H), 6.96 (d, J=2.4 Hz, 2H), 3.29 (s, 12H). MS: $[M+H]^+$ calcd for $C_{24}H_{22}N_3O_5$ 432.1554; found: 432.6610.

2-(6-(Diethylamino)-3-(diethyliminio)-3H-xanthen-9-yl)-5-nitrobenzoate (2c

Compound 2c was synthesized similarly as 2b in 52% yield. $^1$H NMR ($CDCl_3$, 400 MHz) δ 9.01 (s, 1H), 8.36 (dd, J=8.3, 2.2 Hz, 1H), 7.31 (d, J=8.3 Hz, 1H), 7.02 (d, J=9.7 Hz, 2H), 6.71 (d, J=7.3 Hz, 4H), 3.53 (q, J=7.2 Hz, 8H), 1.30-1.24 (m, 12H). MS: $[M+H]^+$ calcd for $C_{28}H_{30}N_3O_5^+$ 488.2180; found: 488.7336.

Sodium (Z)-5-amino-2-(6-(methylamino)-3-(methylimino)-3H-xanthen-9-yl)benzoate (3a Under an argon atmosphere, compound 2 (55 mg) was treated with $CH_2Cl_2$/TFA (1/1, 2 mL) at r.t. overnight. The reaction mixture was dried under vacuum and used for the next step without further purification. The red solid was dissolved in MeOH/$H_2O$ (1/1, 5 mL) and refluxed with NaSH (0.5 g) for 1 h. The reaction mixture was concentrated and purified by FC (10%→40% MeOH in $CH_2Cl_2$) to give the target compound as a red solid (21.6 mg, 60%). $^1$H NMR (CD$_3$OD, 400 MHz): δ 7.40 (d, J=7.2 Hz, 2H), 7.33 (d, J=1.6 Hz, 1H), 6.95 (d, J=6.8 Hz, 1H), 6.86 (dd, J=2.0, 6.8 Hz, 1H), 6.79 (dd, J=1.6, 7.8 Hz, 2H), 6.72 (d, J=1.6 Hz, 2H), 3.01 (s, 6H). MS: [M+H]$^+$ calcd for C$_{22}$H$_{20}$N$_3$O$_3$$^+$ 374.15; found: 374.30.

5-Amino-2-(6-(dimethylamino)-3-(dimethyliminio)-3H-xanthen-9-yl)benzoate, sodium salt (3b Compound 3b was synthesized from 2b similarly as 3a except there was no treatment with TFA. The product was obtained as a red solid in 92% yield. $^1$H NMR (CD$_3$OD, 400 MHz) δ 7.48 (d, J=2.1 Hz, 1H), 7.38 (dd, J=9.5, 0.6 Hz, 2H), 7.09-6.95 (m, 4H), 6.90 (d, J=2.4 Hz, 2H), 3.27 (s, 12H). MS: [M+H]$^+$ calcd for C$_{24}$H$_{24}$N$_3$O$_3$$^+$ 402.1812; found: 402.5546.

5-Amino-2-(6-(diethylamino)-3-(diethyliminio)-3H-xanthen-9-yl)benzoate, sodium salt (3c Compound 3c was synthesized from 2c similarly as 3b in 40% yield. $^1$H NMR (CD$_3$OD, 400 MHz) δ 7.44 (d, J=9.5 Hz, 2H), 7.38 (d, J=2.3 Hz, 1H), 7.05-6.95 (m, 3H), 6.94-6.86 (m, 3H), 3.65 (q, J=7.1 Hz, 8H), 1.38-1.20 (m, 12H). MS: [M+H]$^+$ calcd for C$_{28}$H$_{32}$N$_3$O$_3$$^+$ 458.2438; found: 458.7400.

ZIGIR-1.

NaCNBH$_3$ (63 mg, 0.3 mmol, 10 equiv.) was added to a solution of compound 3a (10 mg, 0.03 mmol) and compound 4 (60 mg, 0.18 mmol, 6 equiv.; Li et al., 2011) in anhydrous MeOH containing dried Na$_2$SO$_4$ (200 mg, 100 eq). The mixture was stirred at r.t. overnight and filtered. The filtrate was concentrated under vacuum, and the resulting residue was purified by reversed phase column chromatography (LiChroprep RP-18) to afford ZIGIR as a red film in 30% yield: $^1$H NMR (CD$_3$OD, 400 MHz): δ 8.42 (td, J=0.8, 4.6 Hz, 2H), 7.74 (td, J=1.6, 7.6 Hz, 1H), 7.66 (td, J=1.6, 7.6 Hz, 1H), 7.36 (d, J=9.2 Hz, 2H), 7.30 (dd, J=0.8.7.2 Hz, 1H), 7.20-7.27 (m, 4H), 6.93 (d, J=8.4 Hz, 1H), 6.74 (dd, J=2.4, 9.2 Hz, 2H), 6.65-6.70 (m, 2H), 3.85 (s, 2H), 3.26 (t, J=6.0 Hz, 2H), 2.97 (s, 6H), 2.96-3.02 (m, 4H), 2.86 (t, J=6.0 Hz, 2H). MS: [M+H]$^+$ calcd for C$_{37}$H$_{37}$N$_6$O$_3$$^+$ 613.29; found: 613.60.

ZIGIR-2.

ZIGIR-2 was synthesized similarly as ZIGIR-1 from compounds 3b and 4 in 15% yield. $^1$H NMR (CD$_3$OD, 400 MHz) δ 8.44 (td, J=0.8, 4.6 Hz, 2H), 7.83-7.63 (m, 1H), 7.48 (d, J=9.5 Hz, 2H), 7.30 (dd, J=0.8, 7.2 Hz, 1H), 7.20-7.27 (m, 4H), 6.93 (d, J=8.4 Hz, 1H), 6.74 (dd, J=2.4, 9.2 Hz, 2H), 6.65-6.70 (m, 2H), 3.85 (s, 2H), 3.28 (s, 12H), 3.26 (t, J=6.0 Hz, 2H), 2.96-3.02 (m, 4H), 2.87 (t, J=6.1 Hz, 2H). MS: [M+H]$^+$ calcd for C$_{39}$H$_{41}$N$_6$O$_3$$^+$ 641.3235; found: 641.8668.

ZIGIR-3.

ZIGIR-3 was synthesized similarly as ZIGIR-1 from compounds 3c and 4 in 17% yield. $^1$H NMR (CD$_3$OD, 400 MHz) δ 8.44 (td, J=0.8, 4.6 Hz, 2H), 7.83-7.63 (m, 1H), 7.48 (d, J=9.5 Hz, 2H), 7.30 (dd, J=0.8, 7.2 Hz, 1H), 7.20-7.27 (m, 4H), 6.93 (d, J=8.4 Hz, 1H), 6.74 (dd, J=2.4, 9.2 Hz, 2H), 6.65-6.70 (m, 2H), 3.85 (s, 2H), 3.65 (q, J=7.2 Hz, 8H), 3.26 (t, J=6.0 Hz, 2H), 2.96-3.02 (m, 4H), 2.87 (t, J=6.1 Hz, 2H), 1.28 (t, J=7.0 Hz, 12H). MS: [M+H]$^+$ calcd for C$_{43}$H$_{49}$N$_6$O$_3$$^+$ 697.3861; found: 697.4884.

B. Photochemical Characterization of ZIGIRs In Vitro

Figures 11A, 11B:
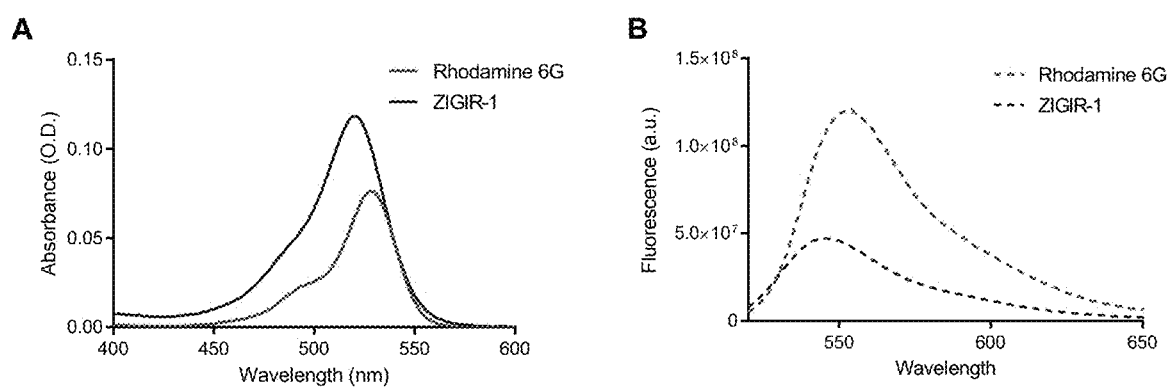
FIGS. 11A & 11B show example raw data for quantifying the fluorescence quantum yield of ZIGIR-1 by comparing the absorption (FIG. 11A) and emission spectra (FIG. 11B) of $Zn^{2+}$-bound ZIGIR-1 with a reference dye rhodamine 6G ($\Phi fl$=0.94 in MeOH). The quantum yield was calculated according to Brouwer, 2011.

UV-Vis spectra were recorded in a 1-cm path quartz cell on a Shimadzu 2401 PC spectrometer. Fluorescence excitation and emission spectra were recorded on a Fluorolog 3 spectrometer (Jobin-Yvon Horiba, Edison, N.J.). Zinc titration was performed by adding ZIGIRs (0.5 μM final concentration) to buffered Zn$^{2+}$ solutions containing 100 mM HEPES (pH 7.4). Nitrilotriacetic acid (NTA, 10 mM) and varying concentrations of ZnSO$_4$ (0-9 mM) were mixed to reach free Zn$^{2+}$ concentrations between 0.1 nM and 40 nM (Li et al., 2011). Zn$^{2+}$ concentrations above 40 nM were controlled by iminodiacetate (IDA, 10 mM) and varying amounts of ZnSO$_4$ (0-9.7 mM) in 100 mM HEPES (pH 7.4; Sasaki et al., 2011). To determine Zn$^{2+}$ binding dissociation constants ($K_d$(Zn$^{2+}$)), the Zn$^{2+}$ titration data were fitted to the least square exponential equation (Prism 7). Fluorescence quantum yields of ZIGIRs at pH 7.5 were determined using rhodamine 6G as the reference ($\Phi_{fl}$=0.94 in MeOH; Magde et al., 2002). An example in shown FIGS. 11A0B. To examine the pH sensitivity of ZIGIRs, the fluorescence emission spectra was recorded from pH 3-9.4 in either nominally Zn$^{2+}$-free solutions containing 5 mM iminodiacetate or in 25 μM ZnSO$_4$ solutions. The pH was controlled with 10 mM pH buffers including chloroacetic acid (pH 3.1), acetate (pH 4.1 and 5.0), 2-morpholinoethanesulfonic acid (MES, pH 6.14), HEPES (pH 7.5) and N-cyclohexyl-2-aminoethanesulfonic acid (CHES, pH 9.4).

To study the metal selectivity, the fluorescence of ZIGIR-1 (1 μM) or ZIGIR-2 (1 μM) was measured in the presence of 10 μM TPEN and an excess of metal ion including 1 mM KCl, 1 mM NaCl, 1 mM CaSO$_4$, 1 mM MgSO$_4$, 15 μM MnSO$_4$, 15 μM FeSO$_4$, 15 μM NiSO$_4$, 15 μM CoCl$_2$, 15 μM CuSO$_4$, 15 μM CdSO$_4$ or 15 μM ZnSO$_4$. The emission intensity was normalized to that of 15 μM ZnSO$_4$ (100%).

C. Cell Culture and Imaging

MIN-6 β cells were cultured as previously described (Li et al., 2011). HEK293 cells were cultured in DMEM medium supplemented with 10% FBS and 1% Penicillin/Streptomycin. T47D cells were cultured in RPMI-1640 medium supplemented with 10% FBS, 0.5% non-essential amino acids, 1 mM sodium pyruvate, 10 μg/mL geneticin and 0.01 mg/mL insulin. H1299 cells were cultured in RPMI-1640 medium supplemented with 10% FBS. All cells were maintained at 37° C. with 5% CO$_2$. For cell imaging, cells were seeded in 35-mm petri dishes with glass bottoms (MatTek) and cultured for ~24 hours to reach ~50% confluence. Prior to labeling, cells were washed with a secretion assay buffer (SAB) containing 114 mM NaCl, 4.7 mM KCl, 1.2 mM KH$_2$PO$_4$, 2.5 mM CaCl$_2$, 1.16 mM MgSO$_4$, 3 mM glucose, and 20 mM Hepes (pH 7.4). Cells were then incubated with ZIGIRs (0.5-1 μM) in SAB at 37° C. for 15 min, and washed with SAB before imaging on a Zeiss LSM 780 confocal microscope using 561 nm laser for exciting ZIGIR-2 (Em 570-650 nm) and 514 nm laser for exciting ZIGIR-1 (Em 516-650 nm). LysoTracker Green (ThermoFisher Scientific) was used at 0.4 μM to label acidic organelles and was added to cells <5 min before imaging. Image analysis was performed with ImageJ software. ZIGIR colocalization with LysoTracker Green was analyzed and quantified with JACoP plugin of ImageJ.

To correlate the intensity of ZIGIR-2 labeling and cellular insulin content by imaging, MIN-6 cells were first labeled and seeded on a 35 mm MatTek glass dish with ZIGIR-2. Cells were then imaged on a wide field fluorescence microscope (Axiovert 200, Carl Zeiss) equipped with an EMCCD camera (iXon 897, Andor) through a 40× oil objective. Excitation and emission light was filtered through band pass filters (Chroma Technology). ZIGIR-2 excitation: S555/28x; emission: ET605/52m. AF488 excitation: 5490/20×; emission: ET525/36. After ZIGIR-2 imaging, the cells were fixed on the microscope stage with 4% PFA (15 min, r.t.), permeabilized with PBST (PBS containing 0.15% triton X-100) for 10 min, washed with PBS, and incubated with a blocking buffer (10% vol/vol donkey serum in PBS) for 1 hr. After the blocking buffer was removed, the cells were treated with a guinea pig anti-insulin antibody (Dako A0564, 1:500 in blocking buffer) for 1 hr, washed with PBS (3×10 min), and treated with an AF488-conjugated donkey anti-guinea pig secondary antibody (Jackson 706-545-148, 1:200 in blocking buffer) for 40 min. After PBS washing for 10 min, cells were stained with DAPI (300 nM) for 5 min, washed with PBS and imaged again on the same microscope.

Immunofluorescence of other organelle-specific proteins were performed similarly and imaged on a confocal microscope. Antibodies included the lysosome marker Niemann-Pick C1 (rabbit anti-NPC1, Abcam 134113, 1:300), the Golgi marker GM130 (rabbit anti-GM130, Sigma G2654, 1:400), and a Cy3-conjugated donkey anti-rabbit secondary antibody (Jackson 711-165-152, 1:200).

D. Mouse Islet Isolation and Flow Cytometry Analysis

Mouse islets were isolated as previously described (Li et al., 2011) by perfusing Collagenase P (Roche, 1.4 mg/mL in HBSS with 5 mM glucose) through the common bile duct. Following a 15 min digestion at 37° C., the pancreas digestion was washed twice with HBSS by centrifugation and the islets were hand-picked under a dissection scope. Isolated islets were cultured 2-4 hours in RPMI-1640 medium (GIBCO, #11875-093) supplemented with 10% (v/v) FBS, 2.0 mM sodium-pyruvate, 100 U/mL penicillin and 100 mg/mL streptomycin at 37° C. in 5% $CO_2$. To distinguish islet β-cells from non-β cells, islets were labeled with a fluorescently labeled exendin-4 derivative as previously described (Kim et al., 2017). Briefly, Ex4-Cy5 (100 nM) was added to the culture medium 2 hours before islet dispersion. ZIGIR labeling was carried out subsequently after islet dispersion. Mouse islets were dispersed with 0.05% Trypsin solution in DPBS at 37° C. for 15 min. The dispersed islet cells were incubated with 0.5 μM ZIGIR-1 (or ZIGIR-2) at 37° C. for 15 min in the cell sorting buffer (SAB Buffer containing 3 mM glucose, 0.5% BSA and 0.1 mg/mL DNase I (Roche)). The cells were then washed twice with ice-cold SAB and resuspended in the cell sorting buffer. The labeled cells were analyzed by flow cytometry on a LSR-Fortessa cell analyzer (BD Biosciences). DAPI (200 ng/mL) was added to the cell suspension prior to flow cytometry to distinguish live cells (DAPI negative) from dead cells (DAPI positive). Only live cells were analyzed.

E. FACS of MIN6 Cells Labeled with ZIGIR-2

MIN-6 cells cultured on 60 mm petri dish were labeled with ZIGIR-2 as described herein. After labeling and washing, cells were resuspended in the sorting buffer, labeled with DAPI (200 ng/mL) and sorted on a FACSAria II SORP (BD Biosciences). Live cells were sorted into ZIGIR-2-High and ZIGIR-2-Low subsets. The sorted cells (in 0.5 mL sorting buffer) were adhered to polylysine coated glass slides using ThermoFisher Cytospin™ 4 Cytocentrifuge. The attached cells were then fixed with 4% PFA (15 min at r.t.) and immunostained for insulin as previously described. The stained cells were imaged by confocal microscopy (LSM780, Carl Zeiss) with 488 nm laser excitation. Insulin immunofluorescence signal was quantified with ImageJ.

All of the compounds, compositions, and methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the compounds, compositions, and methods without departing from the spirit, scope, and concept of the disclosure. All variations and modifications apparent to those skilled in the art are deemed to be within the spirit, scope, and concept of the disclosure as defined by the appended claims.

IX. REFERENCES

The following references to the extent that they provide exemplary procedural or other details supplementary to those set forth herein, are specifically incorporated herein by reference.

Andreini, C.; Banci, L.; Bertini, I.; Rosato, A., Counting the zinc-proteins encoded in the human genome. J Proteome Res 2006, 5 (1), 196-201.

Arrojo, E. D. R.; Jacob, S.; Garcia-Prieto, C. F.; Zheng, X.; Fukuda, M.; Nhu, H. T. T.; Stelmashenko, O.; Pecanha, F. L. M.; Rodriguez-Diaz, R.; Bushong, E.; Deerinck, T.; Phan, S.; Ali, Y.; Leibiger, I.; Chua, M.; Boudier, T.; Song, S. H.; Graf, M.; Augustine, G. J.; Ellisman, M. H.; Berggren, P. O., Structural basis for delta cell paracrine regulation in pancreatic islets. *Nature communications* 2019, 10 (1), 3700.

Artner, I.; Hang, Y.; Mazur, M.; Yamamoto, T.; Guo, M.; Lindner, J.; Magnuson, M. A.; Stein, R., MafA and MafB regulate genes critical to β-cells in a unique temporal manner. Diabetes 2010, 59 (10), 2530-2539.

Aydemir, T. B.; Liuzzi, J. P.; McClellan, S.; Cousins, R. J., Zinc transporter ZIP8 (SLC39A8) and zinc influence IFN-gamma expression in activated human T cells. J. Leukoc. Biol. 2009, 86 (2), 337-348.

Beija, M.; Afonso, C. A.; Martinho, J. M., Synthesis and applications of Rhodamine derivatives as fluorescent probes. Chem. Soc. Rev. 2009, 38 (8), 2410-2433.

Bloc, A.; Cens, T.; Cruz, H.; Dunant, Y., Zinc-induced changes in ionic currents of clonal rat pancreatic-cells: activation of ATP-sensitive K+ channels. J Physiol 2000, 529 Pt 3, 723-34.

Brouwer, A. M., Standards for photoluminescence quantum yield measurements in solution (IUPAC Technical Report). Pure and Applied Chemistry 2011, 83 (12), 2213-2228.

Burdette, S. C.; Frederickson, C. J.; Bu, W.; Lippard, S. J., ZP4, an improved neuronal $Zn^{2+}$ sensor of the Zinpyr family. J Am Chem Soc 2003, 125 (7), 1778-1787.

Burdette, S. C.; Walkup, G. K.; Spingler, B.; Tsien, R. Y.; Lippard, S. J., Fluorescent sensors for Zn(2+) based on a fluorescein platform: synthesis, properties and intracellular distribution. J Am Chem Soc 2001, 123 (32), 7831-7841.

Carlsson, S. R.; Roth, J.; Piller, F.; Fukuda, M., Isolation and characterization of human lysosomal membrane glycoproteins, h-lamp-1 and h-lamp-2. Major sialoglycoproteins carrying polylactosaminoglycan. *J Biol Chem* 1988, 263 (35), 18911-9.

Chabosseau, P.; Woodier, J.; Cheung, R.; Rutter, G. A., Sensors for measuring subcellular zinc pools. Metallomics: integrated biometal science 2018, 10 (2), 229-239.

Davidson, H. W.; Wenzlau, J. M.; O'Brien, R. M., Zinc transporter 8 (ZnT8) and beta cell function. *Trends Endocrinol Metab* 2014, 25 (8), 415-24.

De Young, M. B.; Nemeth, E. F.; Scarpa, A., Measurement of the internal pH of mast cell granules using microvolumetric fluorescence and isotopic techniques. Arch. Biochem.

Biophys. 1987, 254 (1), 222-233.

Dodson, G.; Steiner, D., The role of assembly in insulin's biosynthesis. Curr. Opin. Struct. Biol. 1998, 8 (2), 189-194.

Egerod, K. L.; Engelstoft, M. S.; Lund, M. L.; Grunddal, K. V.; Zhao, M.; BarirJensen, D.; Nygaard, E. B.; Petersen, N.; Holst, J. J.; Schwartz, T. W., Transcriptional and Functional Characterization of the G Protein-coupled Receptor Repertoire of Gastric Somatostatin Cells. Endocrinology 2015, 156 (11), 3909-3923.

Ellis, C.; Ramzy, A.; Kieffer, T. J., Regenerative medicine and cell-based approaches to restore pancreatic function. Nat Rev Gastroenterol Hepatol 2017, 14 (10), 612-628.

Emdin, S. O.; Dodson, G. G.; Cutfield, J. M.; Cutfield, S. M., Role of zinc in insulin biosynthesis. Some possible zinc-insulin interactions in the pancreatic β-cell. Diabetologia 1980, 19 (3), 174-182.

Ferri, G.; Digiacomo, L.; Lavagnino, Z.; Occhipinti, M.; Bugliani, M.; Cappello, V.; Caracciolo, G.; Marchetti, P.; Piston, D. W.; Cardarelli, F., Insulin secretory granules labelled with phogrin-fluorescent proteins show alterations in size, mobility and responsiveness to glucose stimulation in living beta-cells. *Scientific reports* 2019, 9 (1), 2890.

Flannick et al, Loss-of-function mutations in SLC30A8 protect against type 2 diabetes. *Nat Genet* 2014, 46 (4), 357-63.

Frederickson, C. J.; Koh, J. Y.; Bush, A. I., The neurobiology of zinc in health and disease. Nat Rev Neurosci 2005, 6 (6), 449-462.

Fu, J.; Githaka, J. M.; Dai, X.; Plummer, G.; Suzuki, K.; Spigelman, A. F.; Bautista, A.; Kim, R.; Greitzer-Antes, D.; Fox, J. E. M.; Gaisano, H. Y.; MacDonald, P. E., A glucose-dependent spatial patterning of exocytosis in human beta-cells is disrupted in type 2 diabetes. *JCI Insight* 2019, 5.

Gandasi, N. R.; Yin, P.; Omar-Hmeadi, M.; Ottosson Laakso, E.; Vikman, P.; Barg, S., Glucose-Dependent Granule Docking Limits Insulin Secretion and Is Decreased in Human Type 2 Diabetes. Cell Metab 2018, 27 (2), 470-478 e4.

Gee, K. R.; Zhou, Z. L.; Qian, W. J.; Kennedy, R., Detection and imaging of zinc secretion from pancreatic β-cells using a new fluorescent zinc indicator. J Am Chem Soc 2002, 124 (5), 776-778.

Hara, M.; Wang, X.; Kawamura, T.; Bindokas, V. P.; Dizon, R. F.; Alcoser, S. Y.; Magnuson, M. A.; Bell, G. I., Transgenic mice with green fluorescent protein-labeled pancreatic 3-cells. Am J Physiol Endocrinol Metab 2003, 284 (1), E177-E183.

Hara, T.; Takeda, T. A.; Takagishi, T.; Fukue, K.; Kambe, T.; Fukada, T., Physiological roles of zinc transporters: molecular and genetic importance in zinc homeostasis. J Physiol Sci 2017, 67 (2), 283-301.

Hardy, A. B.; Serino, A. S.; Wijesekara, N.; Chimienti, F.; Wheeler, M. B., Regulation of glucagon secretion by zinc: lessons from the beta cell-specific Znt8 knockout mouse model. Diabetes, obesity &metabolism 2011, 13 Suppl 1, 112-7.

Hessels, A. M.; Chabosseau, P.; Bakker, M. H.; Engelen, W.; Rutter, G. A.; Taylor, K. M.; Merkx, M., eZinCh-2 A Versatile, Genetically Encoded FRET Sensor for Cytosolic and Intraorganelle Zn(2+) Imaging. ACS Chem Biol 2015, 10 (9), 2126-2134.

Hessels, A. M.; Merkx, M., Genetically-encoded FRET-based sensors for monitoring Zn(2+) in living cells. Metallomics: integrated biometal science 2015, 7 (2), 258-266.

Higgins, M. E.; Davies, J. P.; Chen, F. W.; Ioannou, Y. A., Niemann-Pick C1 is a late endosome-resident protein that transiently associates with lysosomes and the trans-Golgi network.

Mol. Genet. Metab. 1999, 68 (1), 1-13.

Huang, L.; Shen, H.; Atkinson, M. A.; Kennedy, R. T., Detection of exocytosis at individual pancreatic β cells by amperometry at a chemically modified microelectrode. Proc Natl Acad Sci USA 1995, 92 (21), 9608-9612.

Hwang, J. J.; Lee, S. J.; Kim, T. Y.; Cho, J. H.; Koh, J. Y., Zinc and 4-hydroxy-8-nonenal mediate lysosomal membrane permeabilization induced by $H_2O_2$ in cultured hippocampal neurons. J Neurosci 2008, 28 (12), 3114-3122.

Ishihara, H.; Wollheim, C. B., Is zinc an intra-islet regulator of glucagon secretion? Diabetol Int 2016, 7 (2), 106-110.

Jayaraman, S., A novel method for the detection of viable human pancreatic β cells by flow cytometry using fluorophores that selectively detect labile zinc, mitochondrial membrane potential and protein thiols. Cytometry A 2008, 73 (7), 615-625.

Kaltenberg, J.; Plum, L. M.; Ober-Blobaum, J. L.; Honscheid, A.; Rink, L.; Haase, H., Zinc signals promote IL-8-dependent proliferation of T cells. Eur. J. Immunol. 2010, 40 (5), 14961503.

Kim, J.; Okamoto, H.; Huang, Z.; Anguiano, G.; Chen, S.; Liu, Q.; Cavino, K.; Xin, Y.; Na, E.; Hamid, R.; Lee, J.; Zambrowicz, B.; Unger, R.; Murphy, A. J.; Xu, Y.; Yancopoulos, G. D.; Li, W. H.; Gromada, J., Amino Acid Transporter Slc38a5 Controls Glucagon Receptor Inhibition-induced Pancreatic alpha Cell Hyperplasia in Mice. Cell Metab 2017, 25 (6), 1348-1361.

Komatsu, K.; Kikuchi, K.; Kojima, H.; Urano, Y.; Nagano, T., Selective zinc sensor molecules with various affinities for $Zn^{2+}$, revealing dynamics and regional distribution of synaptically released $Zn^{2+}$ in hippocampal slices. J Am Chem Soc 2005, 127 (29), 10197-10204.

Le Marchand, S. J.; Piston, D. W., Glucose suppression of glucagon secretion: metabolic and calcium responses from alpha-cells in intact mouse pancreatic islets. *J Biol Chem* 2010, 285 (19), 14389-98.

Leibiger, B.; Moede, T.; Muhandiramlage, T. P.; Kaiser, D.; Vaca Sanchez, P.; Leibiger, I. B.; Berggren, P. O., Glucagon regulates its own synthesis by autocrine signaling. *Proc Natl Acad Sci USA* 2012, 109 (51), 20925-30.

Li, D.; Chen, S.; Bellomo, E. A.; Tarasov, A. I.; Kaut, C.; Rutter, G. A.; Li, W. H., Imaging dynamic insulin release using a fluorescent zinc indicator for monitoring induced exocytotic release (ZIMIR). Proc Natl Acad Sci USA 2011, 108 (52), 21063-21068.

Li, D.; Huang, Z.; Chen, S.; Hu, Z.; Li, W. H., GLP-9 Receptor Mediated Targeting of a Fluorescent $Zn^{2+}$ Sensor to B Cell Surface for Imaging Insulin/$Zn^{2+}$ Release. Bioconjug Chem 2015, 26 (8), 1443-1450.

Li, D.; Liu, L.; Li, W. H., Genetic Targeting of a Small Fluorescent Zinc Indicator to Cell Surface for Monitoring Zinc Secretion. ACS Chem Biol 2015, 10 (4), 1054-1063.

Li, W. H., Fluorescent sensors for imaging zinc dynamics in biological fluids. In Optical Probes in Biology, Zhang, J.; Mehta, S.; Schultz, C., Eds. CRC Press: 2015; Vol. 291-316.

Lichten, L. A.; Cousins, R. J., Mammalian zinc transporters: nutritional and physiologic regulation. Annu. Rev. Nutr. 2009, 29, 153-176.

Lukowiak, B.; Vandewalle, B.; Riachy, R.; Kerr-Conte, J.; Gmyr, V.; Belaich, S.; Lefebvre, J.; Pattou, F., Identification and purification of functional human β-cells by a new specific zinc-fluorescent probe. J. Histochem. Cytochem. 2001, 49 (4), 519-528.

Magde, D.; Wong, R.; Seybold, P. G., Fluorescence quantum yields and their relation to lifetimes of rhodamine 6G and fluorescein in nine solvents: improved absolute standards for quantum yields. Photochem Photobiol 2002, 75 (4), 327-334.

Matthews, E. K.; McKay, D. B.; O'Connor, M. D.; Borowitz, J. L., Biochemical and biophysical characterization of insulin granules isolated from rat pancreatic islets by an iso-osmotic gradient. Biochim Biophys Acta 1982, 715 (1), 80-89.

McCormick, N.; Velasquez, V.; Finney, L.; Vogt, S.; Kelleher, S. L., X-ray fluorescence microscopy reveals accumulation and secretion of discrete intracellular zinc pools in the lactating mouse mammary gland. PLoS ONE 2010, 5 (6), e 11078.

Meeusen, J. W.; Tomasiewicz, H.; Nowakowski, A.; Petering, D. H., TSQ (6-methoxy-8-p-toluenesulfonamido-quinoline), a common fluorescent sensor for cellular zinc, images zinc proteins. Inorg Chem 2011, 50 (16), 7563-7573.

Michael, D. J.; Geng, X.; Cawley, N. X.; Loh, Y. P.; Rhodes, C. J.; Drain, P.; Chow, R. H., Fluorescent cargo proteins in pancreatic β-cells: design determines secretion kinetics at exocytosis. Biophys J 2004, 87 (6), L03-L05.

Michael, D. J.; Tapechum, S.; Rohan, J. G.; Johnson, J. M.; Chow, R. H., Fluorescent cargo proteins in peptidergic endocrine cells: cell type determines secretion kinetics at exocytosis. Ann N Y Acad Sci 2009, 1152, 7-17.

Minami, K.; Yano, H.; Miki, T.; Nagashima, K.; Wang, C. Z.; Tanaka, H.; Miyazaki, J. I.; Seino, S., Insulin secretion and differential gene expression in glucose-responsive and -unresponsive MIN6 sublines. Am J Physiol Endocrinol Metab 2000, 279 (4), E773-E781.

Miyazaki, J.; Araki, K.; Yamato, E.; Ikegami, H.; Asano, T.; Shibasaki, Y.; Oka, Y.; Yamamura, K., Establishment of a pancreatic β cell line that retains glucose-inducible insulin secretion: special reference to expression of glucose transporter isoforms. Endocrinology 1990, 127 (1), 126-132.

Muraro, M. J.; Dharmadhikari, G.; Grun, D.; Groen, N.; Dielen, T.; Jansen, E.; van Gurp, L.; Engelse, M. A.; Carlotti, F.; de Koning, E. J.; van Oudenaarden, A., A Single-Cell Transcriptome Atlas of the Human Pancreas. Cell Syst 2016, 3 (4), 385-394 e3.

Murgia, C.; Devirgiliis, C.; Mancini, E.; Donadel, G.; Zalewski, P.; Perozzi, G., Diabetes-linked zinc transporter ZnT8 is a homodimeric protein expressed by distinct rodent endocrine cell types in the pancreas and other glands. Nutr Metab Cardiovasc Dis 2009, 19 (6), 431-439.

Nakamura, N.; Rabouille, C.; Watson, R.; Nilsson, T.; Hui, N.; Slusarewicz, P.; Kreis, T. E.; Warren, G., Characterization of a cis-Golgi matrix protein, GM130. J Cell Biol 1995, 131 (6 Pt 2), 1715-1726.

Nicolson et al., Insulin storage and glucose homeostasis in mice null for the granule zinc transporter ZnT8 and studies of the type 2 diabetes-associated variants. Diabetes 2009, 58 (9), 2070-2083.

Patel, S. C.; Suresh, S.; Kumar, U.; Hu, C. Y.; Cooney, A.; Blanchette-Mackie, E. J.; Neufeld, E. B.; Patel, R. C.; Brady, R. O.; Patel, Y. C.; Pentchev, P. G.; Ong, W. Y., Localization of Niemann-Pick C1 protein in astrocytes: implications for neuronal degeneration in Niemann-Pick type C disease. Proc Natl Acad Sci USA 1999, 96 (4), 1657-1662.

Popovics, P.; Stewart, A. J., GPR39: a Zn(2+)-activated G protein-coupled receptor that regulates pancreatic, gastrointestinal and neuronal functions. Cell Mol Life Sci 2011, 68 (1), 85-95.

Qin, Y.; Miranda, J. G.; Stoddard, C. I.; Dean, K. M.; Galati, D. F.; Palmer, A. E., Direct comparison of a genetically encoded sensor and small molecule indicator: implications for quantification of cytosolic Zn(2+). ACS Chem Biol 2013, 8 (11), 2366-2371.

Que, E. L.; Bleher, R.; Duncan, F. E.; Kong, B. Y.; Gleber, S. C.; Vogt, S.; Chen, S.; Garwin, S. A.; Bayer, A. R.; Dravid, V. P.; Woodruff, T. K.; O'Halloran, T. V., Quantitative mapping of zinc fluxes in the mammalian egg reveals the origin of fertilization-induced zinc sparks. Nature chemistry 2015, 7 (2), 130-139.

Quoix, N.; Cheng-Xue, R.; Guiot, Y.; Herrera, P. L.; Henquin, J. C.; Gilon, P., The GluCre-ROSA26EYFP mouse: a new model for easy identification of living pancreatic alpha-cells. FEBS Lett 2007, 581 (22), 4235-4240.

Ravassard, P.; Hazhouz, Y.; Pechberty, S.; Bricout-Neveu, E.; Armanet, M.; Czernichow, P.; Scharfmann, R., A genetically engineered human pancreatic β cell line exhibiting glucose-inducible insulin secretion. The Journal of clinical investigation 2011, 121 (9), 3589-3597.

Rink, L., Zinc in Human Health. IOS Press: 2011; Vol. 76.

Rivera-Fuentes, P.; Wrobel, A. T.; Zastrow, M. L.; Khan, M.; Georgiou, J.; Luyben, T. T.; Roder, J. C.; Okamoto, K.; Lippard, S. J., A Far-Red Emitting Probe for Unambiguous Detection of Mobile Zinc in Acidic Vesicles and Deep Tissue. Chem Sci 2015, 6 (3), 1944-1948.

Roh, H. C.; Collier, S.; Guthrie, J.; Robertson, J. D.; Kornfeld, K., Lysosome-related organelles in intestinal cells are a zinc storage site in C. elegans. Cell Metab 2012, 15 (1), 88-99.

Rorsman, P.; Renstrom, E., Insulin granule dynamics in pancreatic beta cells. Diabetologia 2003, 46 (8), 1029-45.

Rorsman, P.; Huising, M. O., The somatostatin-secreting pancreatic delta-cell in health and disease. Nat Rev Endocrinol 2018, 14 (7), 404-414.

Rosengren, A. H.; Braun, M.; Mahdi, T.; Andersson, S. A.; Travers, M. E.; Shigeto, M.; Zhang, E.; Almgren, P.; Ladenvall, C.; Axelsson, A. S.; Edlund, A.; Pedersen, M. G.; Jonsson, A.; Ramracheya, R.; Tang, Y.; Walker, J. N.; Barrett, A.; Johnson, P. R.; Lyssenko, V.; McCarthy, M. I.; Groop, L.; Salehi, A.; Gloyn, A. L.; Renstrom, E.; Rorsman, P.; Eliasson, L., Reduced insulin exocytosis in human pancreatic beta-cells with gene variants linked to type 2 diabetes. Diabetes 2012, 61 (7), 1726-33.

Rutter, G. A.; Chimienti, F., SLC30A8 mutations in type 2 diabetes. Diabetologia 2015, 58 (1), 31-6.

Sasaki, H.; Hanaoka, K.; Urano, Y.; Terai, T.; Nagano, T., Design and synthesis of a novel fluorescence probe for $Zn^{2+}$ based on the spirolactam ring-opening process of rhodamine derivatives. Bioorg Med Chem 2011, 19 (3), 1072 1078.

Segerstolpe, A.; Palasantza, A.; Eliasson, P.; Andersson, E. M.; Andreasson, A. C.; Sun, X.; Picelli, S.; Sabirsh, A.; Clausen, M.; Bjursell, M. K.; Smith, D. M.; Kasper, M.; Ammala, C.; Sandberg, R., Single-Cell Transcriptome Profiling of Human Pancreatic Islets in Health and Type 2 Diabetes. Cell Metab 2016, 24 (4), 593-607.

Solomou, A.; Meur, G.; Bellomo, E.; Hodson, D. J.; Tomas, A.; Li, S. M.; Philippe, E.; Herrera, P. L.; Magnan, C.; Rutter, G. A., The Zinc Transporter Slc30a8/ZnT8 Is Required in a Subpopulation of Pancreatic alpha-cells for Hypoglycemia-induced Glucagon Secretion. J Biol Chem 2015, 290 (35), 2143221442.

Stiernet, P.; Guiot, Y.; Gilon, P.; Henquin, J. C., Glucose acutely decreases pH of secretory granules in mouse pancreatic islets. Mechanisms and influence on insulin secretion. J Biol Chem 2006, 281 (31), 22142-22151.

Tabei, S. M.; Burov, S.; Kim, H. Y.; Kuznetsov, A.; Huynh, T.; Jureller, J.; Philipson, L. H.; Dinner, A. R.; Scherer, N. F., Intracellular transport of insulin granules is a subordinated random walk. Proc Natl Acad Sci USA 2013, 110 (13), 4911-4916.

Taki, M.; Wolford, J. L.; O'Halloran, T. V., Emission ratiometric imaging of intracellular zinc: design of a benzoxazole fluorescent sensor and its application in two-photon microscopy. J Am Chem Soc 2004, 126 (3), 712-713.

Tamaki, M.; Fujitani, Y.; Hara, A.; Uchida, T.; Tamura, Y.; Takeno, K.; Kawaguchi, M.; Watanabe, T.; Ogihara, T.; Fukunaka, A.; Shimizu, T.; Mita, T.; Kanazawa, A.; Imaizumi, M. O.; Abe, T.; Kiyonari, H.; Hojyo, S.; Fukada, T.; Kawauchi, T.; Nagamatsu, S.; Hirano, T.; Kawamori, R.; Watada, H., The diabetes-susceptible gene SLC30A8/ZnT8 regulates hepatic insulin clearance. J. Clin. Invest. 2013, 123 (10), 4513-4524.

Tornehave, D.; Kristensen, P.; Romer, J.; Knudsen, L. B.; Heller, R. S., Expression of the GLP-9 receptor in mouse, rat, and human pancreas. J. Histochem. Cytochem. 2008, 56 (9), 841-851.

Vinkenborg, J. L.; Nicolson, T. J.; Bellomo, E. A.; Koay, M. S.; Rutter, G. A.; Merkx, M., Genetically encoded FRET sensors to monitor intracellular $Zn^{2+}$ homeostasis. Nat Methods 2009, 6 (10), 737-740.

Wellenreuther, G.; Cianci, M.; Tucoulou, R.; MeyerOlaucke, W.; Haase, H., The ligand environment of zinc stored in vesicles. Biochem Biophys Res Commun 2009, 380 (1), 198-203.

Wong, W. P.; Allen, N. B.; Meyers, M. S.; Link, E. O.; Zhang, X.; MacRenaris, K. W.; El Muayed, M., Exploring the Association Between Demographics, SLC30A8 Genotype, and Human Islet Content of Zinc, Cadmium, Copper, Iron, Manganese and Nickel. Scientific reports 2017, 7 (1), 473.

Wu, Y.; Peng, X.; Guo, B.; Fan, J.; Zhang, Z.; Wang, J.; Cui, A.; Gao, Y., Boron dipyrromethene fluorophore based fluorescence sensor for the selective imaging of Zn(II) in living cells. Org Biomol Chem 2005, 3 (8), 13871392.

Yamato, E.; Tashiro, F.; Miyazaki, J., Microarray analysis of novel candidate genes responsible for glucose-stimulated insulin secretion in mouse pancreatic β cell line MIN6. PLoS ONE 2013, 8 (4), e61211.

Yasuda, T.; Shibasaki, T.; Minami, K.; Takahashi, H.; Mizoguchi, A.; Uriu, Y.; Numata, T.; Mori, Y.; Miyazaki, J.; Miki, T.; Seino, S., Rim2alpha determines docking and priming states in insulin granule exocytosis. Cell Metab 2010, 12 (2), 117-129.

Zalewski, P. D.; Forbes, I. J.; Giannakis, C., Physiological role for zinc in prevention of apoptosis (gene-directed death). Biochem. Int. 1991, 24 (6), 1093-1101.

Zalewski, P. D.; Millard, S. H.; Forbes, I. J.; Kapaniris, O.; Slavotinek, A.; Betts, W. H.; Ward, A. D.; Lincoln, S. F.; Mahadevan, I., Video image analysis of labile zinc in viable pancreatic islet cells using a specific fluorescent probe for zinc. J. Histochem. Cytochem. 1994, 42 (7), 877-884.

What is claimed is:

1. A compound of the formula:

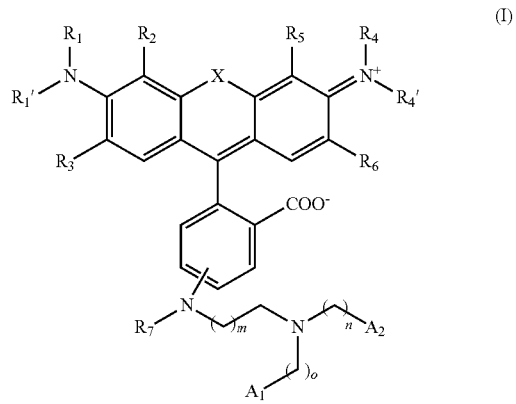

(I)

wherein:
X is —O—;
$R_1$ and $R_1'$ are each independently hydrogen; or alkyl$_{(C \leq 12)}$, alkenyl$_{(C \leq 12)}$, alkynyl$_{(C \leq 12)}$, acyl$_{(C \leq 12)}$, or a substituted version of any of these groups; or
$R_1$ and $R_1'$ are taken together and is alkanediyl$_{(C2-7)}$, substituted alkanediyl$_{(C2-7)}$, -alkanediyl$_{(C1-3)}$-O-alkanediyl$_{(C1-3)}$-, or substituted -alkanediyl$_{(C1-3)}$-O-alkanediyl$_{(C1-3)}$-;
$R_4$ and $R_4'$ are each independently hydrogen; or alkyl$_{(C \leq 12)}$, alkenyl$_{(C \leq 12)}$, alkynyl$_{(C \leq 12)}$, acyl$_{(C \leq 12)}$, or a substituted version of any of these groups; or
$R_4$ and $R_4'$ are taken together and is alkanediyl$_{(C2-7)}$, substituted alkanediyl$_{(C2-7)}$, -alkanediyl$_{(C1-3)}$-O-alkanediyl$_{(C1-3)}$-, or substituted -alkanediyl$_{(C1-3)}$-O-alkanediyl$_{(C1-3)}$-;
$R_2$, $R_3$, $R_5$, and $R_6$ are each independently hydrogen or halo;
$R_7$ is hydrogen, alkyl$_{(C \leq 12)}$, substituted alkyl$_{(C \leq 12)}$, acyl$_{(C \leq 12)}$, or substituted acyl$_{(C \leq 12)}$;
$A_1$ and $A_2$ are each independently heteroaryl$_{(C \leq 12)}$ or substituted heteroaryl$_{(C \leq 12)}$;
m is 1, 2, or 3;
n is 1, 2, 3, or 4; and
o is 1, 2, 3, or 4; or a compound of the formula:

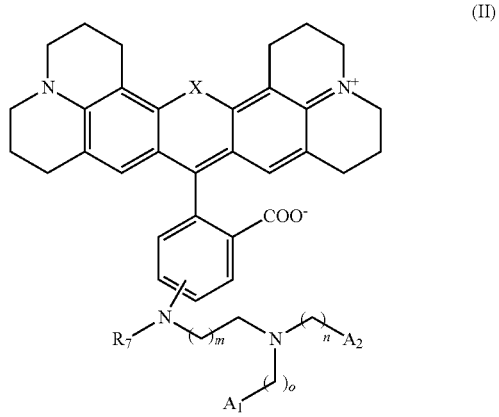

(II)

wherein:

X, $R_7$, $A_1$, $A_2$, m, n, and o are as defined above;

wherein a chemical group is used with the "substituted" modifier, one or more hydrogen atom has been replaced, independently at each instance, by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$;

or a zinc complex or a salt of either of these formulae.

2. The compound of claim 1, wherein the compound is a compound of formula (I) or a zinc complex or a salt thereof.

3. The compound of claim 1, wherein the compound is further defined as:

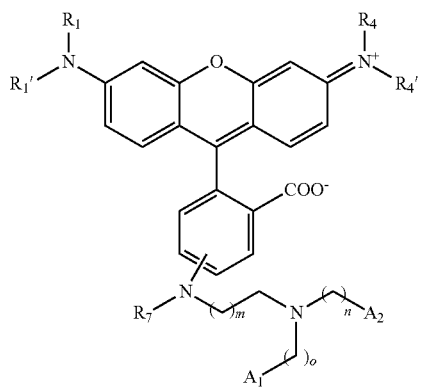

(III)

wherein:

$R_1$ and $R_1$' are each independently hydrogen; or
alkyl$_{(C≤12)}$, alkenyl$_{(C≤12)}$, alkynyl$_{(C≤12)}$, acyl$_{(C≤12)}$, or a substituted version of any of these groups; or $R_1$ and $R_1$' are taken together and is alkanediyl$_{(C2-7)}$, substituted alkanediyl$_{(C2-7)}$, -alkanediyl$_{(C1-3)}$-O-alkanediyl$_{(C1-3)}$-, or substituted -alkanediyl$_{(C1-3)}$-O-alkanediyl$_{(C1-3)}$-;

$R_4$ and $R_4$' are each independently hydrogen; or
alkyl$_{(C≤12)}$, alkenyl$_{(C≤12)}$, alkynyl$_{(C≤12)}$, acyl$_{(C≤12)}$, or a substituted version of any of these groups; or $R_4$ and $R_4$' are taken together and is alkanediyl$_{(C2-7)}$, substituted alkanediyl$_{(C2-7)}$, -alkanediyl$_{(C1-3)}$-O-alkanediyl$_{(C1-3)}$-, or substituted -alkanediyl$_{(C1-3)}$-O-alkanediyl$_{(C1-3)}$-;

$R_7$ is hydrogen, alkyl$_{(C≤12)}$, substituted alkyl$_{(C≤12)}$, acyl$_{(C≤12)}$, or substituted acyl$_{(C≤12)}$;

$A_1$ and $A_2$ are each independently heteroaryl$_{(C≤12)}$ or substituted heteroaryl$_{(C≤12)}$;

m is 1, 2, or 3;

n is 1, 2, 3, or 4; and o is 1, 2, 3, or 4;

or a zinc complex or a salt thereof.

4. The compound according to claim 1, wherein the compound is further defined as:

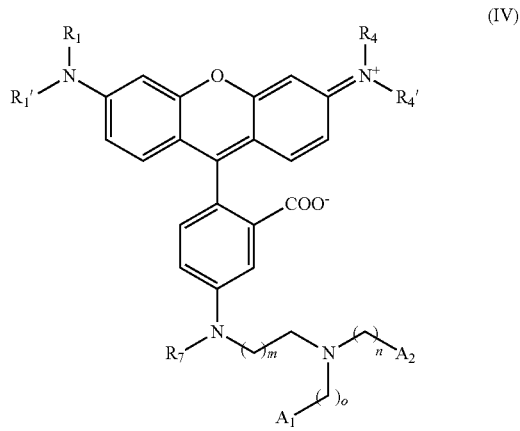

(IV)

wherein:

$R_1$ and $R_1$' are each independently hydrogen; or
alkyl$_{(C≤12)}$, alkenyl$_{(C≤12)}$, alkynyl$_{(C≤12)}$, acyl$_{(C≤12)}$, or a substituted version of any of these groups; or $R_1$ and $R_1$' are taken together and is alkanediyl$_{(C2-7)}$, substituted alkanediyl$_{(C2-7)}$, -alkanediyl$_{(C1-3)}$-O-alkanediyl$_{(C1-3)}$-, or substituted -alkanediyl$_{(C1-3)}$-O-alkanediyl$_{(C1-3)}$-;

$R_4$ and $R_4$' are each independently hydrogen; or
alkyl$_{(C≤12)}$, alkenyl$_{(C≤12)}$, alkynyl$_{(C≤12)}$, acyl$_{(C≤12)}$, or a substituted version of any of these groups; or $R_4$ and $R_4$' are taken together and is alkanediyl$_{(C2-7)}$, substituted alkanediyl$_{(C2-7)}$, -alkanediyl$_{(C1-3)}$-O-alkanediyl$_{(C1-3)}$-, or substituted -alkanediyl$_{(C1-3)}$-O-alkanediyl$_{(C1-3)}$-;

$R_7$ is hydrogen, alkyl$_{(C≤12)}$, substituted alkyl$_{(C≤12)}$, acyl$_{(C≤12)}$, or substituted acyl$_{(C≤12)}$;

$A_1$ and $A_2$ are each independently heteroaryl$_{(C≤12)}$ or substituted heteroaryl$_{(C≤12)}$;

m is 1, 2, or 3;

n is 1, 2, 3, or 4; and o is 1, 2, 3, or 4;

or a zinc complex or a salt thereof.

5. The compound according to claim 1, wherein $R_7$ is hydrogen.

6. The compound according to claim 1, wherein m is 1.

7. The compound according to claim 1, wherein n is 1.

8. The compound according to claim 1, wherein o is 2.

9. The compound according to claim 1, wherein $A_1$ is heteroaryl$_{(C≤12)}$.

10. The compound according to claim 1, wherein $A_2$ is heteroaryl$_{(C≤12)}$.

11. The compound according to claim 1, wherein $R_1$ is hydrogen.

12. The compound according to claim 1, wherein $R_1$ is alkyl$_{(C≤12)}$ or substituted alkyl$_{(C≤12)}$.

13. The compound according to claim 1, wherein $R_1$' is hydrogen.

14. The compound according to claim 1, wherein $R_1$' is alkyl$_{(C≤12)}$ or substituted alkyl$_{(C≤12)}$.

15. The compound according to claim 1, wherein $R_4$ is hydrogen.

16. The compound according to claim 1, wherein $R_4$ is alkyl$_{(C≤12)}$ or substituted alkyl$_{(C≤12)}$.

17. The compound according to claim 1, wherein $R_4'$ is hydrogen.
18. The compound according to claim 1, wherein $R_4'$ is alkyl$_{(C \leq 12)}$ or substituted alkyl$_{(C \leq 12)}$.
19. The compound according to claim 1, wherein the compound is further defined as:
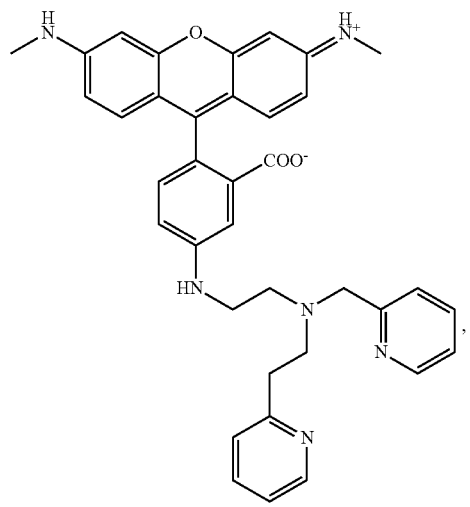
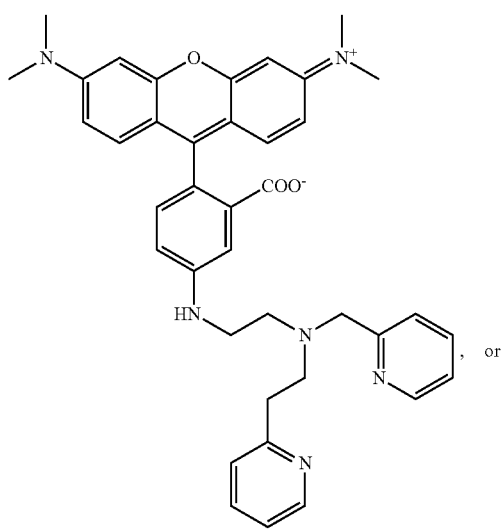
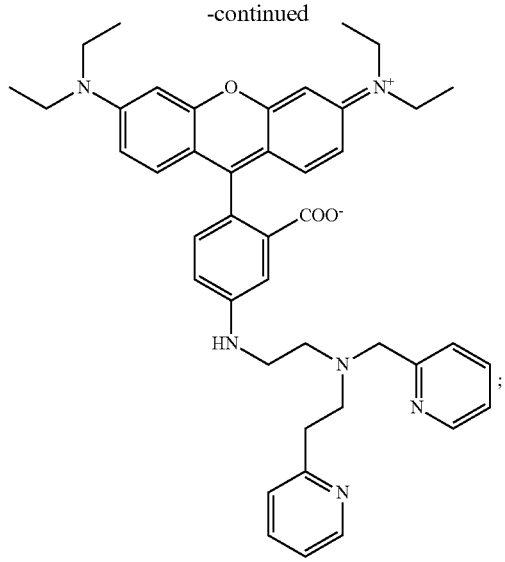
or a zinc complex or a salt thereof.
20. The zinc complex according to claim 19, where the zinc complex is further defined as:
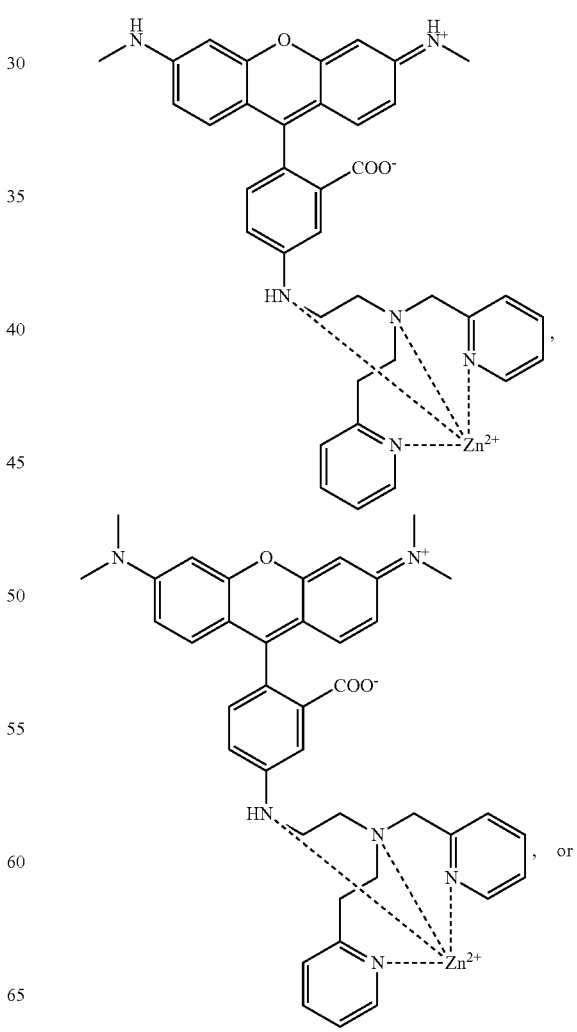

-continued

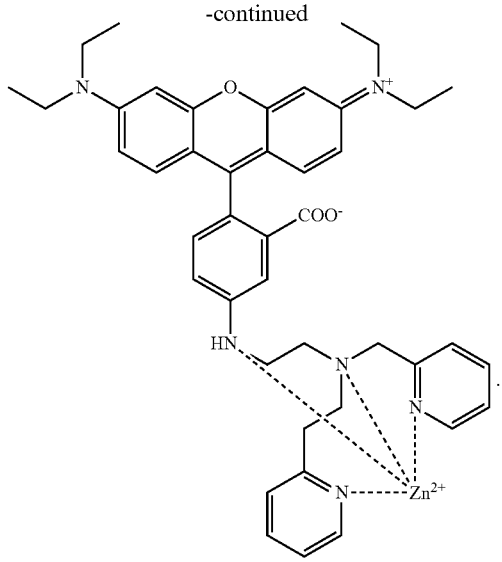

21. A method of detecting zinc ion ($Zn^{2+}$) in a cell comprising:
   a) contacting the cell with a compound according to claim 1; and
   b) detecting fluorescence of the said compound following binding of zinc ion by said compound.

22. A method of characterizing a cell comprising:
   a) contacting the cell with a compound according to claim 1; and
   b) detecting fluorescence using flow cytometry.

23. A method of sorting cells comprising:
   a) contacting the cells with a compound according to claim 1; and
   b) sorting the cells by fluorescence-activated cell sorting (FACS).

* * * * *